(12) United States Patent
Atienza et al.

(10) Patent No.: US 9,745,327 B2
(45) Date of Patent: Aug. 29, 2017

(54) BISPHENOLATE TRANSITION METAL COMPLEXES, PRODUCTION AND USE THEREOF

(71) Applicant: ExxonMobil Chemical Patents Inc., Baytown, TX (US)

(72) Inventors: Crisita Carmen H. Atienza, Houston, TX (US); David A. Cano, Houston, TX (US); John R. Hagadorn, Houston, TX (US); Rhutesh K. Shah, Katy, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/051,421

(22) Filed: Feb. 23, 2016

(65) Prior Publication Data

US 2016/0280722 A1 Sep. 29, 2016

Related U.S. Application Data

(60) Provisional application No. 62/137,417, filed on Mar. 24, 2015.

(51) Int. Cl.
*C07F 7/00* (2006.01)
*C08F 4/659* (2006.01)
*C08F 4/76* (2006.01)
*C08F 210/00* (2006.01)

(52) U.S. Cl.
CPC .............. *C07F 7/00* (2013.01); *C08F 210/00* (2013.01); *C08F 4/659* (2013.01); *C08F 4/65908* (2013.01); *C08F 4/65912* (2013.01); *C08F 2410/01* (2013.01)

(58) Field of Classification Search
None
See application file for complete search history.

(56) References Cited

U.S. PATENT DOCUMENTS

| 6,232,421 | B1 | 5/2001 | Fujita et al. |
| 6,333,389 | B2 | 12/2001 | Whiteker et al. |
| 6,333,423 | B1 | 12/2001 | Kol et al. |
| 6,596,827 | B2 | 7/2003 | Kol et al. |
| 6,906,153 | B2 | 6/2005 | Blom et al. |
| 7,812,104 | B2 | 10/2010 | Canich et al. |
| 7,847,099 | B2 | 12/2010 | Agapie et al. |
| 8,791,217 | B2 | 7/2014 | Hlavinka et al. |
| 8,907,032 | B2 | 12/2014 | Kol et al. |
| 2002/0019503 | A1 | 2/2002 | Kol et al. |

(Continued)

FOREIGN PATENT DOCUMENTS

| WO | 2007/130306 | 11/2007 |
| WO | 2012/098521 | 7/2012 |
| WO | 2014/014075 | 1/2014 |

OTHER PUBLICATIONS

Su et al., "Oxo-Bridged Bimetallic Group 4 Complexes Bearing Amine-Bis(benzotriazole phenolate) Derivatives as Bifunctional Catalysts for Ring-Opening Polymerization of Lactide adn Copolymerization of Carbon Dioxide with Cyclohexene Oxide," Organometallics, 2014, 33, 7091-7100.*

(Continued)

*Primary Examiner* — Catherine S Branch

(57) ABSTRACT

Bis phenolate transition metal complexes are disclosed for use in alkene polymerization, with optional chain transfer agent, to produce polyolefins.

33 Claims, 4 Drawing Sheets

(56) References Cited

U.S. PATENT DOCUMENTS

2013/0172498 A1     7/2013   Hlavinka et al.
2015/0166690 A1     6/2015   Evans et al.

OTHER PUBLICATIONS

Golisa, Suzanne R., et al., "Synthesis of Early Transition Metal Bisphenolate Complexes and Their Use as Olefin Polymerization Catalysts", Macromolecules, 2009, vol. 42, Issue 22, pp. 8751-8762.

Segal, Sharon, et al., "Zirconium and Titanium Diamine Bis(phenolate) Catalysts for α-Olefin Polymerization: From Atactic Oligo(1-hexene) to Ultrahigh-Molecular-Weight Isotactic Poly(1-hexene)", Organometallics, 2005, vol. 24, pp. 200-220.

Groysman et al., "*High Molecular Weight Atactic Polypropylene prepared by Zirconium Complexes of an Amine Bis(phenolate) Ligand*," Israel Journal of Chemistry, 2002, vol. 42, pp. 373-381.

Hustad et al., "*Continuous Production of Ethylene-Based Diblock Copolymers Using Coordinative Chain Transfer Polymerization,*" Macromolecules, 2007, vol. 40, pp. 7061-7064.

Reybuck et al., "*Amine Bis(phenolate) Ziroconium Complexes: Influence of Ligand Structure and Cocatalyst on Copolymerization Behavior,*" Macromolecules, 2005, vol. 38, pp. 2552-2558.

Tshuva et al., "*[ONXO]-Type Amine Bis(phenolate) Zirconium and Hafnium Complexes as Extrememly Active 1-Hexene Polymerization Catalysts,*" Organometallics, 2002, vol. 21, pp. 661-670.

Tshuva et al., "*Novel Ziroconium complexes of amine bis(phenolate) ligands. Remarkable reactivity in polymerization of hex-1-ene due to an extra donor arm,*" Chemistry Communication, 2000, pp. 379-380.

Tshuva et al., "*Zirconium Complexes of Amine-Bis(phenolate) Ligands as Catalysts for 1-Hexene Polymerization: Peripheral Structural Parameters Strongly Affect Reactivity,*" Organometallics, 2001, vol. 20, pp. 3017-3028.

Su et al., "Oxo-Brudged Bimetallic Group 4 Complexes Bearing Amine-Bis(benzotriazole phenolate) Derivatives as Bifunctional Catalysts for Ring-Opening Polymerization of Lactide and Copolymerization of Carbon Dioxide with Cyclohexene Oxide", Organometallics, vol. 33, No. 24, Dec. 22, 2014, pp. 7091-7100.

Cortes et al., "Titanium Complexes Supported by a Sterically Encumbering N-anchored Tris-arylphenoxide Ligand", Inorganic Chemistry Communications, vol. 8, No. 10, 2005, pp. 903-907.

Bernardinelli et al., "Stereoselective Dimerization of Racemic C3-symmetric Ti(IV) Amine Triphenolate Complexes", Dalton Transactions, The International Journal for Inorganic, Organometallic and Bioorganic Chemistry, No. 16, 2007, pp. 1573-1576.

\* cited by examiner

BISPHENOLATE TRANSITION METAL COMPLEXES, PRODUCTION AND USE THEREOF

STATEMENT OF RELATED APPLICATIONS

This invention claims priority to and the benefit of U.S. Ser. No. 62/137,417, filed Mar. 24, 2015, which is incorporated by reference herein.

FIELD OF THE INVENTION

The invention relates to bisphenolate transition metal complexes and processes for use of such complexes as catalysts for alkene polymerization processes, with or without chain transfer agents.

BACKGROUND OF THE INVENTION

Olefin polymerization catalysts are of great use in industry. Hence there is interest in finding new catalyst systems that increase the commercial usefulness of the catalyst and allow the production of polymers having improved properties.

Catalysts for olefin polymerization can be based on bisphenolate complexes as catalyst precursors, which are typically activated with an alumoxane or with an activator containing a non-coordinating anion.

Amine bis(phenolate) zirconium complexes have been used as transition metal components in the polymerization of ethylene and hexene, see for example, Macromolecules 2005, 38, 2552-2558.

U.S. Pat. No. 6,596,827 discloses amine bis(phenolate) compounds for use as alpha olefin polymerization catalysts.

Other references of interest include: U.S. Pat. No. 8,791,217; US 2013/0172498; U.S. Pat. No. 7,812,104; US 2014-0039137; U.S. Ser. No. 14/406,414, filed Aug. 2, 2013; U.S. Pat. No. 6,232,421; U.S. Pat. No. 6,333,389; U.S. Pat. No. 6,333,423; U.S. Pat. No. 8,907,032; U.S. Pat. No. 8,791,217; US 2002/0019503; WO 2012/098521; WO 2007/130306; Israel Journal of Chemistry Volume 42, 2002 pg. 373-381; Organometallics 2001, 20, 3017-3028; Macromolecules, 2007, 40, 7061-7064; Chem. Comm 2000, 379-380; Organometallics, 2001, 3017-3028; and Organometallics, 2002, 662-670.

There still is need for adding to the range of catalysts complexes that may be prepared and broaden their performance in alkene polymerization. Further, there is a need in the art for new catalysts with high activity that can produce crystalline polymers with good molecular weights.

SUMMARY OF THE INVENTION

This invention relates to transition metal complexes represented by the formula (I):

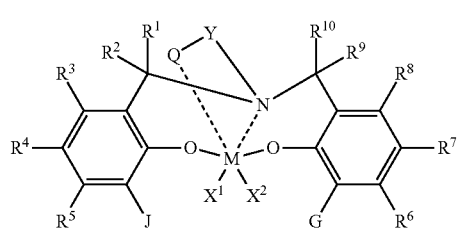

(I)

wherein M is a Group 4 transition metal;

$X^1$ and $X^2$ are, independently, a univalent $C_1$ to $C_{20}$ hydrocarbyl radical, a $C_1$ to $C_{20}$ substituted hydrocarbyl radical, a heteroatom or a heteroatom-containing group, or $X^1$ and $X^2$ join together to form a $C_4$ to $C_{62}$ cyclic or polycyclic ring structure;

each $R^1$, $R^2$, $R^3$, $R^4$, $R^5$, $R^6$, $R^7$, $R^8$, $R^9$ and $R^{10}$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more of $R^1$ to $R^{10}$ may independently join together to form a $C_4$ to $C_{62}$ cyclic or polycyclic ring structure, or a combination thereof; and Q is a neutral donor group;

J is a $C_7$ to $C_{60}$ fused polycyclic (e.g., having at least 2 ring structures) group, which optionally comprises up to 20 atoms from Groups 15 and 16, where at least one ring is aromatic and where at least one ring, which may or may not be aromatic, has at least 5 members;

G is as defined for J or may be hydrogen, a $C_1$-$C_{60}$ hydrocarbyl radical, a $C_1$-$C_{60}$ substituted hydrocarbyl radical, a heteroatom or a heteroatom-containing group, or may independently form a $C_4$ to $C_{60}$ cyclic or polycyclic ring structure with $R^6$, $R^7$, or $R^8$, or a combination thereof; and Y is a divalent $C_1$ to $C_{20}$ hydrocarbyl or divalent $C_1$ to $C_{20}$ substituted hydrocarbyl.

This invention also relates to a catalyst system comprising an activator and the catalysts described herein.

This invention also relates to a process to make polyolefin using the catalysts described herein.

This invention further relates to methods to polymerize olefins using the above complex in the presence of a chain transfer agent.

DETAILED DESCRIPTION OF THE INVENTION

Figure 1:
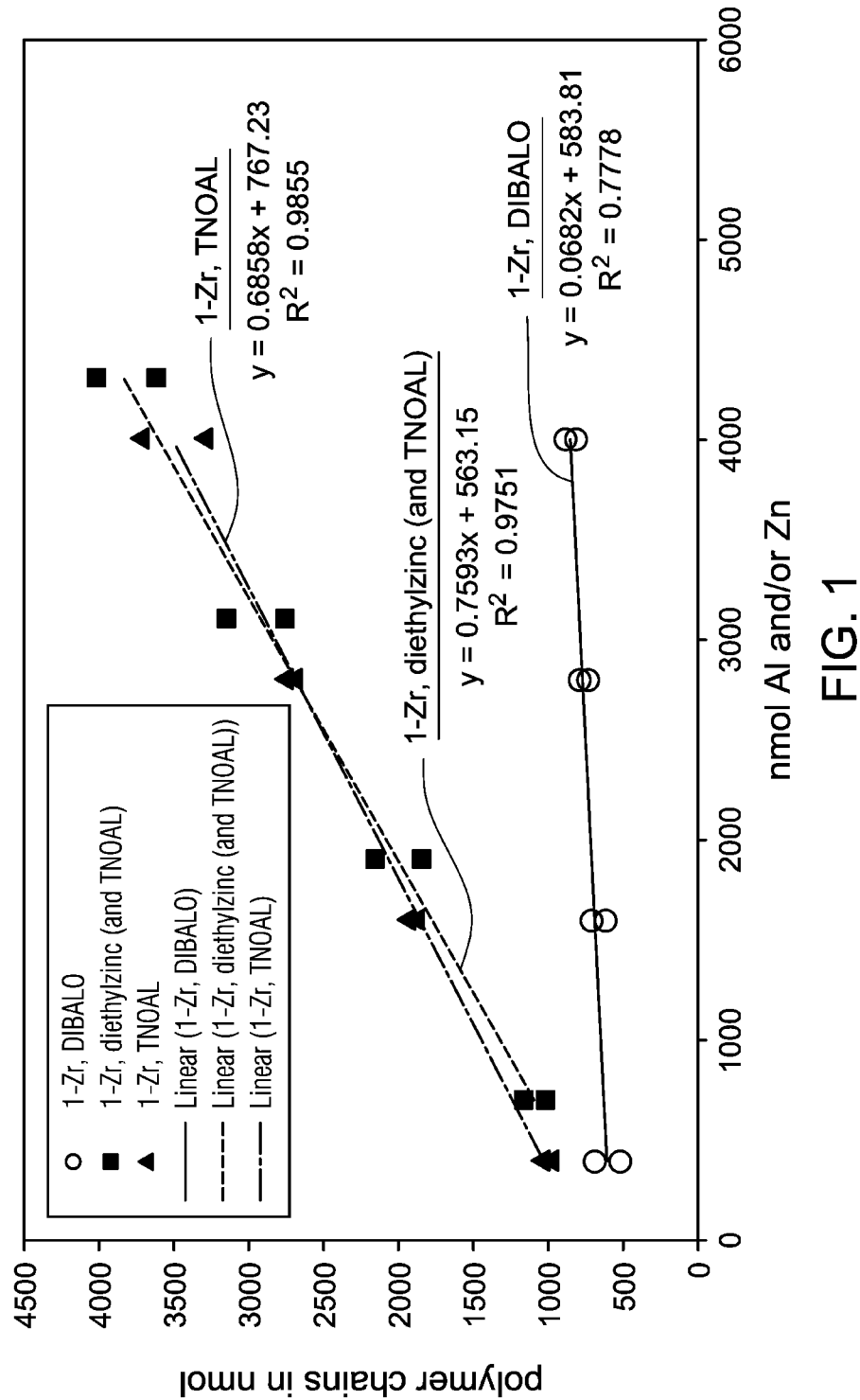
FIG. 1 presents a plot of polymer chains (nmol) versus nmol of metal (Al and/or Zn) from the chain transfer agent for entries 1 to 8, 17 to 24, and 48 to 55 in Table 10.

The specification describes transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator, which is believed to create a cation as a result of the removal of an anionic group, often referred to as a leaving group, from the transition metal.

In the structures depicted throughout this specification and the claims, a solid line indicates a bond, an arrow indicates that the bond may be active, and each dashed line represents a bond having varying degrees of covalency and a varying degree of coordination.

As used herein, the numbering scheme for the Periodic Table groups is the new notation as set out in Chemical and Engineering News, 63(5), 27 (1985).

As used herein, Me is methyl, Et is ethyl, Bu is butyl, t-Bu and tBu are tertiary butyl, Pr is propyl, iPr and iPr are isopropyl, Cy is cyclohexyl, THF (also referred to as the is tetrahydrofuran, Bn is benzyl, [$H_2CO$]$_x$ is paraformaldehyde, and Ph is phenyl.

The terms "hydrocarbyl radical," "hydrocarbyl" and "hydrocarbyl group" are used interchangeably throughout this document unless otherwise specified. For purposes of this disclosure, a hydrocarbyl radical is defined to be $C_1$ to $C_{70}$ radicals, or $C_1$ to $C_{20}$ radicals, or $C_1$ to $C_{10}$ radicals, or $C_6$ to $C_{70}$ radicals, or $C_6$ to $C_{20}$ radicals, or $C_7$ to $C_{20}$ radicals that may be linear, branched, or cyclic and aromatic or non-aromatic.

For purposes herein, a carbazole radical or substituted carbazole radical is represented by the formula:

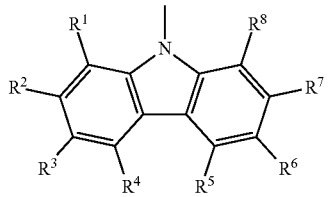

wherein each $R^1$ through $R^8$ is, independently, a hydrogen, a $C_1$-$C_{40}$ hydrocarbyl radical, a functional group comprising elements from Group 13 to 17 of the periodic table of the elements, or two or more of $R^1$ to $R^8$ may independently join together to form a $C_4$ to $C_{62}$ cyclic or polycyclic ring structure, or a combination thereof.

A substituted or unsubstituted fluorenyl radical is represented by the formula:

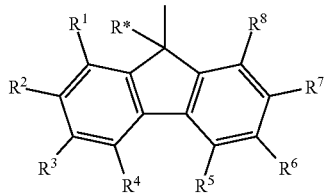

wherein each $R^1$ through $R^8$ is, independently, a hydrogen, a $C_1$-$C_{40}$ hydrocarbyl radical, a functional group comprising elements from Group 13 to 17 of the periodic table of the elements, or two or more of $R^1$ to $R^8$ may independently join together to form a $C_4$ to $C_{62}$ cyclic or polycyclic ring structure, or a combination thereof; R* is a hydrogen, a $C_1$-$C_{40}$ hydrocarbyl radical, a substituted $C_1$-$C_{40}$ hydrocarbyl radical (preferably R* is methyl, phenyl, tolyl, substituted phenyl, or substituted tolyl).

The term "catalyst system" is defined to mean a complex/activator pair. When "catalyst system" is used to describe such a pair before activation, it means the unactivated catalyst complex (precatalyst) together with an activator, optionally, a chain transfer agent, and, optionally, a co-activator. When it is used to describe such a pair after activation, it means the activated complex and the activator or other charge-balancing moiety. The transition metal compound may be neutral as in a precatalyst, or a charged species with a counter ion as in an activated catalyst system.

Complex, as used herein, is also often referred to as catalyst precursor, precatalyst, catalyst, catalyst compound, transition metal compound, or transition metal complex. These words are used interchangeably.

A "neutral donor group" is a neutrally charged group which donates one or more pairs of electrons to a metal.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

For the purposes of this invention, ethylene shall be considered a α-olefin.

For purposes of this invention and claims thereto, the term "substituted" means that a hydrogen group has been replaced with a heteroatom, or a heteroatom-containing group. For example, a "substituted hydrocarbyl" is a radical made of carbon and hydrogen where at least one hydrogen is replaced by a heteroatom or heteroatom-containing group. However, for purposes of this invention and claims thereto in relation to the catalyst compounds described herein, the term "substituted" means that a hydrogen group has been replaced with a hydrocarbyl group, a heteroatom, or a heteroatom-containing group. For example, methyl cyclopentadiene (Cp) is a Cp group substituted with a methyl group.

Unless otherwise noted, all molecular weights units (e.g., Mw, Mn, Mz) are g/mol.

Unless otherwise noted all melting points ($T_m$) are DSC second melt.

The term "aryl", "aryl radical", and/or "aryl group" refers to aromatic cyclic structures, which may be substituted with hydrocarbyl radicals and/or functional groups as defined herein.

As used herein the term "aromatic" also refers to pseudoaromatic heterocycles which are heterocyclic substituents that have similar properties and structures (nearly planar) to aromatic heterocyclic ligands, but are not by definition aromatic; likewise, the term aromatic also refers to substituted aromatics.

The term "continuous" means a system that operates without interruption or cessation. For example, a continuous process to produce a polymer would be one where the reactants are continually introduced into one or more reactors and polymer product is continually withdrawn.

A solution polymerization means a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are preferably not turbid as described in J. Vladimir Oliveira, C. Dariva and J. C. Pinto, Ind. Eng, Chem. Res. 29, 2000, 4627.

A bulk polymerization means a polymerization process in which the monomers and/or comonomers being polymerized are used as a solvent or diluent using little or no inert solvent as a solvent or diluent. A small portion of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

"Catalyst activity" is a measure of how many grams of polymer (P) are produced using a polymerization catalyst comprising W mmol of transition metal (M), over a period of time of T hours; and may be expressed by the following formula: $P/(T \times W)$.

For purposes herein, RT is room temperature, which is defined as 25° C. unless otherwise specified. All percentages are weight percent (wt %) unless otherwise specified.

Catalyst Compounds

In a first aspect of the invention there is provided a transition metal complex (optionally for use in alkene polymerization) represented by the formula (I):

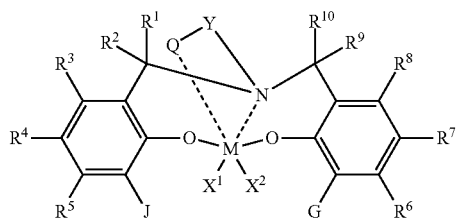

wherein M is a Group 4 transition metal (preferably Hf, Zr, or Ti, preferably Hf or Zr);

$X^1$ and $X^2$ are, independently, a univalent $C_1$ to $C_{20}$ hydrocarbyl radical, a $C_1$ to $C_{20}$ substituted hydrocarbyl radical, a heteroatom or a heteroatom-containing group, or $X^1$ and $X^2$ join together to form a $C_4$ to $C_{62}$ cyclic or polycyclic ring structure (preferably benzyl, methyl, ethyl, chloro, bromo and the like);

each $R^1$, $R^2$, $R^3$, $R^4$, $R^5$, $R^6$, $R^7$, $R^8$, $R^9$, and $R^{10}$ is, independently, a hydrogen, a $C_1$-$C_{40}$ hydrocarbyl radical, a substituted $C_1$-$C_{40}$ hydrocarbyl radical, a heteroatom, a heteroatom-containing group (alternately each $R^1$, $R^2$, $R^3$, $R^4$, $R^5$, $R^6$, $R^7$, $R^8$, $R^9$, and $R^{10}$ may be a functional group comprising of elements from Groups 13-17), or two or more of $R^1$ to $R^{10}$ may independently join together to form a $C_4$ to $C_{62}$ cyclic or polycyclic ring structure, or a combination thereof (preferably H, methyl, ethyl, propyl and the like); and Q is a neutral donor group, preferably a neutral donor group comprising at least one atom from Group 15 or Group 16;

J is a $C_7$ to $C_{60}$ fused polycyclic (e.g. having at least 2 ring structures) group, which, optionally, comprises up to 20 atoms from Groups 15 and 16, where at least one ring is aromatic and where at least one ring, which may or may not be aromatic, has at least 5 members; (preferably J comprises a five-membered ring (which may be saturated or aromatic) that is fused to at least one other cyclic group and is preferably bound to the rest of the ligand through the five-membered ring).

G is, independently, as defined for J, a hydrogen, a $C_1$-$C_{60}$ hydrocarbyl radical, a substituted hydrocarbyl radical, a heteroatom, or a heteroatom-containing group, or may independently form a $C_4$ to $C_{60}$ cyclic or polycyclic ring structure with $R^6$, $R^7$, or $R^6$, or a combination thereof; and Y is a divalent $C_1$ to $C_{20}$ hydrocarbyl or a substituted divalent hydrocarbyl group.

In another aspect, this invention relates to a catalyst compound represented by the formula (II) or (III):

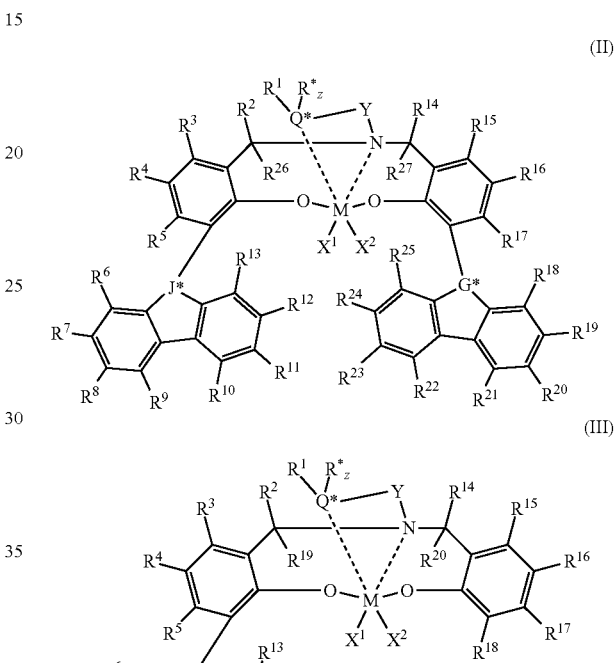

wherein:

M, $X^1$, $X^2$, $R^1$, $R^2$, $R^3$, $R^4$, $R^5$, $R^6$, $R^7$, $R^8$, $R^9$, $R^{10}$, and Y are as defined above;

each R''', R*, $R^{11}$, $R^{12}$, $R^{13}$, $R^{14}$, $R^{15}$, $R^{16}$, $R^{18}$, $R^{19}$, $R^{20}$, $R^{21}$, $R^{22}$, $R^{23}$, $R^{24}$, $R^{25}$, $R^{26}$, and $R^{27}$ is, independently, as defined for $R^1$ above;

Q* is a group 15 or 16 atom (preferably N, O, S or P);

z is 0 or 1;

J* is CR''' or N; and

G* is CR''' or N.

For purposes herein, any hydrocarbyl radical (and any alkyl radical) may be independently selected from methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl.

In any embodiment of the transition metal complexes described herein M may be Hf, Ti or Zr.

In any embodiment of the transition metal complexes described herein, each of $X^1$ and $X^2$ is independently selected from the group consisting of hydrocarbyl radicals having from 1 to 20 carbon atoms (such as methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl), hydrides, amides, alkoxides having from 1 to 20 carbon atoms, sulfides, phosphides, halides, sulfoxides, sulfonates, phosphonates, nitrates, carboxylates, carbonates and combinations thereof, preferably each of $X^1$ and $X^2$ is independently selected from the group consisting of halides (F, Cl, Br, I), alkyl radicals having from 1 to 7 carbon atoms (methyl, ethyl, propyl, butyl, pentyl, hexyl, heptyl, and isomers thereof), benzyl radicals, or a combination thereof.

In any embodiment of the transition metal complexes described herein Y is a divalent $C_1$-$C_{40}$ hydrocarbyl radical or divalent substituted hydrocarbyl radical comprising a portion that comprises a linker backbone comprising from 1 to 18 carbon atoms linking or bridging between Q and N. In an embodiment, Y is a divalent $C_1$-$C_{40}$ hydrocarbyl or substituted hydrocarbyl radical comprising a portion that comprises a linker backbone comprising from 1 to 18 carbon atoms linking Q and N wherein the hydrocarbyl comprises O, S, S(O), S(O)$_2$, Si(k)$_2$, P(R'), N or N(k), wherein each R' is independently a $C_1$-$C_{18}$ hydrocarbyl. In an embodiment, Y is selected from the group consisting of ethylene (—CH$_2$CH$_2$—) and 1,2-cyclohexylene. In an embodiment, Y is —CH$_2$CH$_2$CH$_2$— derived from propylene. In an embodiment, Y is selected form the group consisting of $C_1$ to $C_{20}$ alkyl groups, such as divalent methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl.

In a useful embodiment, each $R^1$, $R^2$, $R^3$, $R^4$, $R^5$, $R^6$, $R^7$, $R^8$, $R^9$, and $R^{10}$ is, independently, a hydrogen, a $C_1$-$C_{20}$ hydrocarbyl radical, a substituted $C_1$ to $C_{20}$ hydrocarbyl radical, or two or more of $R^1$ to $R^{10}$ may independently join together to form a $C_4$ to $C_{62}$ cyclic or polycyclic ring structure, or a combination thereof.

In any embodiment of the transition metal complexes described herein each R*, R'', $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, and $R^{27}$ is, independently, hydrogen, a halogen, a $C_1$ to $C_{30}$ hydrocarbyl radical, a $C_1$ to $C_{20}$ hydrocarbyl radical, or a $C_1$ to $C_{10}$ hydrocarbyl radical (such as methyl, ethyl, ethenyl and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl).

In any embodiment of the transition metal complexes described herein each R*, R'', $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, and $R^{27}$ is, independently, a substituted $C_1$ to $C_{30}$ hydrocarbyl radical, a substituted $C_1$ to $C_{20}$ hydrocarbyl radical, or a substituted $C_1$ to $C_{10}$ hydrocarbyl radical (such as 4-fluorophenyl, 4-chlorophenyl, 4-bromophenyl, 4-methoxyphenyl, 4-trifluoromethylphenyl, 4-dimethylaminophenyl, 4-trimethylsilylphenyl, 4-triethylsilylphenyl, trifluoromethyl, fluoromethyl, trichloromethyl, chloromethyl, mesityl, methylthio, phenylthio, (trimethylsilyl)methyl, and (triphenylsilyl)methyl).

In an embodiment, one or more of R*, R'', $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, and $R^{27}$ is a methyl radical, a fluoride, chloride, bromide, iodide, methoxy, ethoxy, isopropoxy, trifluoromethyl, dimethylamino, diphenylamino, adamantyl, phenyl, pentafluorphenyl, naphthyl, anthracenyl, dimethylphosphanyl, diisopropylphosphanyl, diphenylphosphanyl, methylthio, and phenylthio or a combination thereof.

In any embodiment of the transition metal complexes described herein Q* is N, O, S or P, preferably N, O, or S, preferably N or O, preferably N. In any embodiment of the transition metal complexes described herein when Q* is a Group 15 atom, z is 1, and when Q* is a group 16 atom, z is 0.

In any embodiment of the transition metal complexes described herein Q is preferably a neutral donor group comprising at least one atom from Group 15 or Group 16, preferably Q is NR'$_2$, OR', SR', PR'$_2$, where R is as defined for $R^1$ (preferably R' is methyl, ethyl, propyl, isopropyl, phenyl, cyclohexyl or linked together to form a five-membered ring such as pyrrolidinyl or a six-membered ring such as piperidinyl), preferably the -(-Q-Y—)— fragment can form a substituted or unsubstituted heterocycle which may or may not be aromatic and may have multiple fused rings (for example see compound 7-Zr, 7-Hf in the examples below). In any embodiment of the transition metal complexes described herein Q is preferably an amine, ether, or pyridine.

In a useful embodiment of the transition metal complexes described herein G* and J* are the same, preferably G* and J* are N, alternately G* and J* are CR''', where each R''' is H or a $C_1$ to $C_{12}$ hydrocarbyl or substituted hydrocarbyl (such as methyl, ethyl, ethenyl and isomers of propyl, butyl, pentyl, hexyl, heptyl, octyl, nonyl, decyl, undecyl, dodecyl, trifluoromethylphenyl, tolyl, phenyl, methoxyphenyl, tert-butylphenyl, fluorophenyl, diphenyl, dimethylaminophenyl, chlorophenyl, bromophenyl, iodophenyl, (trimethylsilyl)phenyl, (triethylsilyl)phenyl, (trimethylsilyl)methyl, (triethylsilyl)methyl). In a useful embodiment of the transition metal complexes described herein G* and J* are different.

In a useful embodiment of the transition metal complexes described herein G and J are the same, preferably G and J are carbazolyl, substituted carbazolyl, indolyl, substituted indolyl, indolinyl, substituted indolinyl, imidazolyl, substituted imidazolyl, indenyl, substituted indenyl, indanyl, substituted indanyl, fluorenyl, or substituted fluorenyl. In a useful embodiment of the transition metal complexes described herein G and J are different.

In an embodiment, M is Zr or Hf; $X^1$ and $X^2$ are benzyl radicals; $R^1$ is a methyl radical; $R^2$ through $R^{27}$ are hydrogen; Y is ethylene (—CH$_2$CH$_2$—), Q*, G* and J* are N, and Rz* is methyl radical.

In an embodiment, M is Zr or Hf; $X^1$ and $X^2$ are benzyl radicals; $R^4$ and $R^7$ are methyl radicals; $R^1$ through $R^3$, $R^5$ through $R^6$ and $R^8$ through $R^{10}$ are hydrogen; and Y is ethylene (—CH$_2$CH$_2$—), Q is an N-containing group, G and J are carbazolyl or fluorenyl. In a preferred combination, G and J are carbazolyl and Q is an amine group; or, G and J are substituted fluorenyl and Q is an amine, ether or pyridine.

In a particularly preferred embodiment of the invention, the catalyst complex is represented by formula (IV) or (V):

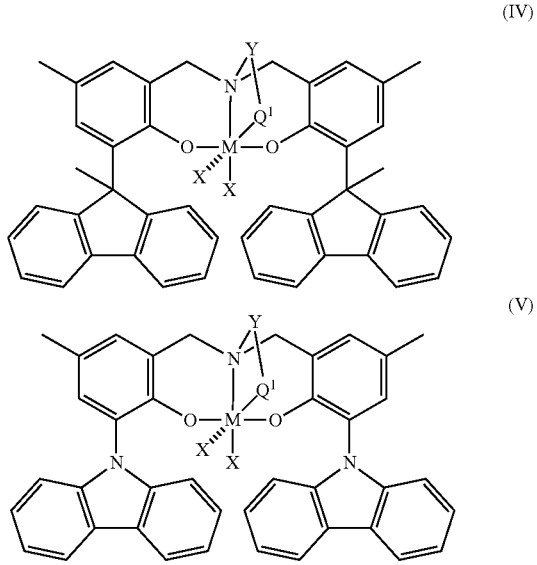

where Y is a $C_1$-$C_3$ divalent hydrocarbyl, $Q^1$ is $NR'_2$, $OR'$, $SR'$, $PR'_2$, where R is as defined for $R^1$ (preferably R is methyl, ethyl, propyl, isopropyl, phenyl, cyclohexyl or linked together to form a five-membered ring such as pyrrolidinyl or a six-membered ring such as piperidinyl), alternately the -(-Q-Y—)— fragment can form a substituted or unsubstituted heterocycle which may or may not be aromatic and may have multiple fused rings, M is Zr, Hf or Ti and each X is, independently, as defined for $X^1$ above, preferably each X is benzyl, methyl, ethyl, chloride, bromide or alkoxide.

Methods to Prepare the Catalyst Compounds.

Figure 4:
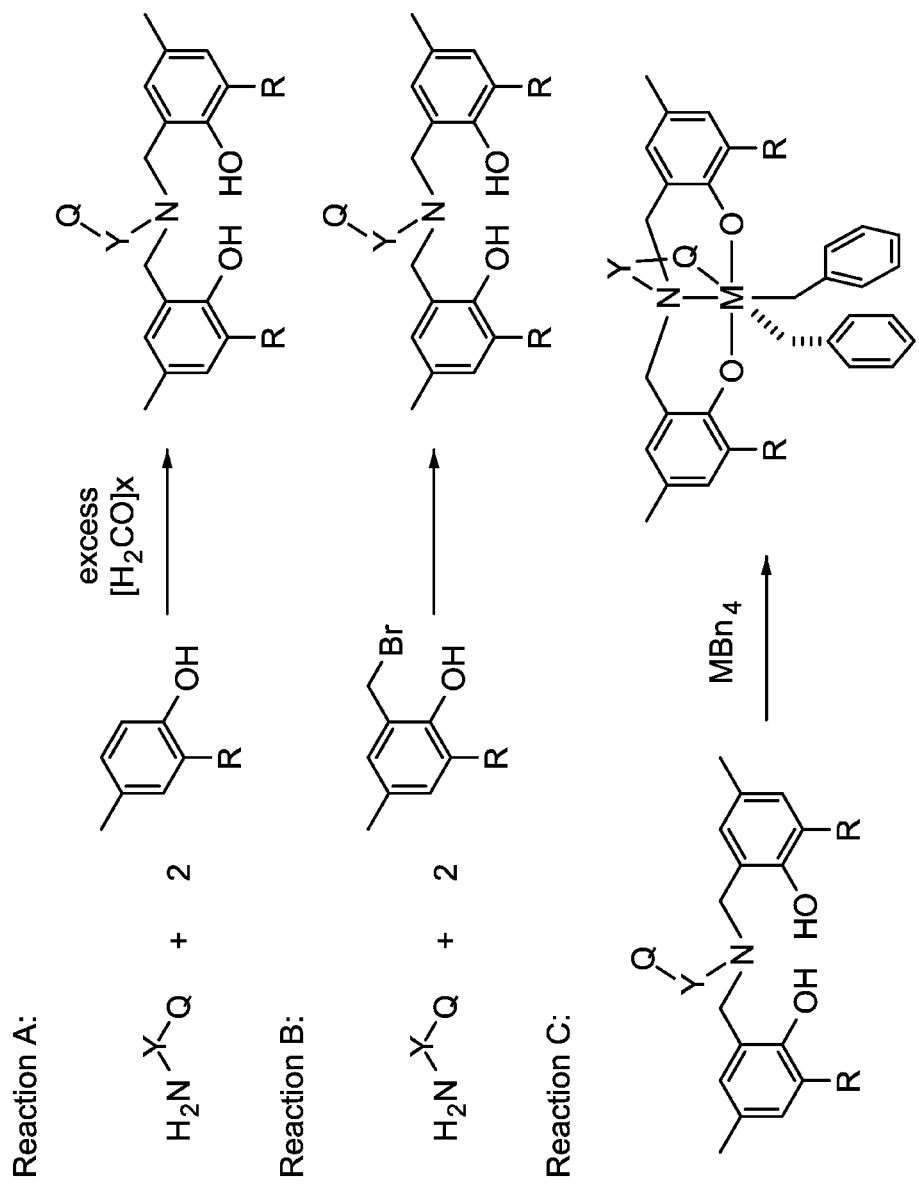
FIG. 4 is a depiction of reaction schemes.

In embodiments, the symmetric transition metal compounds may be prepared by two general synthetic routes. For example, the amine bis(phenolate) ligands may be prepared by a one-step Mannich reaction from the parent phenol (Reaction A, FIG. 4) or by a nucleophilic substitution reaction of the methylbromide derivative of the phenol (Reaction B, FIG. 4). The ligand is then typically reacted with the metal tetra-alkyl compound, e.g., tetrabenzyl, to yield the metal dibenzyl complex of the ligand (Reaction C, FIG. 4). In FIG. 4, M, Y, and Q are as defined for M, Y, and Q above, $[H_2CO]_x$ is paraformaldehyde, and each R is, independently, as defined for G or J above, provided that at least one R is as defined for J.

Activators

The terms "cocatalyst" and "activator" are used herein interchangeably and are defined to be any compound which can activate any one of the catalyst compounds described above by converting the neutral catalyst compound to a catalytically active catalyst compound cation.

After the complexes described above have been synthesized, catalyst systems may be formed by combining them with activators in any manner known from the literature including by supporting them for use in slurry or gas phase polymerization. The catalyst systems may also be added to or generated in solution polymerization or bulk polymerization (in the monomer). The catalyst system typically comprises a complex as described above and an activator such as alumoxane or a non-coordinating anion.

Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing noncoordinating or weakly coordinating anion.

Alumoxane Activators

In one embodiment, alumoxane activators are utilized as an activator in the catalyst system. Alumoxanes are generally oligomeric compounds containing —Al($R^1$)—O— subunits, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide, or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584).

When the activator is an alumoxane (modified or unmodified), some embodiments select the maximum amount of activator typically at up to a 5000-fold molar excess Al/M over the catalyst compound (per metal catalytic site). The minimum activator-to-catalyst-compound is a 1:1 molar ratio. Alternate preferred ranges include from 1:1 to 500:1, alternately from 1:1 to 200:1, alternately from 1:1 to 100:1, or alternately from 1:1 to 50:1.

In an alternate embodiment, little or no alumoxane is used in the polymerization processes described herein. Preferably, alumoxane is present at zero mole %, alternately the alumoxane is present at a molar ratio of aluminum to catalyst compound transition metal less than 500:1, preferably less than 300:1, preferably less than 100:1, preferably less than 1:1.

Non Coordinating Anion Activators

A noncoordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

"Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

The catalyst systems of this invention can include at least one non-coordinating anion (NCA) activator.

In a preferred embodiment boron containing NCA activators represented by the formula below can be used:

$$Z_d^+(A^{d-})$$

where: Z is (L-H) or a reducible Lewis acid; L is a neutral Lewis base; H is hydrogen;
(L-H) is a Bronsted acid; $A^{d-}$ is a boron containing non-coordinating anion having the charge d–; d is 1, 2, or 3.

The cation component, $Z_d^+$ may include Bronsted acids such as protons or protonated Lewis bases or reducible Lewis acids capable of protonating or abstracting a moiety, such as an alkyl or aryl, from the bulky ligand metallocene containing transition metal catalyst precursor, resulting in a cationic transition metal species.

The activating cation $Z_d^+$ may also be a moiety such as silver, tropylium, carboniums, ferroceniums and mixtures, preferably carboniums and ferroceniums. Most preferably $Z_d^+$ is triphenyl carbonium. Preferred reducible Lewis acids can be any triaryl carbonium (where the aryl can be substituted or unsubstituted, such as those represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl), preferably the reducible Lewis acids in formula (14) above as "Z" include those represented by the formula: $(Ph_3C)$, where Ph is a substituted or unsubstituted phenyl, preferably substituted with $C_1$ to $C_{40}$ hydrocarbyls or substituted a $C_1$ to $C_{40}$ hydrocarbyls, preferably $C_1$ to $C_{20}$ alkyls or aromatics or substituted $C_1$ to $C_{20}$ alkyls or aromatics, preferably Z is a triphenylcarbonium.

When $Z_d^+$ is the activating cation $(L-H)_d^+$, it is preferably a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers, tetrahydrothiophene, and mixtures thereof.

The anion component $A^{d-}$ includes those having the formula $[M^{k+}Q_n]^{d-}$ wherein k is 1, 2, or 3; n is 1, 2, 3, 4, 5, or 6 (preferably 1, 2, 3, or 4); n–k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst are the compounds described as (and particularly those specifically listed as) activators in U.S. Pat. No. 8,658,556, which is incorporated by reference herein.

Most preferably, the ionic stoichiometric activator $Z_d^+$ $(A^{d-})$ is one or more of N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetra(perfluorophenyl)borate.

Bulky activators are also useful herein as NCAs. "Bulky activator" as used herein refers to anionic activators represented by the formula:

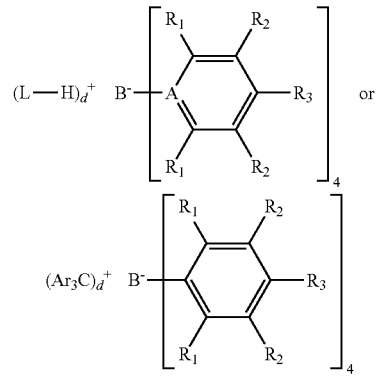

where: each $R_1$ is, independently, a halide, preferably a fluoride;
Ar is substituted or unsubstituted aryl group (preferably a substituted or unsubstituted phenyl), preferably substituted with $C_1$ to $C_{40}$ hydrocarbyls, preferably $C_1$ to $C_{20}$ alkyls or aromatics; each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group);
each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably R$_3$ is a fluoride or a C$_6$ perfluorinated aromatic hydrocarbyl group); wherein R$_2$ and R$_3$ can form one or more saturated or unsaturated, substituted or unsubstituted rings (preferably R$_2$ and R$_3$ form a perfluorinated phenyl ring); and L is a neutral Lewis base; (L-H)$^+$ is a Bronsted acid; d is 1, 2, or 3;

wherein the anion has a molecular weight of greater than 1020 g/mol;

wherein at least three of the substituents on the B atom each have a molecular volume of greater than 250 cubic Å, alternately greater than 300 cubic Å, or alternately greater than 500 cubic Å.

Preferably (Ar$_3$C)$_d^+$ is (Ph$_3$C)$_d^+$, where Ph is a substituted or unsubstituted phenyl, preferably substituted with C$_1$ to C$_{40}$ hydrocarbyls or substituted C$_1$ to C$_{40}$ hydrocarbyls, preferably C$_1$ to C$_{20}$ alkyls or aromatics or substituted C$_1$ to C$_{20}$ alkyls or aromatics.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: MV=8.3V$_s$, where V$_s$ is the scaled volume. V$_s$ is the sum of the relative volumes of the constituent atoms, and is calculated from the molecular formula of the substituent using the following table of relative volumes. For fused rings, the V$_s$ is decreased by 7.5% per fused ring.

| Element | Relative Volume |
| --- | --- |
| H | 1 |
| 1$^{st}$ short period, Li to F | 2 |
| 2$^{nd}$ short period, Na to Cl | 4 |
| 1$^{st}$ long period, K to Br | 5 |
| 2$^{nd}$ long period, Rb to I | 7.5 |
| 3$^{rd}$ long period, Cs to Bi | 9 |

For a list of particularly useful Bulky activators please see U.S. Pat. No. 8,658,556, which is incorporated by reference herein.

In another embodiment, one or more of the NCA activators is chosen from the activators described in U.S. Pat. No. 6,211,105.

Preferred activators include N,N-dimethylanilinium tetrakis(perfluoronaphthyl)borate, N,N-dimethylanilinium tetrakis(perfluorobiphenyl)borate, N,N-dimethylanilinium tetrakis(perfluorophenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetrakis(perfluorophenyl)borate, [Ph$_3$C$^+$][B(C$_6$F$_5$)$_4^-$], [Me$_3$NH$^+$][B(C$_6$F$_5$)$_4^-$]; 1-(4-(tris(pentafluorophenyl)borate)-2,3,5,6-tetrafluorophenyl)pyrrolidinium; and tetrakis(pentafluorophenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluorophenyl)borate, triphenylcarbenium tetrakis-(2,3,4,6-tetrafluorophenyl) borate, triphenylcarbenium tetrakis(perfluoronaphthyl) borate, triphenylcarbenium tetrakis(perfluorobiphenyl) borate, triphenylcarbenium tetrakis(3,5-bis(trifluoromethyl)phenyl)borate).

In another embodiment, the activator comprises one or more of trialkylammonium tetrakis(pentafluorophenyl)borate, N,N-dialkylanilinium tetrakis(pentafluorophenyl)borate, N,N-dimethyl-(2,4,6-trimethylanilinium)tetrakis(pentafluorophenyl)borate, trialkylammonium tetrakis-(2,3,4,6-tetrafluorophenyl) borate, N,N-dialkylanilinium tetrakis-(2,3,4,6-tetrafluorophenyl)borate, trialkylammonium tetrakis(perfluoronaphthyl)borate, N,N-dialkylanilinium tetrakis(perfluoronaphthyl)borate, trialkylammonium tetrakis(perfluorobiphenyl)borate, N,N-dialkylanilinium tetrakis(perfluorobiphenyl)borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl)phenyl)borate, di-(i-propyl)ammonium tetrakis(pentafluorophenyl)borate, (where alkyl is methyl, ethyl, propyl, n-butyl, sec-butyl, or t-butyl).

The typical activator-to-catalyst ratio, e.g., all NCA activators-to-catalyst ratio is about a 1:1 molar ratio. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

It is also within the scope of this invention that the catalyst compounds can be combined with combinations of alumoxanes and NCA's (see, for example, U.S. Pat. No. 5,153,157; U.S. Pat. No. 5,453,410; EP 0 573 120; WO 94/07928; and WO 95/14044), which discuss the use of an alumoxane in combination with an ionizing activator).

Scavengers and Co-Activators

The catalyst system may further include scavengers and/or co-activators. In some embodiments, when using the complexes described herein, particularly when they are immobilized on a support, the catalyst system will additionally comprise one or more scavenging compounds. Here, the term scavenging compound means a compound that removes polar impurities from the reaction environment. A scavenger is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments, a co-activator can be pre-mixed with the transition metal compound to form an alkylated transition metal compound.

Typically, the scavenging compound will be an organometallic compound such as the Group-13 organometallic compounds of U.S. Pat. No. 5,153,157; U.S. Pat. No. 5,241,025; WO 91/09882; WO 94/03506; WO 93/14132; and that of WO 95/07941. Exemplary compounds include triethyl aluminum, triethyl borane, tri-iso-butyl aluminum, methyl alumoxane, iso-butyl alumoxane, and tri-n-octyl aluminum. Those scavenging compounds having bulky or C$_6$-C$_{20}$ linear hydrocarbyl substituents connected to the metal or metalloid center usually minimize adverse interaction with the active catalyst. Examples include triethylaluminum, but more preferably, bulky compounds such as tri-iso-butyl aluminum, tri-iso-prenyl aluminum, and long-chain linear alkyl-substituted aluminum compounds, such as tri-n-hexyl aluminum, tri-n-octyl aluminum, or tri-n-dodecyl aluminum. When alumoxane is used as the activator, any excess over that needed for activation will scavenge impurities and additional scavenging compounds may be unnecessary. Alumoxanes also may be added in scavenging quantities with other activators, e.g., methylalumoxane, [Me$_2$HNPh]$^+$[B(pfp)$_4$]$^-$ or B(pfp)$_3$ (perfluorophenyl=pfp=C$_6$F$_5$). In an embodiment, the scavengers are present at less than 14 wt %, or from 0.1 to 10 wt %, or from 0.5 to 7 wt %, by weight of the catalyst system.

Suitable aluminum alkyl or organoaluminum compounds which may be utilized as co-activators include, for example, trimethylaluminum, triethylaluminum, triisobutylaluminum, tri-n-hexylaluminum, tri-n-octylaluminum and the like. In an embodiment, the co-activators are present at less than 14 wt %, or from 0.1 to 10 wt %, or from 0.5 to 7 wt %, by weight of the catalyst system. Alternately, the complex-to-co-activator molar ratio is from 1:100 to 100:1; 1:75 to 75:1; 1:50 to 50:1; 1:25 to 25:1; 1:15 to 15:1; 1:10 to 10:1; 1:5 to 5:1, 1:2 to 2:1; 1:100 to 1:1; 1:75 to 1:1; 1:50 to 1:1; 1:25 to 1:1; 1:15 to 1:1; 1:10 to 1:1; 1:5 to 1:1; 1:2 to 1:1; 1:10 to 2:1.

Chain Transfer Agents (CTAs)

A "chain transfer agent" is any agent capable of hydrocarbyl and/or polymeryl group exchange between a coordinative polymerization catalyst and the metal center of the chain transfer agent during a polymerization process. The chain transfer agent can be any desirable chemical compound such as those disclosed in WO 2007/130306. Preferably, the chain transfer agent is selected from Group 2, 12 or 13 alkyl or aryl compounds; preferably zinc, magnesium or aluminum alkyls or aryls; preferably where the alkyl is a C$_1$ to C$_{30}$ alkyl, alternately a C$_2$ to C$_{20}$ alkyl, alternately a C$_3$ to C$_{12}$ alkyl, typically selected independently from methyl, ethyl, propyl, butyl, isobutyl, tertbutyl, pentyl, hexyl, cyclohexyl, phenyl, octyl, nonyl, decyl, undecyl, and dodecyl; and where di-ethylzinc is particularly preferred.

In a particularly useful embodiment, this invention relates to a catalyst system comprising activator, catalyst complex as described herein, and chain transfer agent wherein the chain transfer agent is selected from Group 2, 12, or 13 alkyl or aryl compounds.

In a particularly useful embodiment, the chain transfer agent is selected from dialkyl zinc compounds, where the alkyl is selected independently from methyl, ethyl, propyl, butyl, isobutyl, tertbutyl, pentyl, hexyl, cyclohexyl, and phenyl.

In a particularly useful embodiment, the chain transfer agent is selected from trialkyl aluminum compounds, where the alkyl is selected independently from methyl, ethyl, propyl, butyl, isobutyl, tertbutyl, pentyl, hexyl, and cyclohexyl.

In a particularly useful embodiment, the chain transfer agent is selected from tri aryl aluminum compounds where the aryl is selected from phenyl and substituted phenyl.

The inventive process may be characterized by the transfer of at least 0.5 polymer chains (preferably 0.5 to 3) polymer chains, where n is the maximum number of polymer chains that can be transferred to the chain transfer agent metal, preferably n is 1 to 3 for trivalent metals (such as Al) and 1 to 2 for divalent metals (such as Zn), preferably n is 1.5 to 3 for trivalent metals (such as Al) and 1.5-2 for divalent metals (such as Zn). The number of chains transferred per metal is the slope of the plot of moles of polymer produced versus the moles of the chain transfer agent metal (as determined from at least four points, CTA metal:catalyst transition metal of 20:1, 80:1, 140:1 and 200:1, using least squares fit (Microsoft™ Excel 2010, version 14.0.7113.5000 (32 bit)) to draw the line. For example, in Table 10, for entries 1-8, the slope is 0.0682 and for entries 17-24, the slope is 0.7593. Useful chain transfer agents are typically present at from 10 or 20 or 50 or 100 equivalents to 600 or 700 or 800 or 1000 or 2000 or 4000 equivalents relative to the catalyst component. Alternately the chain transfer agent is preset at a catalyst complex-to-CTA molar ratio of from about 1:12,000 to 10:1; alternatively 1:6,000; alternatively, 1:3,000 to 10:1; alternatively 1:2,000 to 10:1; alternatively 1:1,000 to 10:1; alternatively, 1:500 to 1:1; alternatively 1:300 to 1:1; alternatively 1:200 to 1:1; alternatively 1:100 to 1:1; alternatively 1:50 to 1:1; alternatively 1:10 to 1:1.

Useful chain transfer agents include diethylzinc, tri-n-octyl aluminum, trimethylaluminum, triethylaluminum, triisobutylaluminum, tri-n-hexylaluminum, diethyl aluminum chloride, dibutyl zinc, di-n-propylzinc, di-n-hexylzinc, di-n-pentylzinc, di-n-decylzinc, di-n-dodecylzinc, di-n-tetradecylzinc, di-n-hexadecylzinc, di-n-octadecylzinc, diphenylzinc, diisobutylaluminum hydride, diethylaluminum hydride, di-n-octylaluminum hydride, dibutylmagnesium, diethylmagnesium, dihexylmagnesium, and triethylboron.

In a preferred embodiment, two or more complexes are combined with diethyl zinc and/or tri-n-octylaluminum in the same reactor with monomer(s). Alternately, one or more complexes is/are combined with another catalyst (such as a metallocene) and diethyl zinc and/or tri-n-octylaluminum in the same reactor with monomer(s).

In a preferred embodiment, one or more complexes is/are combined with a mixture of diethyl zinc and an aluminum reagent in the same reactor with monomer(s). Alternately, one or more complexes is/are combined with two chain transfer agents in the same reactor with monomer(s).

Supports

In some embodiments, the complexes described herein may be supported (with or without an activator) by any method effective to support other coordination catalyst systems, effectively meaning that the catalyst so prepared can be used for oligomerizing or polymerizing olefin in a heterogeneous process. The catalyst precursor, activator, co-activator, if needed, suitable solvent, and support may be added in any order or simultaneously. Typically, the complex and activator may be combined in solvent to form a solution. Then the support is added, and the mixture is stirred for 1 minute to 10 hours. The total solution volume may be greater than the pore volume of the support, but some embodiments limit the total solution volume below that needed to form a gel or slurry (about 90% to 400%, preferably about 100-200% of the pore volume). After stirring, the residual solvent is removed under vacuum, typically at ambient temperature and over 10-16 hours. But greater or lesser times and temperatures are possible.

The complex may also be supported absent the activator; in that case, the activator (and co-activator if needed) is added to a polymerization process's liquid phase. Additionally, two or more different complexes may be placed on the same support. Likewise, two or more activators or an activator and co-activator may be placed on the same support.

Suitable solid particle supports are typically comprised of polymeric or refractory oxide materials, each being preferably porous. Preferably any support material that has an average particle size greater than 10 µm is suitable for use in this invention. Various embodiments select a porous support material, such as for example, talc, inorganic oxides, inorganic chlorides, for example, magnesium chloride and resinous support materials such as polystyrene polyolefin or polymeric compounds or any other organic support material and the like. Some embodiments select inorganic oxide materials as the support material including Group-2, -3, -4, -5, -13, or -14 metal or metalloid oxides. Some embodiments select the catalyst support materials to include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can, optionally, double as the activator component, however, an additional activator may also be used.

The support material may be pretreated by any number of methods. For example, inorganic oxides may be calcined, chemically treated with dehydroxylating agents, such as aluminum alkyls and the like, or both.

As stated above, polymeric carriers will also be suitable in accordance with the invention, see for example the descriptions in WO 95/15815 and U.S. Pat. No. 5,427,991. The methods disclosed may be used with the catalyst complexes, activators or catalyst systems of this invention to adsorb or absorb them on the polymeric supports, particularly if made up of porous particles, or may be chemically bound through functional groups bound to or in the polymer chains.

Useful supports typically have a surface area of from 10-700 $m^2$/g, a pore volume of 0.1-4.0 cc/g and an average particle size of 10-500 μm. Some embodiments select a surface area of 50-500 $m^2$/g, a pore volume of 0.5-3.5 cc/g, or an average particle size of 10-200 μm. Other embodiments select a surface area of 100-400 $m^2$/g, a pore volume of 0.8-3.0 cc/g, and an average particle size of 50-100 μm. Useful supports typically have a pore size of 10-1000 Angstroms, alternatively 50-500 Angstroms, or 75-350 Angstroms.

The catalyst complexes described herein are generally deposited on the support at a loading level of 10-100 micromoles of complex per gram of solid support; alternately 20-80 micromoles of complex per gram of solid support; or 40-60 micromoles of complex per gram of support. But greater or lesser values may be used provided that the total amount of solid complex does not exceed the support's pore volume.

Polymerization

Inventive catalyst complexes are useful in polymerizing unsaturated monomers conventionally known to undergo metallocene-catalyzed polymerization such as solution, slurry, gas-phase, and high-pressure polymerization. Typically one or more of the complexes described herein, one or more activators, and one or more monomers are contacted to produce polymer. In certain embodiments, the complexes may be supported and as such will be particularly useful in the known, fixed-bed, moving-bed, fluid-bed, slurry, solution, or bulk operating modes conducted in single, series, or parallel reactors.

One or more reactors in series or in parallel may be used in the present invention. The complexes, activator and when required, co-activator, may be delivered as a solution or slurry, either separately to the reactor, activated in-line just prior to the reactor, or preactivated and pumped as an activated solution or slurry to the reactor. Polymerizations are carried out in either single reactor operation, in which monomer, comonomers, catalyst/activator/co-activator, optional scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors. In one preferred embodiment, the complex is activated in the reactor in the presence of olefin.

In a particularly preferred embodiment, the polymerization process is a continuous process.

Polymerization processes used herein typically comprise contacting one or more alkene monomers with the complexes (and, optionally, activator) described herein. For purpose of this invention alkenes are defined to include multi-alkenes (such as dialkenes) and alkenes having just one double bond. Polymerization may be homogeneous (solution or bulk polymerization) or heterogeneous (slurry—in a liquid diluent, or gas phase—in a gaseous diluent). In the case of heterogeneous slurry or gas phase polymerization, the complex and activator may be supported. Silica is useful as a support herein. Chain transfer agents may also be used herein.

The present polymerization processes may be conducted under conditions preferably including a temperature of about 30° C. to about 200° C., preferably from 60° C. to 195° C., preferably from 75° C. to 190° C. The process may be conducted at a pressure of from 0.05 MPa to 1500 MPa. In a preferred embodiment, the pressure is between 1.7 MPa and 30 MPa, or in another embodiment, especially under supercritical conditions, the pressure is between 15 MPa and 1500 MPa.

Monomers

Monomers useful herein include olefins having from 2 to 20 carbon atoms, alternately 2 to 12 carbon atoms (preferably ethylene, propylene, butylene, pentene, hexene, heptene, octene, nonene, decene, and dodecene) and, optionally, also polyenes (such as dienes). Particularly preferred monomers include ethylene, and mixtures of $C_2$ to $C_{10}$ alpha olefins, such as ethylene-propylene, ethylene-hexene, ethylene-octene, propylene-hexene, and the like.

The complexes described herein are also particularly effective for the polymerization of ethylene, either alone or in combination with at least one other olefinically unsaturated monomer, such as a $C_3$ to $C_{20}$ α-olefin, and particularly a $C_3$ to $C_{12}$ α-olefin. Likewise, the present complexes are also particularly effective for the polymerization of propylene, either alone or in combination with at least one other olefinically unsaturated monomer, such as ethylene or a $C_4$ to $C_{20}$ α-olefin, and particularly a $C_4$ to $C_{20}$ α-olefin. Examples of preferred α-olefins include ethylene, propylene, butene-1, pentene-1, hexene-1, heptene-1, octene-1, nonene-1, decene-1, dodecene-1, 4-methylpentene-1, 3-methylpentene-1, 3,5,5-trimethylhexene-1, and 5-ethylnonene-1.

In some embodiments, the monomer mixture may also comprise one or more dienes at up to 10 wt %, such as from 0.00001 to 1.0 wt %, for example, from 0.002 to 0.5 wt %, such as from 0.003 to 0.2 wt %, based upon the monomer mixture. Non-limiting examples of useful dienes include, cyclopentadiene, norbornadiene, dicyclopentadiene, 5-ethylidene-2-norbornene ("ENB"), 5-vinyl-2-norbornene, 1,4-hexadiene, 1,5-hexadiene, 1,5-heptadiene, 1,6-heptadiene, 6-methyl-1,6-heptadiene, 1,7-octadiene, 7-methyl-1,7-octadiene, 1,9-decadiene, 1 and 9-methyl-1,9-decadiene.

In a useful embodiment of the invention, the monomers comprise: 1) ethylene; 2) one or more $C_3$ to $C_{12}$ alkenes, such as propylene; and 3) one or more dienes, preferably 5-ethylidene-2-norbornene, 5-vinyl-2-norbornene, 1,5-hexadiene and the like.

Particularly preferred monomers combinations include: ethylene-propylene-ENB, ethylene-hexene-ENB, ethylene-octene-ENB, and the like.

Where olefins are used that give rise to short chain branching, such as propylene, the catalyst systems may, under appropriate conditions, generate stereoregular polymers or polymers having stereoregular sequences in the polymer chains.

Polymer Products

The homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC.

Preferred polymers produced here may be homopolymers or copolymers. In a preferred embodiment, the comonomer(s) are present at up to 50 mol %, preferably from 0.01 to 40 mol %, preferably 1 to 30 mol %, preferably from 5 to 20 mol %. In some embodiments herein, a multimodal polyolefin composition is produced, comprising a first polyolefin component and at least another polyolefin component, different from the first polyolefin component by molecular weight, preferably such that the GPC trace has more than one peak or inflection point.

Unless otherwise indicated, measurements of weight average molecular weight (Mw), number average molecular weight (Mn), and z average molecular weight (Mz) are determined by the GPC-SEC procedure as described below in the Experimental section.

In a preferred embodiment, the homopolymer and copolymer products produced by the present process may have an Mw of about 1,000 to about 2,000,000 g/mol, alternately of about 30,000 to about 600,000 g/mol, or alternately of about 100,000 to about 500,000 g/mol, as determined by GPC-SEC.

In an alternate embodiment, the homopolymer and copolymer products produced by the present process may have a multi-modal, such as bimodal, Mw/Mn.

The term "multimodal," when used to describe a polymer or polymer composition, means "multimodal molecular weight distribution," which is understood to mean that the Gel Permeation Chromatography (GPC-SEC) trace, plotted as Absorbance versus Retention Time (seconds), has more than one peak or inflection point. An "inflection point" is that point where the second derivative of the curve changes in sign (e.g., from negative to positive or vice versa). For example, a polyolefin composition that includes a first lower molecular weight polymer component (such as a polymer having an Mw of 100,000 g/mol) and a second higher molecular weight polymer component (such as a polymer having an Mw of 300,000 g/mol) is considered to be a "bimodal" polyolefin composition.

In an alternate embodiment, the polymer produced herein has an Mw/Mn of from 1 to 40, alternately from greater than 1 to 5.

End Uses

Articles made using polymers produced herein may include, for example, molded articles (such as containers and bottles, e.g., household containers, industrial chemical containers, personal care bottles, medical containers, fuel tanks, and storageware, toys, sheets, pipes, tubing) films, non-wovens, and the like. It should be appreciated that the list of applications above is merely exemplary, and is not intended to be limiting.

EXPERIMENTAL $[H_2CO]_x$ is Paraformaldehyde.

The inventive catalysts below were synthesized according to the following description:

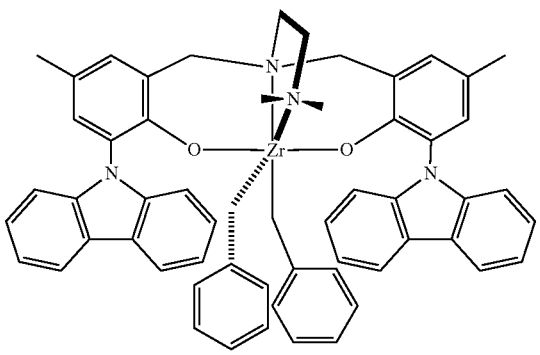

1-Zr

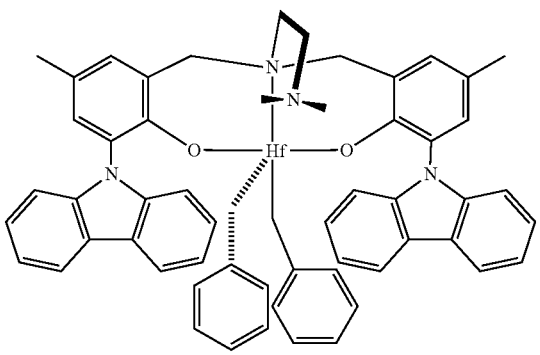

1-Hf

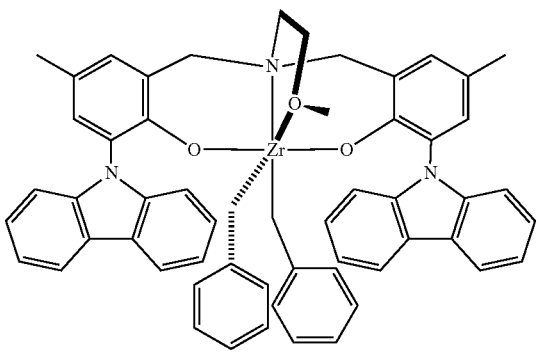

2-Zr

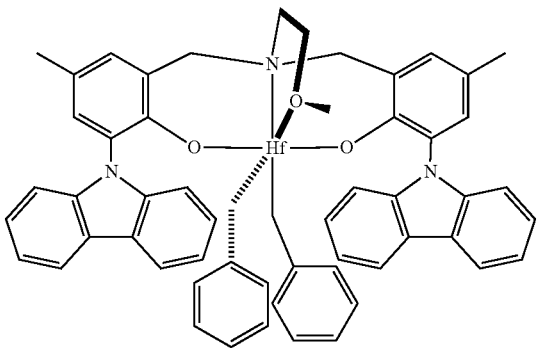

2-Hf

3-Zr
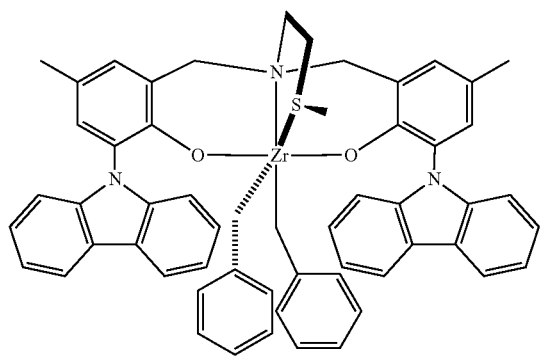
3-Hf
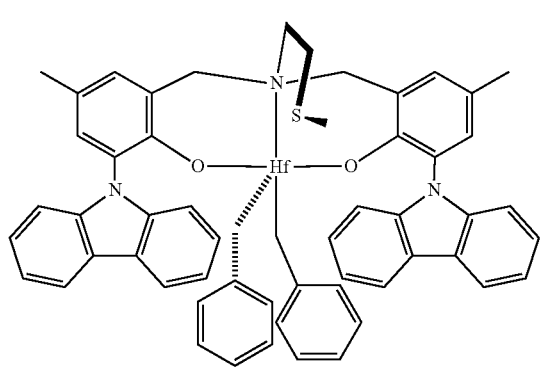
4-Zr
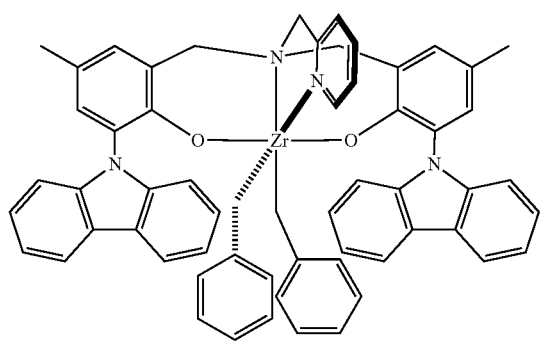
4-Hf
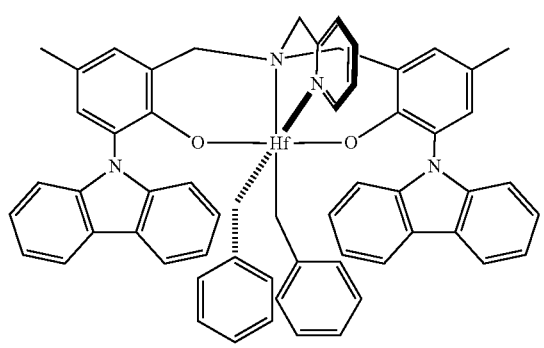
5-Zr
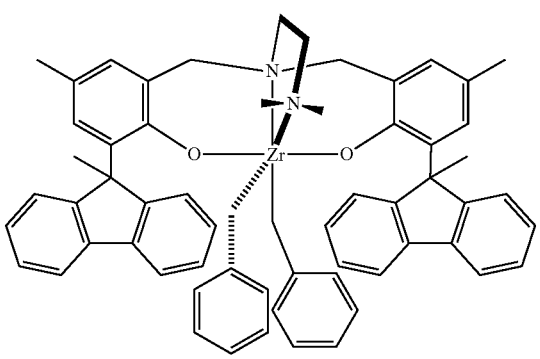
5-Hf
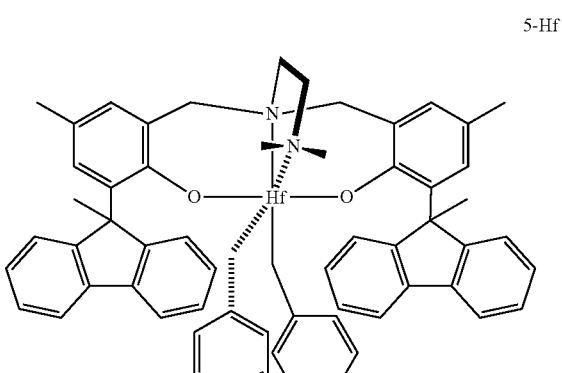
6-Zr
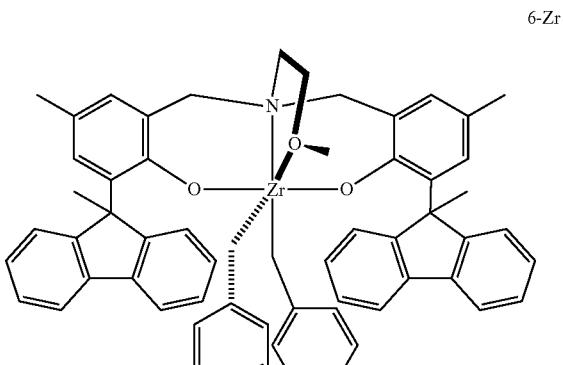
6-Hf
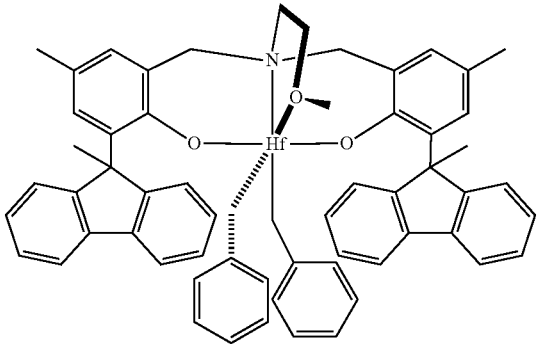

-continued

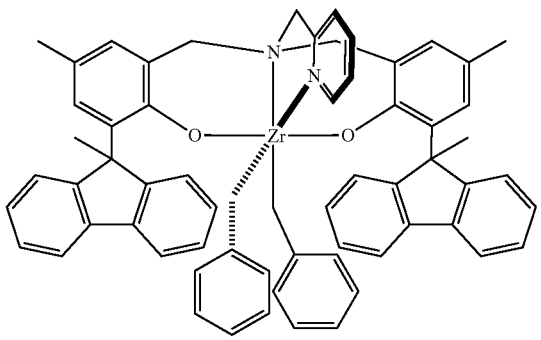

7-Zr

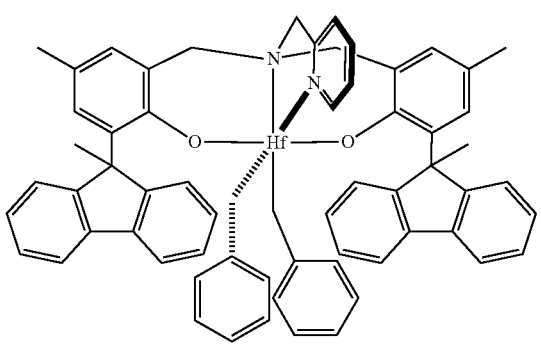

7-Hf

Example 1. 1-Zr and 1-Hf

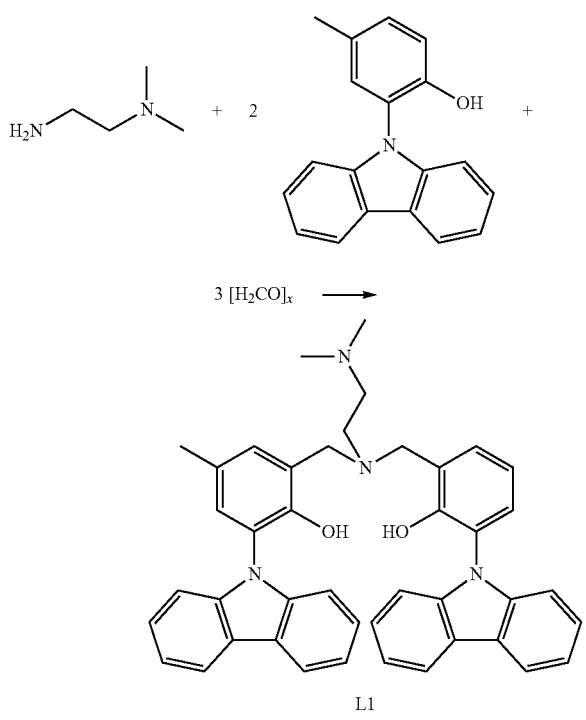

2-(((3-(9H-carbazol-9-yl)-2-hydroxybenzyl)(2-(dimethylamino)ethyl)amino)methyl)-6-(9H-carbazol-9-yl)-4-methylphenol (L1)

A 100 mL round-bottom flask was charged with 2-(9H-carbazol-9-yl)-4-methylphenol (1.004 g, 3.67 mmol, 2 eq), paraformaldehyde (0.164 g, 5.46 mmol, 3 eq), 2-dimethylaminoethanamine (0.162 g, 1.84 mmol, 1 eq) and ethanol (50 mL). The resulting white suspension was stirred at 90° C. for 3 days then cooled to room temperature. Precipitated solids were collected, washed with cold ethanol (2×10 mL), and dried under reduced pressure yielding L1 (0.378 g, 31% yield) as a white powder.

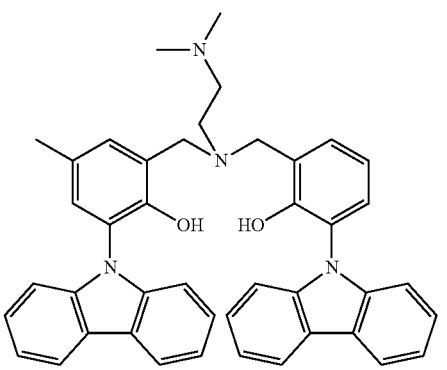

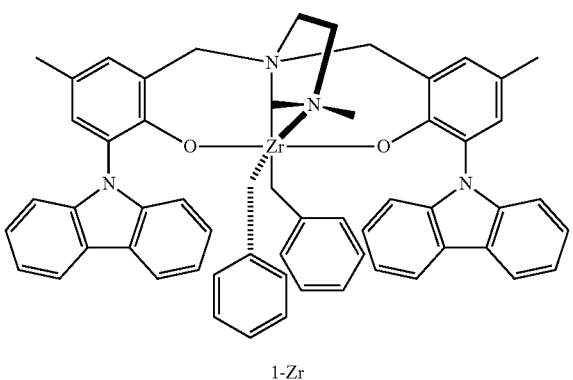

2-dimethylamino-N,N-bis[methylene(4-methyl-2-carbazolylphenolate)]ethanamine zirconium(IV) dibenzyl (1-Zr)

In a glovebox, a 20 mL vial was charged with L1 (0.0788 g, 0.120 mmol, 1 eq), ZrBn$_4$ (0.0550 g, 0.121 mmol, 1 eq) and toluene (2 mL). The resulting yellow solution was stirred at 60° C. for 3.5 hours during which yellow solids precipitated out. The volatiles were removed from the mixture under N$_2$ flow, and the residue was recrystallized in 1:4 toluene:pentane (1 mL) at −35° C. Removal of the supernatant followed by drying under reduced pressure yielded 1-Zr.0.8toluene (0.1052 g, 87%) as a yellow powder. $^1$H NMR (400 MHz, C$_6$D$_6$) δ=8.08 (d, 2H), 8.05 (d, 2H), 7.56 (d, 2H), 7.51 (t, 2H), 7.31 (t, 2H), 6.92-7.27 (13H), 7.86 (t, 2H), 6.78 (t, 1H), 6.68 (d, 2H), 5.23 (d, 2H), 4.00 (d, 2H), 2.63 (d, 2H), 2.10 (s, 6H), 1.98 (m, 2H), 1.27 (m, 2H), 1.22 (s, 2H), 1.08 (s, 2H), 0.89 (s, 6H).

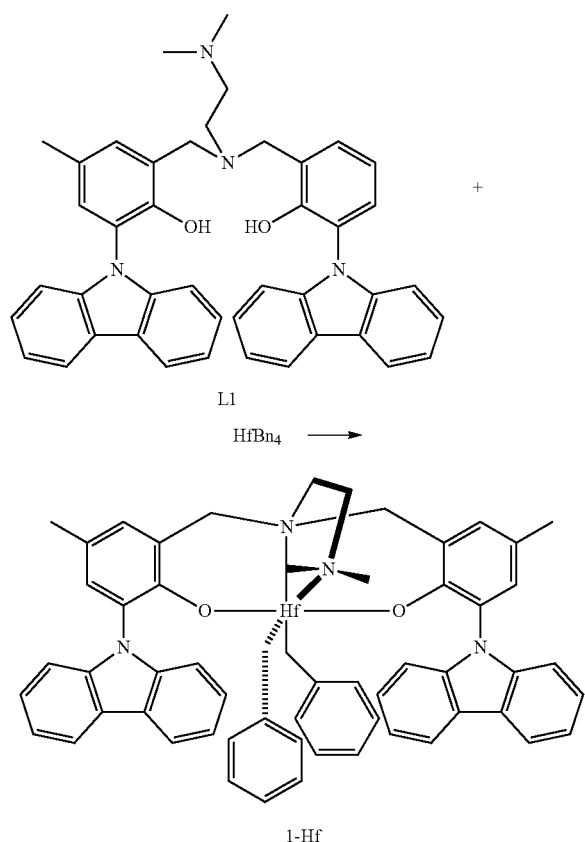

L1

HfBn4 →

1-Hf 2-dimethylamino-N,N-bis[methylene(4-methyl-2-carbazolylphenolate)]ethanamine hafnium(IV) dibenzyl (1-Hf)

This compound was prepared following the procedure for A-Zr using L1 (0.0732 g 0.111 mmol, 1 eq), HfBn4 (0.0610 g, 0.112 mmol, 1 eq) and toluene (2 mL), which yielded 1-Hf.0.7toluene (0.0970 g, 81%) as a white powder. $^1$H NMR (400 MHz, $C_6D_6$) δ=8.13 (dd, 2H), 8.10 (dd, 2H), 7.72 (d, 2H), 7.53 (t, 2H), 7.35 (t, 2H), 6.98-7.28 (13H), 6.82 (t, 2H), 6.73 (t, 1H), 6.65 (d, 2H), 5.36 (d, 2H), 3.87 (d, 2H), 2.60 (d, 2H), 2.12 (s, 6H), 1.90 (s, 2H), 1.81 (br, 2H), 1.15 (br, 2H), 0.90 (s, 2H), 0.68 (s, 6H).

Example 2. 2-Zr and 1-Hf

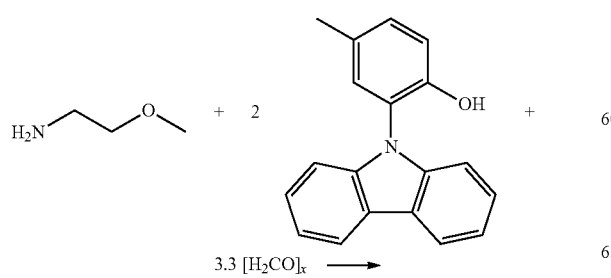

3.3 [H2CO]x →

-continued

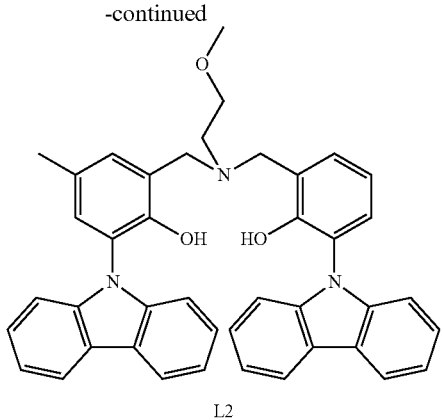

L2

2-(((3-(9H-carbazol-9-yl)-2-hydroxybenzyl)(2-methoxyethy)amino)methyl)-6-(9H-carbazol-9-yl)-4-methylphenol (L2)

A 50 mL round-bottom flask was charged with 2-(9H-carbazol-9-yl)-4-methylphenol (2.078 g, 7.602 mmol, 2 eq), paraformaldehyde (0.383 g, 12.8 mmol, 3.3 eq), 2-methoxyethanamine (0.285 g, 3.79 mmol, 1 eq) and 1:4 water:methanol (10 mL). The resulting white suspension was stirred at 95° C. overnight then cooled to room temperature. The supernatant was decanted, and the crude product was purified over silica gel, eluting with a gradient of 5-30% ethyl acetate in hexane, to give L2 (0.1636 g, 6.7%) as a cream powder.

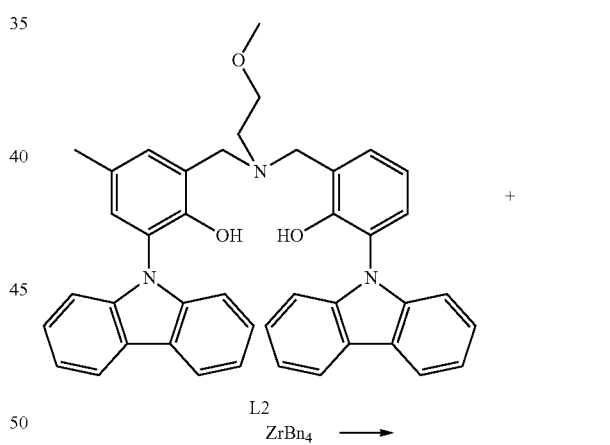

L2

ZrBn4 →

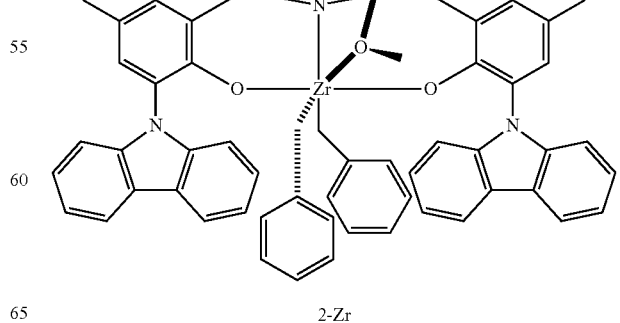

2-Zr

2-methoxy-N,N-bis[methylene(4-methyl-2-carbazolylphenolate)]ethanamine zirconium(IV) dibenzyl (2-Zr)

This compound was prepared following the procedure for A-Zr using L2 (0.0498 g 0.0771 mmol, 1 eq), ZrBn$_4$ (0.0348 g, 0.0764 mmol, 1 eq) and toluene (2 mL), which yielded 2-Zr (0.0606 g, 87%) as a tan powder. $^1$H NMR (400 MHz, C$_6$D$_6$) δ=8.08 (d, 2H), 8.04 (dd, 2H), 7.40-7.45 (3H), 7.28 (m, 2H), 7.10-7.22 (5H), 6.95-7.03 (6H), 6.80 (t, 1H), 6.65-6.75 (5H), 6.57 (t, 2H), 5.07 (d, 2H), 3.83 (d, 2H), 2.63 (d, 2H), 2.40 (t, 2H), 2.14 (s, 9H), 2.04 (t, 2H), 0.91 (s, 2H), 0.86 (s, 2H).

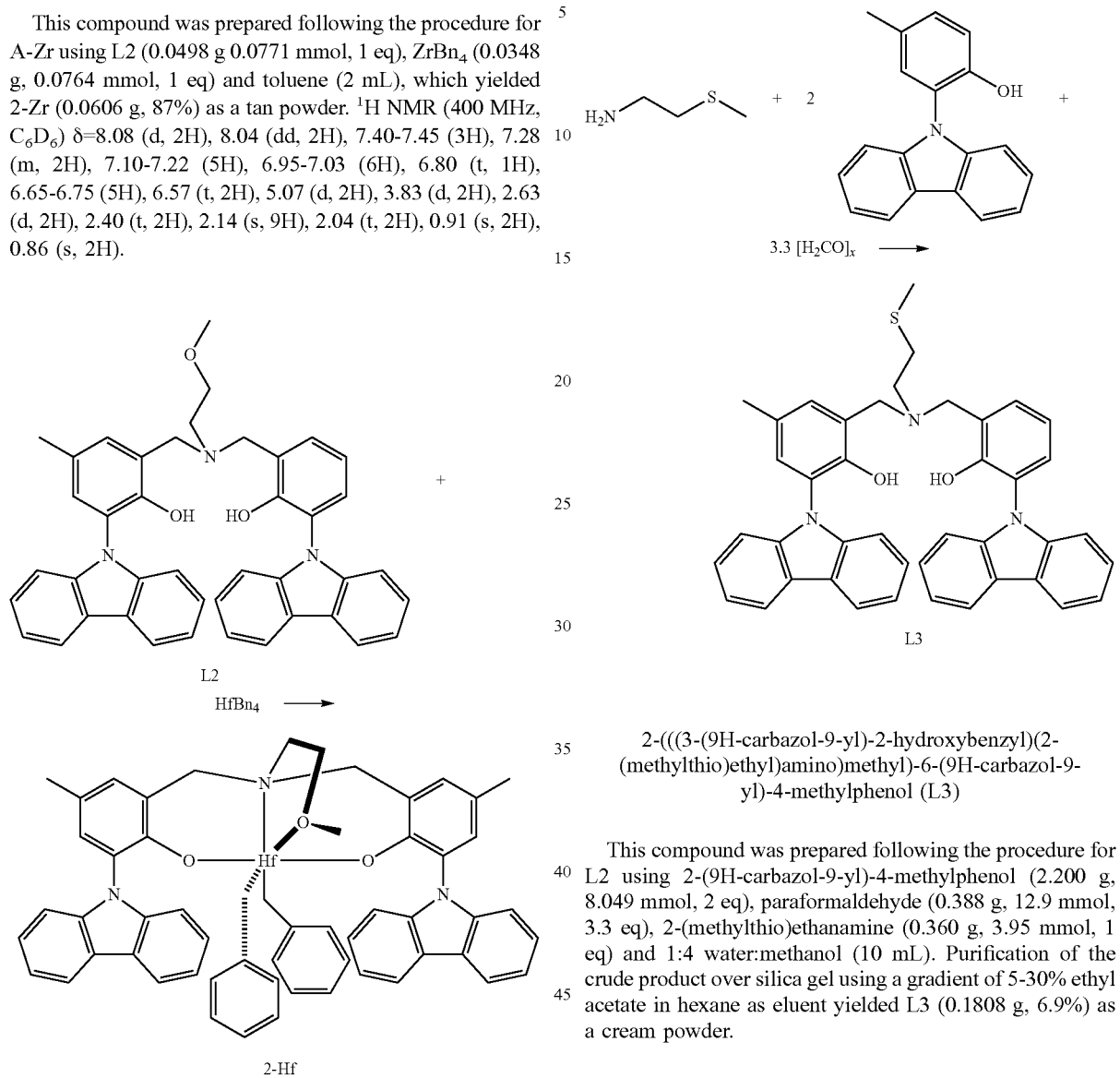

2-methoxy-N,N-bis[methylene(4-methyl-2-carbazolylphenolate)]ethanamine hafnium(IV) dibenzyl (2-Hf)

This compound was prepared following the procedure for A-Zr using L2 (0.0444 g 0.0688 mmol, 1 eq), HfBn$_4$ (0.0386 g, 0.0712 mmol, 1 eq) and toluene (2 mL), which yielded 2-Hf (0.0698 g, quantitative) as a white powder. $^1$H NMR (400 MHz, C$_6$D$_6$) δ=8.13 (d, 2H), 8.08 (m, 2H), 7.62 (d, 2H), 7.48 (t, 2H), 7.32 (t, 2H), 7.14-7.21 (4H), 7.00-7.07 (6H), 6.90 (d, 2H), 6.73 (t, 2H), 6.60-6.65 (4H), 5.35 (d, 2H), 3.62 (d, 2H), 2.59 (d, 2H), 2.30 (t, 2H), 2.14 (s, 6H), 1.88 (s, 3H), 1.83 (t, 2H), 1.57 (s, 2H), 0.76 (s, 2H).

Example 3. 3-Zr and 3-Hf

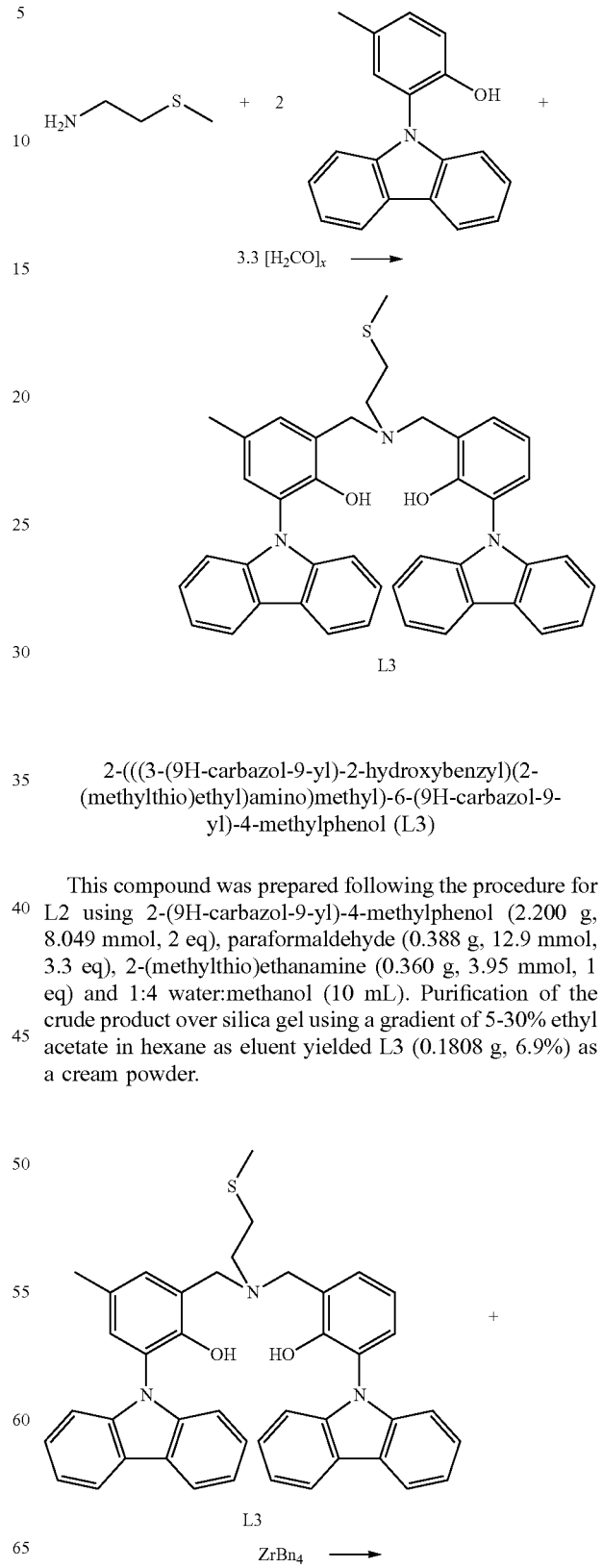

2-(((3-(9H-carbazol-9-yl)-2-hydroxybenzyl)(2-(methylthio)ethyl)amino)methyl)-6-(9H-carbazol-9-yl)-4-methylphenol (L3)

This compound was prepared following the procedure for L2 using 2-(9H-carbazol-9-yl)-4-methylphenol (2.200 g, 8.049 mmol, 2 eq), paraformaldehyde (0.388 g, 12.9 mmol, 3.3 eq), 2-(methylthio)ethanamine (0.360 g, 3.95 mmol, 1 eq) and 1:4 water:methanol (10 mL). Purification of the crude product over silica gel using a gradient of 5-30% ethyl acetate in hexane as eluent yielded L3 (0.1808 g, 6.9%) as a cream powder.

2-methylthio-N,N-bis[methylene(4-methyl-2-carbazolylphenolate)]ethanamine hafnium(IV) dibenzyl (3-Hf)

This compound was prepared following the procedure for A-Zr using L3 (0.0492 g 0.0743 mmol, 1 eq), HfBn₄ (0.0400 g, 0.0737 mmol, 1 eq) and toluene (2 mL), which yielded 3-Hf (0.0620 g, 82%) as a cream powder. ¹H NMR (400 MHz, C₆D₆) δ=8.11 (d, 4H), 7.69 (d, 2H), 7.52 (t, 2H), 7.21-7.32 (7H), 7.10-7.14 (5H), 7.03 (d, 2H), 6.82 (m, 1H), 6.61 (d, 2H), 6.48 (t, 1H), 6.41 (t, 2H), 5.08 (d, 2H), 3.70 (d, 2H), 2.56 (d, 2H), 2.11 (s, 6H), 2.01 (s, 2H), 1.99 (t, 2H), 1.17 (t, 2H), 0.98 (s, 2H), 0.21 (s, 3H).

Example 4. 4-Zr and 4-Hf

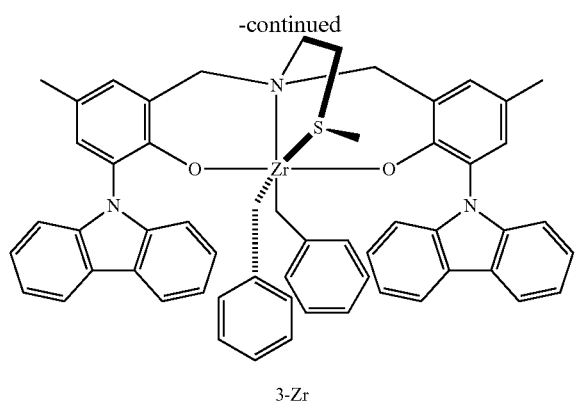

3-Zr

2-methylthio-N,N-bis[methylene(4-methyl-2-carbazolylphenolate)]ethanamine zirconium(IV) dibenzyl (3-Zr)

This compound was prepared following the procedure for A-Zr using L3 (0.0552 g 0.0834 mmol, 1 eq), ZrBn₄ (0.0382 g, 0.0838 mmol, 1 eq) and toluene (2 mL), which yielded 3-Zr (0.0604 g, 77%) as a yellow-brown powder. ¹H NMR (400 MHz, C₆D₆) δ=8.06 (d, 2H), 8.04 (d, 2H), 7.36-7.45 (4H), 7.27 (tt, 4H), 7.20 (dt, 2H), 7.00-7.14 (7H), 6.94 (d, 2H), 6.81 (d, 2H), 6.68 (d, 1H), 6.58 (t, 2H), 4.95 (d, 2H), 4.05 (d, 2H), 2.67 (d, 2H), 2.17 (t, 2H), 2.10 (s, 6H), 1.43 (t, 2H), 1.07 (s, 2H), 0.92 (s, 2H), 0.63 (s, 3H).

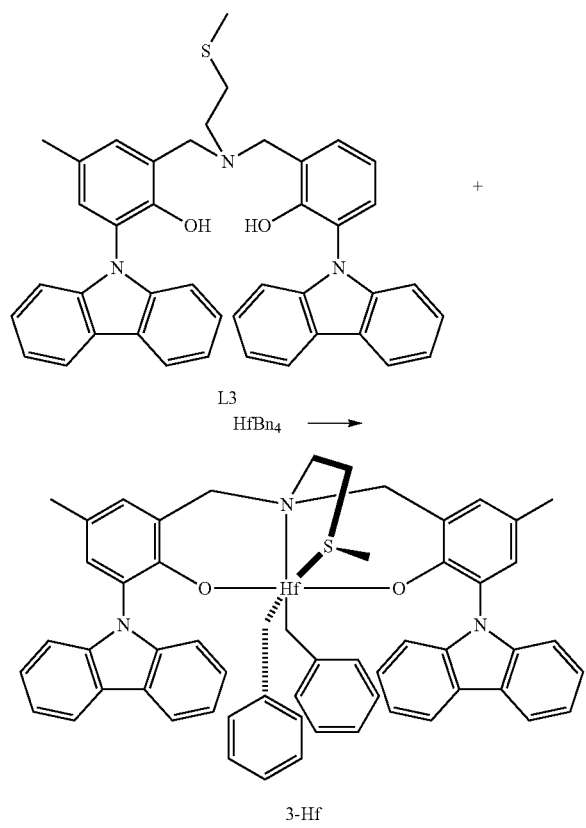

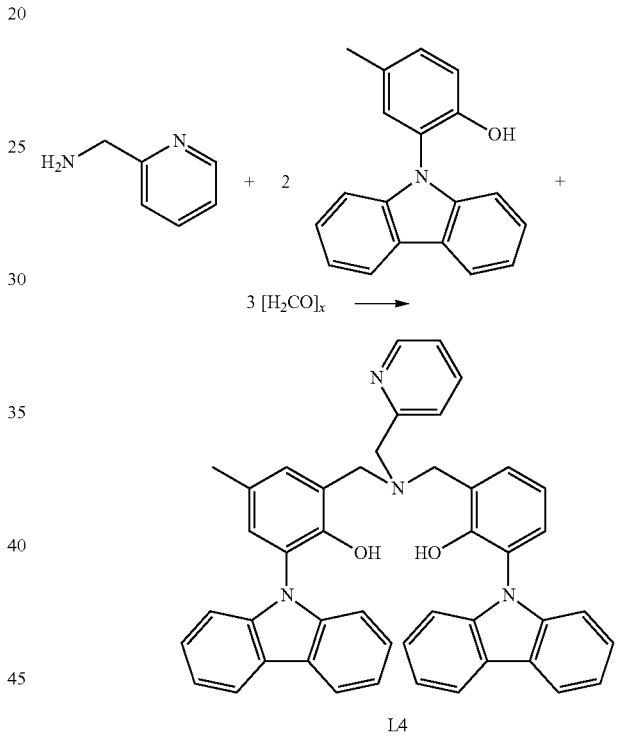

2-(((3-(9H-carbazol-9-yl)-2-hydroxybenzyl)(pyridin-2-ylmethyl)amino)methyl)-6-(9H-carbazol-9-yl)-4-methylphenol (L4)

A 50 mL round bottom flask was charged with 2-(9H-carbazol-9-yl)-4-methylphenol (1.517 g, 5.550 mmol, 2 eq), paraformaldehyde (0.252 g, 8.39 mmol, 3 eq), 2-picolylamine (0.301 g, 2.78 mmol, 1 eq), 0.6 mL water and 3 mL methanol. The resulting white suspension was stirred at 80° C. for 3 days then cooled to room temperature. The supernatant was decanted, and the crude product was purified over silica gel. 50% dichloromethane in hexane was used to elute the unreacted 2-(9H-carbazol-9-yl)-4-methylphenol followed by 30% ethyl acetate in hexane to elute the product. The product fraction was concentrated under reduced pressure to yield L4 (0.778 g, 41%) as a white powder.

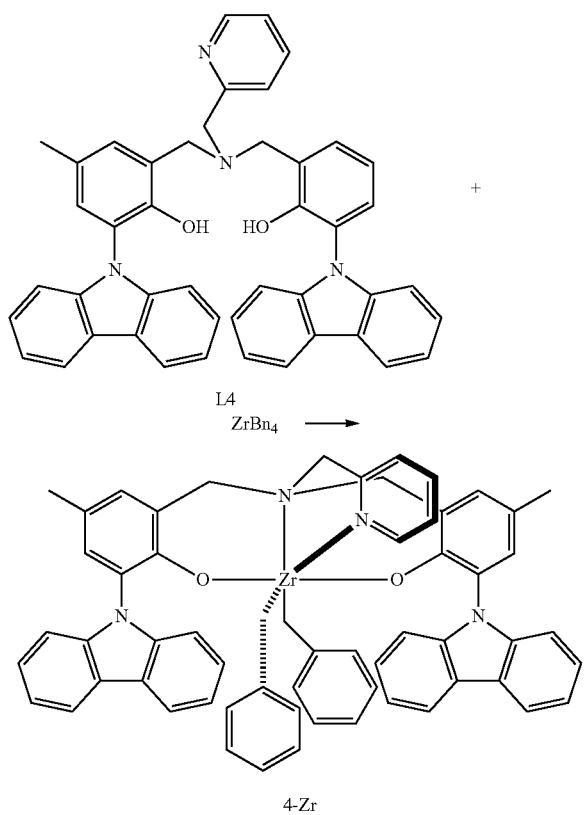

L4

ZrBn₄ ⟶

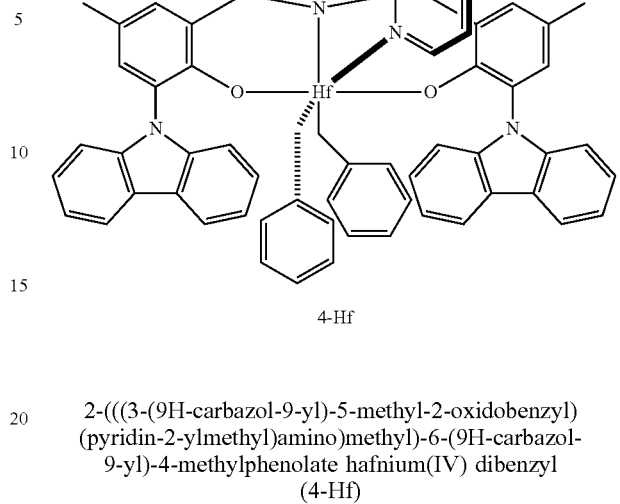

-continued

HfBn₄ ⟶

4-Hf 2-(((3-(9H-carbazol-9-yl)-5-methyl-2-oxidobenzyl)(pyridin-2-ylmethyl)amino)methyl)-6-(9H-carbazol-9-yl)-4-methylphenolate hafnium(IV) dibenzyl (4-Hf)

In a glovebox, a 20 mL vial was charged with L4 (0.1012 g, 0.1491 mmol, 1 eq), HfBn₄ (0.0838 g, 0.154 mmol, 1 eq), and 3 mL toluene. The resulting pale yellow slurry was stirred at 60° C. for 2 h then cooled to room temperature. The volatiles were removed from the mixture under nitrogen flow, and the resulting residue was recrystallized in 3 mL pentane at −35° C. Removal of the supernatant followed by drying under reduced pressure yielded 4-Hf (0.1530 g, quantitative) as a white powder. $^1$H NMR (400 MHz, CD₂Cl₂) δ=8.17 (d, 2H), 8.08 (d, 2H), 7.60 (t, 1H), 7.50 (t, 2H), 7.38 (d, 2H), 7.34 (t, 2H), 7.24 t (2H), 7.08-7.20 (5H), 6.89-6.99 (5H), 6.83 (d, 1H), 6.77 (t, 1H), 6.58 (t, 1H), 6.53 (d, 2H), 6.38 (d, 2H), 6.27 (t, 2H), 5.10 (d, 2H), 3.87 (s, 2H), 3.79 (d, 2H), 3.17 (d, 2H), 2.30 (s, 6H), 0.87 (s, 2H), 0.51 (s, 2H).

4-Zr 2-(((3-(9H-carbazol-9-yl)-5-methyl-2-oxidobenzyl)(pyridin-2-ylmethyl)amino)methyl)-6-(9H-carbazol-9-yl)-4-methylphenolate zirconium(IV) dibenzyl (4-Zr)

In a glovebox, a 20 mL vial was charged with L4 (0.1006 g, 0.1482 mmol, 1 eq), ZrBn₄ (0.0660 g, 0.145 mmol, 1 eq), and 3 mL toluene. The resulting yellow slurry was stirred at 60° C. for 2 h then cooled to room temperature. The volatiles were removed from the mixture under nitrogen flow, and the resulting residue was recrystallized in 3 mL pentane at −35° C. Removal of the supernatant followed by drying under reduced pressure yielded 4-Zr (0.1342 g, 98%) as a yellow powder. $^1$H NMR (400 MHz, CD₂Cl₂) δ=8.14 (d, 2H), 8.06 (d, 2H), 7.60 (t, 1H), 7.48 (t, 2H), 7.31 (t, 2H), 7.07-7.28 (9H), 6.80-6.98 (6H), 6.67 (t, 1H), 6.56 (t, 1H), 6.45 (d, 2H), 6.36 (d, 2H), 6.30 (t, 2H), 4.82 (d, 2H), 3.95 (d, 2H), 3.93 (s, 2H), 3.14 (d, 2H), 2.29 (s, 6H), 0.66 (s, 2H), 0.31 (s, 2H).

Example 5. 5-Zr and 5-Hf

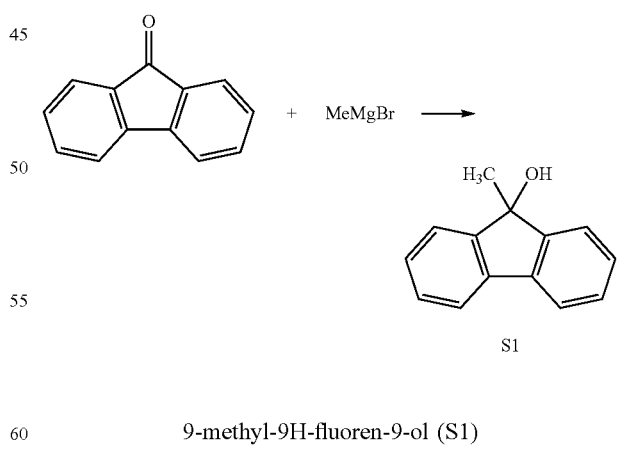

S1

9-methyl-9H-fluoren-9-ol (S1)

In a glovebox, a 250 mL round-bottom flask was charged with 9H-fluoren-9-one (10.300 g, 57.2 mmol, 1.0 eq) and THF (80 mL), and the resulting solution was cooled to 0° C. MeMgBr (20.0 mL of a 3.0 M solution, 0.6 mmol, 1.05 eq) was then slowly added using a syringe to the stirring solution, which turned into a slurry at the end of the addition.

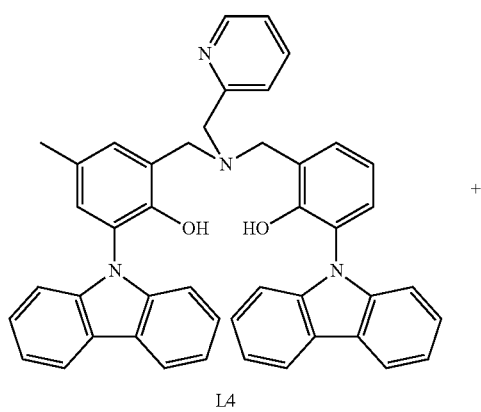

L4

The mixture was warmed to room temperature and allowed to stir for 16 hours. The reaction vessel was then removed from the glovebox, and the reaction mixture was poured into a saturated solution of NH₄Cl (200 mL) and washed with brine (100 mL×2). The organic portion was collected, dried over MgSO₄, filtered and concentrated under a nitrogen stream. The crude product was recrystallized in pentane (200 mL) yielding S1 (10.077 g, 90%) as a white powder. Alternatively, L5a can be purified on a Biotage™ silica column with a gradient of 5-20% ethyl acetate in hexane.

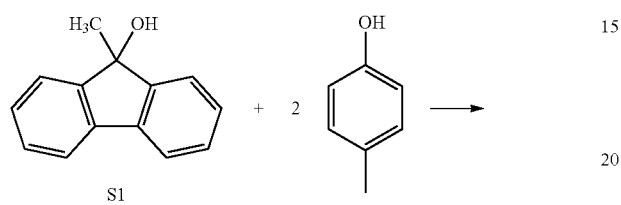

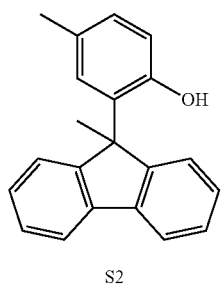

4-methyl-2-(9-methyl-9H-fluoren-9-yl)phenol (S1)

In a 500 mL round-bottom flask, p-cresol (7.8 g, 72 mmol, 2 eq) was dissolved in DCM (200 mL) followed by slow addition of concentrated sulfuric acid (3.916 g, 37.93 mmol, 1 eq). A solution of S1 (7.403 g, 37.72 mmol, 1 eq) in DCM (150 mL) was then added to the flask using an addition funnel, and the resulting yellow solution was stirred for 3 hours at room temperature during which the color turned green. The reaction was basified with 2M NaOH to pH 9-10. The organic layer was collected, washed with brine, dried with MgSO₄ and concentrated under a nitrogen stream. The crude product was purified over a Biotage™ silica column using a gradient of 5-20% DCM in hexane, which yielded S2 (8.437 g, 78%) as a white crystalline powder.

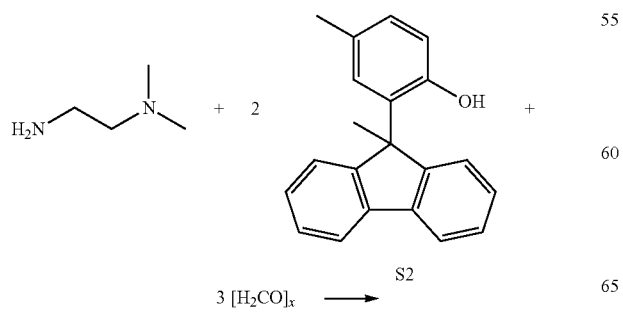

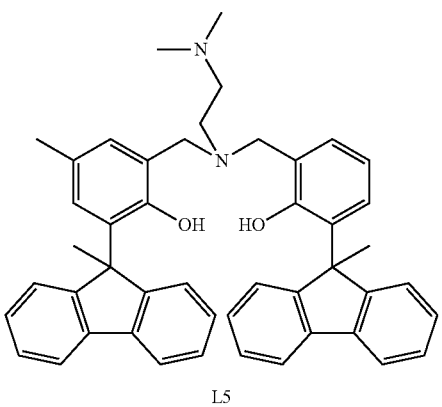

2-(((2-(dimethylamino)ethyl)(2-hydroxy-3-(9-methyl-9H-fluoren-9-yl)benzyl)amino)methyl)-4-methyl-6-(9-methyl-9H-fluoren-9-yl)phenol (L5)

A 50 mL round-bottom flask was charged with S2 (0.755 g, 2.64 mmol, 2 eq), paraformaldehyde (0.109 g, 3.63 mmol, 3 eq), LiCl (0.122 g, 2.88 mmol, 2 eq), 2-dimethylaminoethanamine (0.117 g, 1.33 mmol, 1 eq) and ethanol (4 mL). The resulting white slurry was stirred at 80° C. for 3 days then cooled to room temperature. The supernatant was decanted, and the crude product was purified over silica gel, eluting with a gradient of 0-20% ethyl acetate in hexane, to give L5 (0.696 g, 77%) as a white powder.

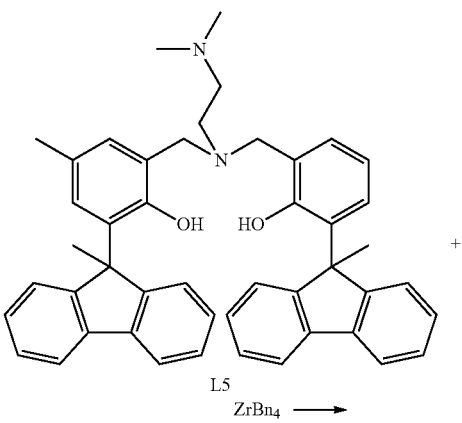

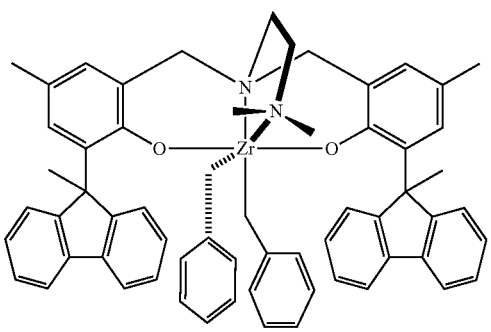

2-dimethylamino-N,N-bis[methylene(4-methyl-2-(9-methyl-9H-fluoren-9-yl)phenolate)]ethanamine zirconium(IV) dibenzyl (5-Zr)

In a glovebox, a 20 mL vial was charged with L5 (0.1708 g, 0.2494 mmol, 1 eq), ZrBn$_4$ (0.1130 g, 0.2480 mmol, 1 eq), and 3 mL toluene. The resulting orange solution was stirred at 60° C. for 3 h then cooled to room temperature. The volatiles were removed from the mixture under nitrogen flow, and the resulting residue was recrystallized in 2 mL pentane at −35° C. Removal of the supernatant followed by drying under reduced pressure yielded 5-Zr (0.2304 g, 97%) as a pale yellow powder. $^1$H NMR (400 MHz, CD$_2$Cl$_2$)— broad and overlapping resonances; δ=8.37, 7.77, 7.42, 7.32, 7.24, 7.18, 6.81, 6.65, 6.55, 3.13, 2.73, 2.38, 1.91.

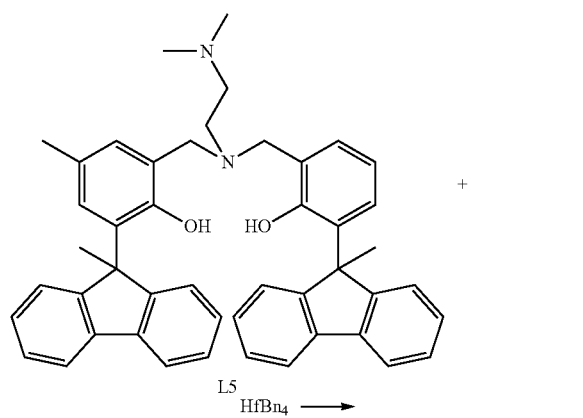

2-dimethylamino-N,N-bis[methylene(4-methyl-2-(9-methyl-9H-fluoren-9-yl)phenolate)]ethanamine hafnium(IV) dibenzyl (5-Hf)

In a glovebox, a 20 mL vial was charged with L5 (0.1867 g, 0.2726 mmol, 1 eq), HfBn$_4$ (0.1508 g, 0.2777 mmol, 1 eq), and 3 mL toluene. The resulting yellow solution was stirred at 60° C. for 2 h then cooled to room temperature. The volatiles were removed from the mixture under nitrogen flow, and the resulting residue was recrystallized in 1 mL pentane at −35° C. Removal of the supernatant followed by drying under reduced pressure yielded 5-Hf (0.2756 g, 92%) as a very light tan powder. $^1$H NMR (400 MHz, CD$_2$Cl$_2$)— broad and overlapping resonances; δ=8.31, 7.81, 7.43, 7.32, 7.24, 7.22, 7.18, 7.16, 6.85, 6.83, 6.65, 6.54, 3.25, 3.09, 2.78, 3.42, 2.23, 2.08, 1.86, 1.73, 1.49.

Example 6. 6-Zr and 6-Hf

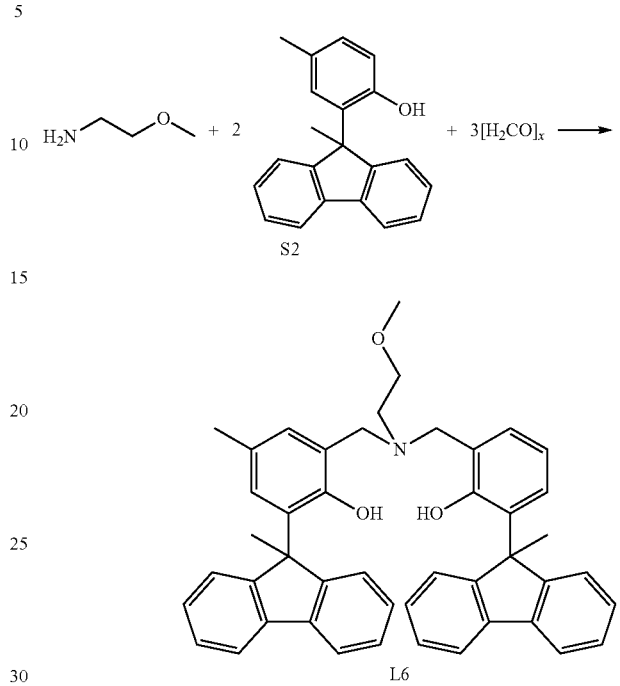

2-(((2-hydroxy-3-(9-methyl-9H-fluoren-9-yl)benzyl)(2-methoxyethy)amino)methyl)-4-methyl-6-(9-methyl-9H-fluoren-9-yl)phenol (L6)

A 50 mL round bottom flask was charged with S2 (0.696 g, 2.43 mmol, 2 eq), paraformaldehyde (0.116 g, 3.86 mmol, 3 eq), 2-methoxyethanamine (0.091 g, 1.21 mmol, 1 eq), 0.6 mL water and 3 mL methanol. The resulting white suspension was stirred at 80° C. overnight then cooled to room temperature. The supernatant was decanted, and the crude product was purified over a Biotage silica column using a gradient of 0-30% ethyl acetate in hexane, which yielded L6 (0.262 g, 32%) as a white powder.

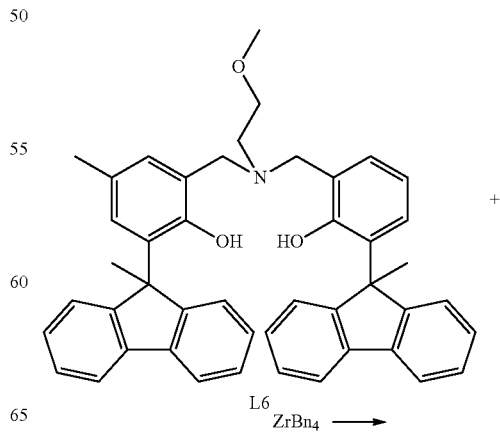

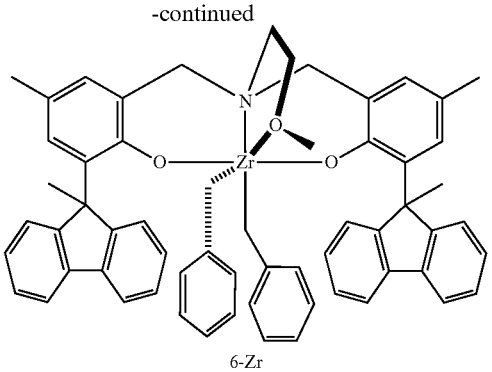

6-Zr 2-methoxy-N,N-bis[methylene(4-methyl-2-(9-methyl-9H-fluoren-9-yl)phenolate)]ethanamine zirconium(IV) dibenzyl (6-Zr)

In a glovebox, a 20 mL vial was charged with L6 (0.262 g, 0.373 mmol, 1 eq), ZrBn$_4$ (0.1704 g, 0.3739 mmol, 1 eq), and 3 mL toluene. The resulting orange solution was stirred at 60° C. for 3 h then cooled to room temperature. The volatiles were removed from the mixture under nitrogen flow, and the resulting residue was recrystallized in 2 mL pentane at −35° C. Removal of the supernatant followed by drying under reduced pressure yielded 6-Zr (0.3566 g, quantitative) as a pale yellow powder. $^1$H NMR (400 MHz, CD$_2$Cl$_2$)— broad and overlapping resonances; δ=7.87, 7.79, 7.77, 7.51, 7.43, 7.34, 7.28, 7.18, 6.84, 6.66, 6.61, 3.19, 3.07, 2.83, 2.80, 2.46, 2.00.

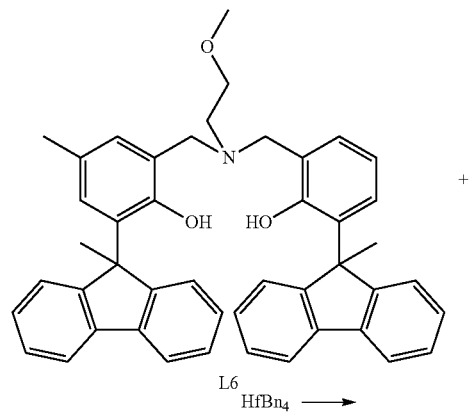

L6

HfBn$_4$ ⟶

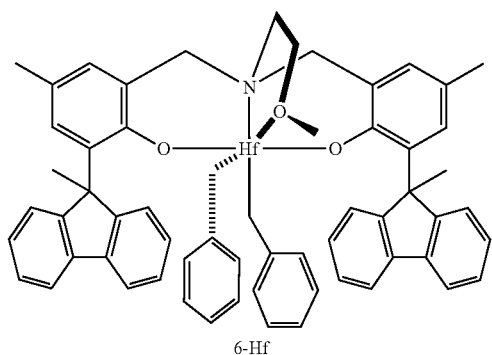

6-Hf 2-methoxy-N,N-bis[methylene(4-methyl-2-(9-methyl-9H-fluoren-9-yl)phenolate)]ethanamine hafnium(IV) dibenzyl (6-Hf)

In a glovebox, a 20 mL vial was charged with L6 (0.201 g, 0.299 mmol, 1 eq), HfBn$_4$ (0.1614 g, 0.2972 mmol, 1 eq), and 3 mL toluene. The resulting pale yellow solution was stirred at 60° C. for 2.5 h then cooled to room temperature. The volatiles were removed from the mixture under nitrogen flow, and the resulting residue was recrystallized in 2 mL pentane at −35° C. Removal of the supernatant followed by drying under reduced pressure yielded 6-Hf (0.2958 g, quantitative) as a white powder. $^1$H NMR (400 MHz, CD$_2$Cl$_2$)— broad and overlapping resonances; δ=7.84, 7.76, 7.48, 7.34, 7.26, 7.18, 6.89, 6.81, 6.64, 6.59, 6.53, 3.26, 3.09, 2.87, 2.83, 2.44, 1.90.

Example 7. 7-Zr and 7-Hf

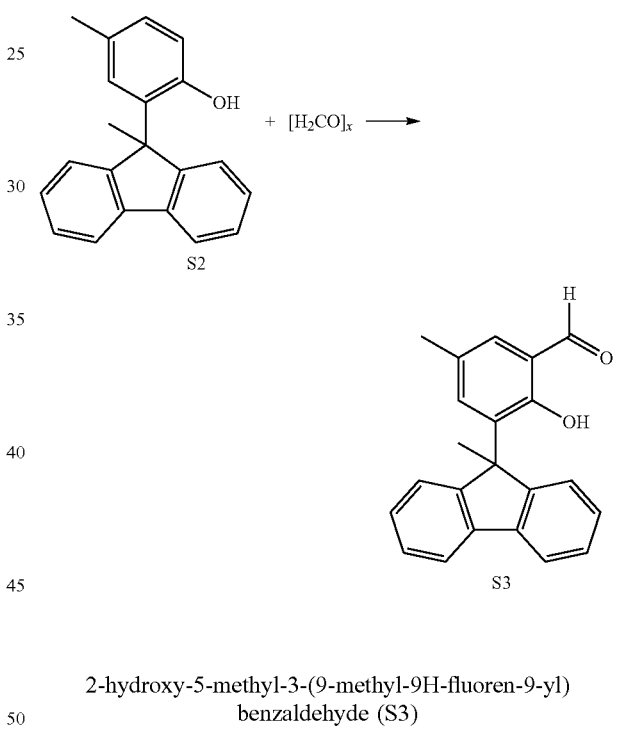

2-hydroxy-5-methyl-3-(9-methyl-9H-fluoren-9-yl) benzaldehyde (S3)

In a glovebox, S2 (5.346 g, 18.7 mmol, 1.0 eq), paraformaldehyde (3.364 g, 112.0 mmol, 6 eq), Et$_3$N (5.667 g, 56.0 mmol, 3 eq), and MgCl$_2$ (4.443 g, 46.5 mmol, 2.5 eq) were slurried in 150 mL of CH$_3$CN and stirred for 2 hours upon which the slurry became yellow. The reaction flask was then cooled to −35° C. and DMF (6.822 g, 93.3 mmol, 5 eq) was added. The reaction was allowed to warm to room temp and stirred for 16 hours. The reaction flask was removed from the glovebox and the contents poured into 250 mL of 1M HCl, where the yellow slurry immediately turned white. The slurry was extracted with EtOAc (200 mL). The organics were washed with brine (100 mL×2), collected, dried with MgSO4, filtered through a frit and concentrated. The resulting residue was purified on a silica column using a 0-20% EtOAc/Hexane gradient to yield S3 (4.85 g, 82%).

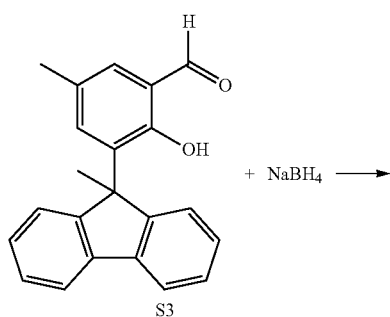

2-(bromomethyl)-4-methyl-6-(9-methyl-9H-fluoren-9-yl)phenol (S5).)

In a glovebox, S4 (2.123 g, 6.71 mmol, 1 eq) was dissolved in 40 mL of CH$_2$Cl$_2$. Separately, PBr$_3$ (0.908 g, 3.35 mmol, 0.5 eq) was dissolved in 10 mL of CH$_2$Cl$_2$ then added to a stirring solution of S4. After one hour, the reaction flask was removed from the glovebox and cold water (20 mL) was added to quench the reaction. The organics were separated, dried with MgSO$_4$, filtered through a frit, and concentrated to yield S5 (2.257 g, 88.7%). No further purification was performed.

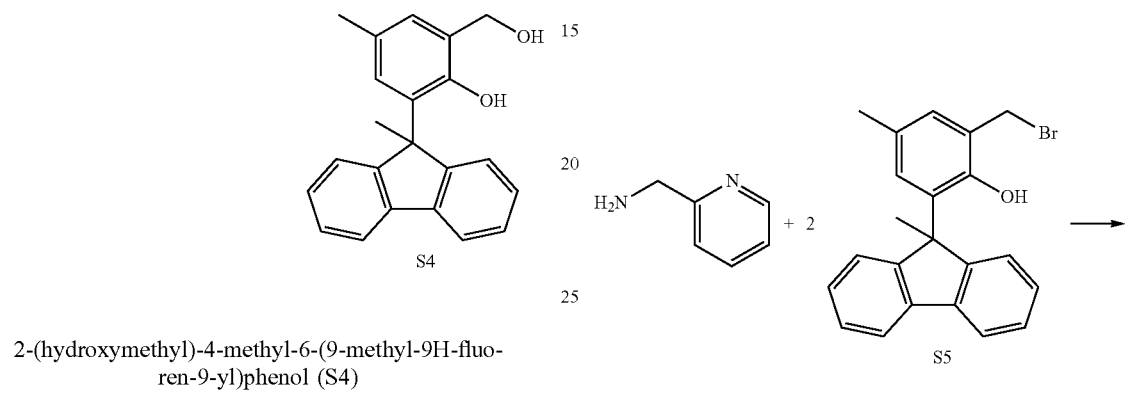

2-(hydroxymethyl)-4-methyl-6-(9-methyl-9H-fluoren-9-yl)phenol (S4)

In a 250 mL round bottom flask, S3 (4.711 g, 15.0 mmol, 1.0 eq) was dissolved in 80 mL of MeOH. NaBH$_4$ (1.134, 30.0 mmol, 2 eq) was added slowly as a powder. Vigorous bubbling was observed along with a change to an almost colorless solution. Reaction was allowed to stir for 16 hours. Solvent was removed and the residue was extracted with CH$_2$Cl$_2$ (100 mL). The organics were washed with water (50 mL×2) and brine (50 mL×2). The organics were then collected, dried with MgSO$_4$, filtered through a frit, and the solvent removed to give a white solid. The crude product was purified on a silica column with a 0-2% MeOH/CH$_2$Cl$_2$ gradient to give S4 (3.638 g, 77%).

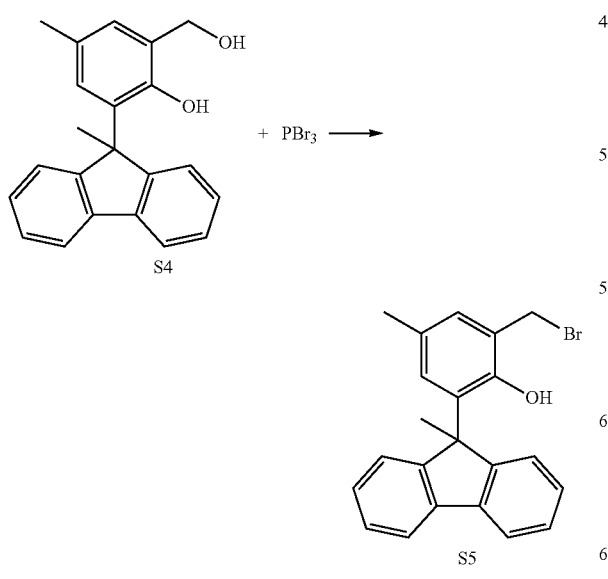

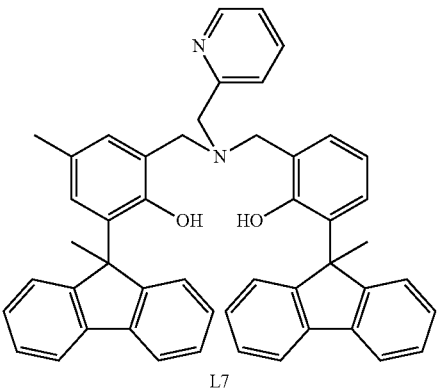

2-(((2-hydroxy-3-(9-methyl-9H-fluoren-9-yl)benzyl)(pyridin-2-ylmethyl)amino)methyl)-4-methyl-6-(9-methyl-9H-fluoren-9-yl)phenol (L7)

In a 20 mL vial, S5 (0.383 g, 1.01 mmol, 2 eq) and 2-picolylamine (0.052 mL, 0.50 mmol, 1 eq) were dissolved in 10 mL of THF. An immediate precipitate was observed. Et$_3$N was added (0.141, 1.21 mmol, 1.2 eq), and the reaction was stirred for 2 hours. The solvent was removed, and the residue was extracted with Et$_2$O. The extract was washed with water (5 mL×2) and brine (5 mL), collected, dried with MgSO$_4$, filtered, and concentrated. The resulting residue was purified using two different solvent gradients through a silica column: a) 40-60% CH$_2$Cl$_2$/hexane collecting the main fraction, then b) 5-20% EtOAc/Hexane. The yield of the purified product, L7, was 0.126 g (18%).

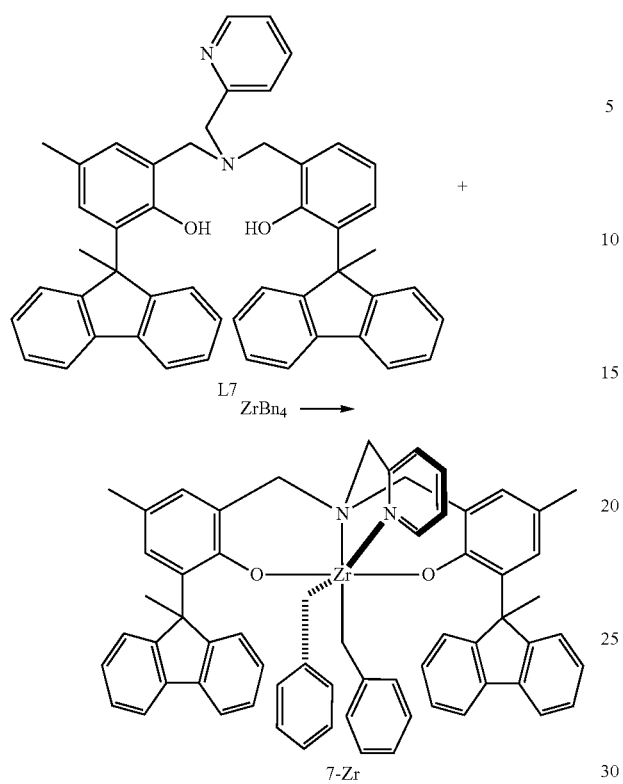

L7
ZrBn4 →

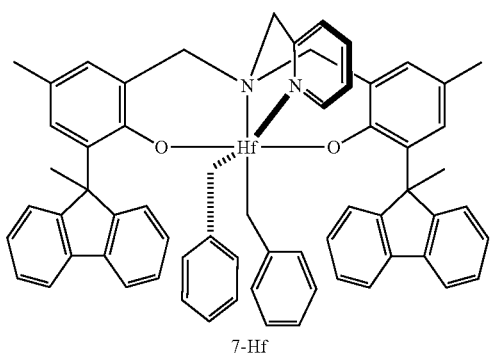

7-Hf 6,6'-(((pyridin-2-ylmethyl)azanediyl)bis(methylene))bis(4-methyl-2-(9-methyl-9H-fluoren-9-yl)phenolate) hafnium(IV) dibenzyl (6-Hf)

In a glovebox, a 20 mL vial was charged with L7 (0.082 g, 0.116 mmol, 1 eq), HfBn4 (0.063 g, 0.116 mmol, 1 eq), and 10 mL toluene. The resulting pale yellow solution was stirred at 50° C. for 1 h then cooled to room temperature. The volatiles were removed from the mixture under nitrogen flow, and the resulting residue was recrystallized in 2 mL pentane at −35° C. Removal of the supernatant followed by drying under reduced pressure yielded 7-Hf (0.065 g, 53%) as a white powder. $^1$H NMR (400 MHz, CD$_2$Cl$_2$)— broad and overlapping resonances; δ=7.78, 7.54, 7.33, 7.24, 7.18, 7.16, 6.93, 6.91, 6.65, 3.64, 2.96, 2.93, 1.92.

7-Zr 6,6'-(((pyridin-2-ylmethyl)azanediyl)bis(methylene))bis(4-methyl-2-(9-methyl-9H-fluoren-9-yl)phenolate) zirconium(IV) dibenzyl (7-Zr).)

In a glovebox, a 20 mL vial was charged with L7 (0.126 g, 0.179 mmol, 1 eq), ZrBn4 (0.081 g, 0.179 mmol, 1 eq), and 10 mL toluene. The resulting orange solution was stirred at 50° C. for 1 h then cooled to room temperature. The volatiles were removed from the mixture under nitrogen flow, and the resulting residue was recrystallized in 2 mL pentane at −35° C. Removal of the supernatant followed by drying under reduced pressure yielded 7-Zr (0.139 g, 79%) as a yellow powder. $^1$H NMR (400 MHz, CD$_2$Cl$_2$)— broad and overlapping resonances; δ=7.77, 7.49, 7.32, 7.24, 7.22, 7.18, 7.16, 7.14, 6.94, 6.84, 6.67, 6.57, 3.57, 2.90, 2.87, 1.96.

Example 8. 8-Zr, 8-Hf, 9-Zr and 9-Hf

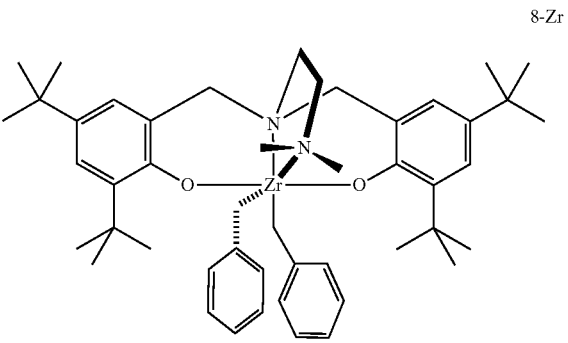

8-Zr

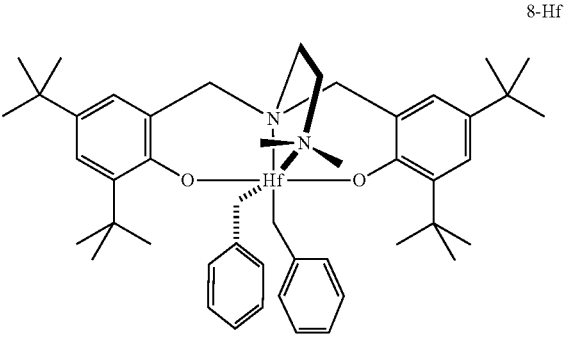

8-Hf

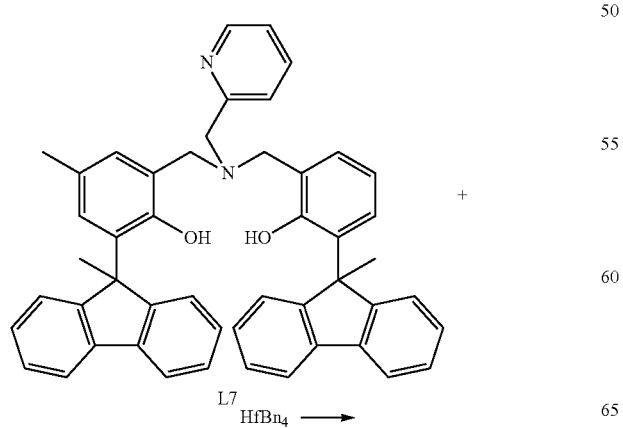

L7
HfBn4 →

-continued

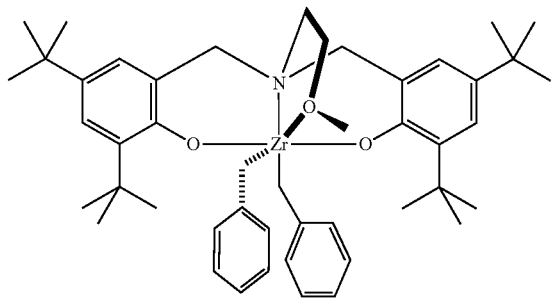

9-Zr

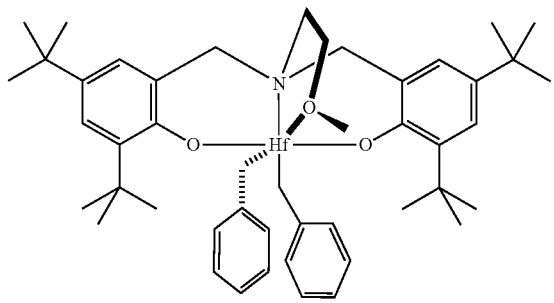

9-Hf

Compounds 8-Zr, 8-Hf, 9-Zr and 9-Hf were prepared following the procedures described in Organometallics, 2001, 20, 3017-3028 and Organometallics, 2002, 21, 662-670. These compounds were also evaluated for comparison with the inventive catalysts.

Example 9. Polymerization Examples

General Polymerization Procedures for Parallel Pressure Reactor

Ethylene-octene, ethylene-ENB and ethylene-propylene copolymerizations were carried out in a parallel, pressure reactor, as generally described in U.S. Pat. No. 6,306,658; U.S. Pat. No. 6,455,316; U.S. Pat. No. 6,489,168; WO 00/09255; and Murphy et al., J. Am. Chem. Soc., 2003, 125, pp. 4306-4317, each of which is fully incorporated herein by reference. Although the specific quantities, temperatures, solvents, reactants, reactant ratios, pressures, and other variables are frequently changed from one polymerization run to the next, the following describes a typical polymerization performed in a parallel, pressure reactor.

A pre-weighed glass vial insert and disposable stirring paddle were fitted to each reaction vessel of the reactor, which contains 48 individual reaction vessels. The reactor was then closed and each vessel was charged with enough solvent (typically toluene or isohexane) to bring the total reaction volume, including the subsequent additions, to the desired volume, typically 5 mL. The reactor was heated to the set temperature and pressurized to the predetermined pressure of ethylene. 1-octene or 5-ethylidene-2-norbornene (ENB), if required, was injected into each reaction vessel through a valve and the aluminum and/or zinc compound in toluene was added to act as a scavenger and/or chain transfer agent.

For ethylene-propylene copolymerizations, propylene was introduced to each vessel as a condensed gas after charging the reactor vessels with the required amount of solvent. The reactor vessels were then heated to the set temperature and pressurized with the required amount of ethylene, followed by addition of TNOAL as the scavenger and/or chain transfer agent.

The contents of the vessel were stirred at 800 rpm. An activator solution (typically 1.0-1.2 molar equivalents of N,N-dimethyl anilinium tetrakis-pentafluorophenyl borate (Activator-1) dissolved in toluene or 100-1000 molar equivalents of methyl alumoxane (MAO) in toluene was then injected into the reaction vessel along with 500 microliters of toluene, followed by a toluene solution of catalyst (typically 0.40 mM in toluene, usually 20-80 nanomols of catalyst) and another aliquot of toluene (300 microliters). Equivalence is determined based on the mol equivalents relative to the moles of the transition metal in the catalyst complex.

The reaction was then allowed to proceed until a predetermined amount of pressure (quench value) had been taken up by the reaction. Alternatively, the reaction may be allowed to proceed for a set amount of time (maximum reaction time). At this point, the reaction was quenched by pressurizing the vessel with compressed air or 50/50 $CO_2$/Argon. After the polymerization reaction, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight, by FT-IR (see below) to determine percent ethylene incorporation, and by DSC (see below) to determine melting point.

To determine various molecular weight related values by GPC, high temperature size exclusion chromatography was performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and 6,294,388; each of which is fully incorporated herein by reference for US purposes. This apparatus has a series of three 30 cm×7.5 mm linear columns, each containing PLgel 10 μm, Mix B. The GPC system was calibrated using polystyrene standards ranging from 580-3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.28 mg/mL and 400 μL of a polymer solution was injected into the system. The concentration of the polymer in the eluent was monitored using an evaporative light scattering detector. The molecular weights presented are relative to linear polystyrene standards and are uncorrected, unless indicated otherwise.

Differential Scanning Calorimetry (DSC) measurements were performed on a TA-Q100 instrument to determine the melting point of the polymers. Samples were pre-annealed at 220° C. for 15 minutes and then allowed to cool to room temperature overnight. The samples were then heated to 220° C. at a rate of 100° C./min and then cooled at a rate of 50° C./min Melting points were collected during the heating period.

The weight percent of ethylene incorporated in polymers was determined by rapid FT-IR spectroscopy on a Bruker Equinox 55+IR in reflection mode. Samples were prepared in a thin film format by evaporative deposition techniques. Weight percent comonomer was obtained from the ratio of peak heights at 1378 and 4322 $cm^{-1}$ for ethylene-octene copolymers and 1681-1690 and 2010-2020 cm$^{-1}$ for ethylene-ENB copolymers. FT-IR methods were calibrated using a set of samples with a range of known wt % ethylene content. For ethylene-propylene copolymers, weight percent propylene was determined by $^1$H NMR spectroscopy.

$^1$H NMR data were collected at 120° C. in a 5 mm probe using a spectrometer with a $^1$H frequency of 500 MHz. Data was recorded using a maximum pulse width of 45°, 5 seconds between pulses and signal averaging 120 transients. Spectral signals were integrated. Samples were dissolved in deuterated 1,1,2,2,-tetrachloroethane at concentrations of 1-2 wt % prior to being inserted into the spectrometer magnet. Prior to data analysis, spectra were referenced by setting the residual hydrogen-containing solvent resonance to 5.98 ppm.

Entries 1 to 4 and 17 to 22 show that the inventive catalysts exhibited higher activities compared with the reference catalysts (entries 27 to 33). Entries 1 to 4 and 17 to 26 show that the inventive catalysts had higher polymer molecular weight capability compared with the reference catalysts of the same metal (entries 27 to 31). Entries 1 to 4 show that the inventive catalysts incorporate more 1-octene than the reference catalysts (entries 27 to 31). (Runs 1 and 2 are duplicate experiments.)

TABLE 1

Reaction conditions for ethylene-octene (EO) copolymerization with Activator-1.

| | |
|---|---|
| Catalyst loading | 0.020 μmol |
| Activator-1 | 0.022 μmol (1.1 eq) |
| Temperature | 100° C. |
| Ethylene Pressure | 135 psi |
| 1-Octene | 100 μL |
| Total Volume | 5 mL |
| Solvent | Isohexane |
| Aluminum compound | 1 μmol TNOAL |
| Quench Value | 20 psi |
| Maximum Reaction Time | 30 min |

TABLE 3

Reaction conditions for ethylene-octene (EO) copolymerization with MAO.

| | |
|---|---|
| Catalyst loading | 0.020 μmol |
| MAO | 10 μmol (500 eq) |
| Temperature | 100° C. |
| Ethylene Pressure | 120 or 135 psi |
| 1-Octene | 100 μL |
| Total Volume | 5 mL |
| Solvent | Isohexane |
| Quench Value | 20 psi |
| Maximum Reaction Time | 30 min |

TABLE 2

Catalyst activity and polymer properties for EO copolymerization with Activator-1.

| Entry | Run | Catalyst | Reaction Time (s) | yield (g) | activity (g/mmol/hr) | Mw (kg/mol) | Mn (kg/mol) | Mw/Mn | wt % octene | Tm (° C.) |
|---|---|---|---|---|---|---|---|---|---|---|
| 1 | 1 | 1-Zr | 20.7 | 0.091 | 791304 | 199 | 108 | 1.85 | 14.7 | 105.4 |
| 2 | 2 | 1-Zr | 22.9 | 0.088 | 691703 | 181 | 108 | 1.68 | 15.5 | 103.1 |
| 3 | 1 | 1-Hf | 39.3 | 0.077 | 352672 | 179 | 108 | 1.65 | 14.3 | 101.4 |
| 4 | 2 | 1-Hf | 27.0 | 0.085 | 566667 | 156 | 97 | 1.61 | 13.3 | 102.9 |
| 5 | 1 | 2-Zr | 1200.6 | 0.000 | 0 | — | — | — | — | — |
| 6 | 2 | 2-Zr | 1200.4 | 0.001 | 150 | — | — | — | — | — |
| 7 | 1 | 2-Hf | 1201.2 | 0.001 | 150 | — | — | — | — | — |
| 8 | 2 | 2-Hf | 1200.4 | 0.000 | 0 | — | — | — | — | — |
| 9 | 1 | 3-Zr | 1200.1 | 0.000 | 0 | — | — | — | — | — |
| 10 | 2 | 3-Zr | 1201.0 | 0.000 | 0 | — | — | — | — | — |
| 11 | 1 | 3-Hf | 1200.8 | 0.001 | 150 | — | — | — | — | — |
| 12 | 2 | 3-Hf | 1201.7 | 0.000 | 0 | — | — | — | — | — |
| 13 | 1 | 4-Zr | 1801.0 | 0.000 | 0 | — | — | — | — | — |
| 14 | 2 | 4-Zr | 1800.4 | 0.000 | 0 | — | — | — | — | — |
| 15 | 1 | 4-Hf | 1800.0 | 0.000 | 0 | — | — | — | — | — |
| 16 | 2 | 4-Hf | 1800.5 | 0.000 | 0 | — | — | — | — | — |
| 17 | 1 | 5-Zr | 25.8 | 0.120 | 837209 | 2936 | 1586 | 1.85 | 0.0 | 128.9 |
| 18 | 2 | 5-Zr | 28.8 | 0.115 | 718750 | 2931 | 1323 | 2.22 | 0.9 | 128.5 |
| 19 | 1 | 5-Hf | 44.1 | 0.106 | 432653 | 4207 | 2855 | 1.47 | 0.0 | 126.4 |
| 20 | 1 | 6-Zr | 41.6 | 0.091 | 393750 | 739 | 387 | 1.91 | 6.3 | 117.5 |
| 21 | 2 | 6-Zr | 44.5 | 0.094 | 380225 | 754 | 409 | 1.84 | 7.1 | 116.8 |
| 22 | 1 | 6-Hf | 263.5 | 0.053 | 36205 | 1751 | 912 | 1.92 | 4.5 | 117.1 |
| 23 | 1 | 7-Zr | 835.2 | 0.059 | 12716 | 1386 | 815 | 1.70 | 3.0 | 121.0 |
| 24 | 2 | 7-Zr | 219.5 | 0.044 | 36082 | 1121 | 655 | 1.71 | 2.7 | 121.8 |
| 25 | 1 | 7-Hf | 1800.1 | 0.013 | 1300 | 72 | 44 | 1.63 | 2.6 | 124.5 |
| 26 | 2 | 7-Hf | 1800.7 | 0.012 | 1200 | 62 | 37 | 1.66 | 3.4 | 125.5 |
| 27 | 1 | 8-Zr | 304.8 | 0.046 | 27165 | 109 | 64 | 1.70 | 6.9 | 115.0 |
| 28 | 2 | 8-Zr | 288.9 | 0.046 | 28660 | 113 | 58 | 1.97 | 6.5 | 115.3 |
| 29 | 1 | 8-Hf | 1800.3 | 0.029 | 2900 | 40 | 22 | 1.80 | 10.4 | 112.5 |
| 30 | 1 | 9-Zr | 1800.4 | 0.015 | 1500 | 22 | 18 | 1.21 | 8.3 | 115.1 |
| 31 | 2 | 9-Zr | 1800.1 | 0.015 | 1500 | 22 | 18 | 1.23 | 11.0 | 115.8 |
| 32 | 1 | 9-Hf | 1800.3 | 0.007 | 700 | — | — | — | — | — |
| 33 | 2 | 9-Hf | 1800.3 | 0.008 | 800 | — | — | — | — | — |

TABLE 4

Catalyst activity and polymer properties for EO copolymerization with MAO.

| Entry | Run | Catalyst | Ethylene Pressure | Reaction time | Yield (g) | activity (g/mmol/hr) | Mw (kg/mol) | Mn (kg/mol) | Mw/Mn | wt % octene | Tm (° C.) |
|---|---|---|---|---|---|---|---|---|---|---|---|
| 1 | 1 | 1-Zr | 120 | 26.1 | 0.091 | 627586 | 275 | 145 | 1.89 | 13.6 | 106.9 |
| 2 | 2 | 1-Zr | 120 | 25.7 | 0.086 | 602335 | 326 | 180 | 1.81 | 14.1 | 105.2 |
| 3 | 1 | 1-Hf | 120 | 48.0 | 0.099 | 371250 | 339 | 201 | 1.69 | 14.9 | 99.3 |
| 4 | 2 | 1-Hf | 120 | 44.7 | 0.091 | 366443 | 485 | 251 | 1.93 | 17.1 | 99.4 |
| 5 | 1 | 2-Zr | 120 | 1800.2 | 0.022 | 2200 | 23 | 13 | 1.72 | 18.7 | 105.5 |
| 6 | 1 | 2-Hf | 120 | 260.2 | 0.043 | 29746 | 61 | 38 | 1.59 | 12.4 | 111.5 |
| 7 | 1 | 3-Zr | 120 | 1801.9 | 0.012 | 1199 | 5 | 3 | 1.57 | 38.4 | 117.9 |
| 8 | 1 | 3-Hf | 120 | 1800.5 | 0.036 | 3599 | 29 | 15 | 1.91 | 20.0 | 96.8 |
| 9 | 1 | 4-Zr | 135 | 1801.2 | 0.004 | 400 | 0 | 0 | — | — | — |
| 10 | 2 | 4-Zr | 135 | 1800.6 | 0.009 | 900 | 0 | 0 | — | — | — |
| 11 | 1 | 4-Hf | 135 | 1800.9 | 0.035 | 3498 | 28 | 18 | 1.54 | 7.2 | 115.5 |
| 12 | 1 | 5-Zr | 120 | 23.7 | 0.098 | 745562 | 2208 | 978 | 2.26 | 2.4 | 126.9 |
| 13 | 1 | 5-Zr | 135 | 26.9 | 0.110 | 735786 | 2084 | 825 | 2.53 | 1.8 | 128.3 |
| 14 | 2 | 5-Zr | 135 | 22.1 | 0.108 | 881633 | 2431 | 889 | 2.74 | 2.2 | 127.8 |
| 15 | 1 | 5-Hf | 120 | 35.4 | 0.099 | 503674 | 1860 | 521 | 3.57 | 4.6 | 123.5 |
| 16 | 2 | 5-Hf | 120 | 32.5 | 0.093 | 515712 | 2319 | 465 | 4.99 | 5.0 | 123.8 |
| 17 | 1 | 5-Hf | 135 | 27.4 | 0.107 | 701384 | 2398 | 600 | 3.99 | 3.5 | 124.2 |
| 18 | 2 | 5-Hf | 135 | 30.8 | 0.101 | 588921 | 2352 | 532 | 4.42 | 4.4 | 124.1 |
| 19 | 1 | 6-Zr | 120 | 53.6 | 0.105 | 352415 | 465 | 223 | 2.08 | 12.4 | 116.1 |
| 20 | 2 | 6-Zr | 120 | 47.9 | 0.098 | 368267 | 606 | 305 | 1.99 | 12.0 | 115.1 |
| 21 | 1 | 6-Zr | 135 | 50.0 | 0.094 | 338265 | 520 | 265 | 1.96 | 10.6 | 117.4 |
| 22 | 2 | 6-Zr | 135 | 45.0 | 0.110 | 440489 | 566 | 287 | 1.97 | 10.6 | 117.0 |
| 23 | 1 | 6-Hf | 120 | 157.3 | 0.059 | 67501 | 499 | 274 | 1.82 | 6.2 | 116.9 |
| 24 | 2 | 6-Hf | 120 | 164.4 | 0.061 | 66784 | 764 | 424 | 1.80 | 5.9 | 116.3 |
| 25 | 1 | 6-Hf | 135 | 147.6 | 0.058 | 70736 | 583 | 310 | 1.88 | 5.3 | 118.1 |
| 26 | 2 | 6-Hf | 135 | 155.1 | 0.064 | 74294 | 789 | 431 | 1.83 | 5.6 | 117.3 |
| 27 | 1 | 7-Zr | 135 | 109.2 | 0.063 | 103846 | 516 | 289 | 1.79 | 2.7 | 121.5 |
| 28 | 2 | 7-Zr | 135 | 133.9 | 0.065 | 87372 | 482 | 275 | 1.75 | 2.8 | 121.0 |
| 29 | 1 | 7-Hf | 135 | 1005.1 | 0.039 | 6984 | 252 | 111 | 2.27 | 0.8 | 125.8 |
| 30 | 2 | 7-Hf | 135 | 1133.3 | 0.038 | 6035 | 249 | 119 | 2.10 | 2.2 | 125.3 |
| 31 | 1 | 8-Zr | 120 | 301.7 | 0.047 | 28041 | 150 | 77 | 1.94 | 12.0 | 103.4 |
| 32 | 2 | 8-Zr | 120 | 306.6 | 0.049 | 28766 | 236 | 118 | 2.00 | 14.7 | 102.9 |
| 33 | 1 | 8-Zr | 135 | 286.0 | 0.049 | 30843 | 154 | 85 | 1.81 | 10.3 | 106.6 |
| 34 | 2 | 8-Zr | 135 | 265.6 | 0.048 | 32529 | 253 | 123 | 2.05 | 11.8 | 105.7 |
| 35 | 1 | 8-Hf | 120 | 1460.9 | 0.048 | 5914 | 47 | 28 | 1.68 | 18.8 | 97.8 |
| 36 | 2 | 8-Hf | 120 | 1222.7 | 0.044 | 6478 | 57 | 30 | 1.91 | 20.8 | 98.8 |
| 37 | 1 | 8-Hf | 135 | 1800.7 | 0.059 | 5898 | 60 | 33 | 1.83 | 14.7 | 103.8 |
| 38 | 2 | 8-Hf | 135 | 1083.5 | 0.045 | 7476 | 65 | 38 | 1.71 | 17.6 | 101.9 |
| 39 | 1 | 9-Zr | 120 | 735.7 | 0.050 | 12234 | 70 | 45 | 1.55 | 19.1 | 95.2 |
| 40 | 2 | 9-Zr | 120 | 602.5 | 0.047 | 14041 | 90 | 54 | 1.68 | 19.7 | 93.8 |
| 41 | 1 | 9-Zr | 135 | 523.1 | 0.047 | 16172 | 68 | 41 | 1.67 | 17.4 | 98.3 |
| 42 | 2 | 9-Zr | 135 | 540.7 | 0.047 | 15646 | 95 | 55 | 1.73 | 17.5 | 97.5 |
| 43 | 1 | 9-Hf | 120 | 1800.3 | 0.014 | 1400 | 10 | 6 | 1.57 | 25.6 | 84.6 |
| 44 | 2 | 9-Hf | 120 | 1800.4 | 0.015 | 1500 | 14 | 8 | 1.63 | 23.1 | 89.3 |
| 45 | 1 | 9-Hf | 135 | 1800.5 | 0.018 | 1799 | 16 | 9 | 1.73 | 26.0 | 93.1 |

Entries 1 to 4 and 12 to 28 show that the inventive catalysts exhibited higher activities compared with the reference catalysts (entries 31 to 45). Entries 1 to 4 and 12 to 30 show that, on the average, the inventive catalysts had higher polymer molecular weight capability compared with the reference catalysts of the same metal (entries 31 to 45).

TABLE 5

Reaction conditions for ethylene-ENB copolymerization with Activator-1.

| | |
|---|---|
| Catalyst loading | 0.080 μmol |
| Activator-1 | 0.088 μmol (1.1 eq) |
| Temperature | 80 or 100° C. |
| Ethylene Pressure | 135 psi |
| 5-ethylidene-2-norbornene (ENB) | 85 μL |
| Total Volume | 5 mL |
| Solvent | Isohexane |
| Aluminum compound | 0.25 μmol TNOAL |
| Quench Value | 20 psi |
| Maximum Reaction Time | 30 min |

TABLE 6

Catalyst activity and polymer properties for E-ENB copolymerization with Activator-1.

| Entry | Run | Catalyst | Reaction Temp (° C.) | Reaction Time (s) | Yield (g) | Activity (g/mmol/hr) | Mw (kg/mol) | Mn (kg/mol) | Mw/Mn | wt % ENB | Tm (° C.) |
|---|---|---|---|---|---|---|---|---|---|---|---|
| 1 | 1 | 1-Zr | 80 | 358.9 | 0.069 | 8651 | 118 | 73 | 1.63 | 22.3 | 53.3 |
| 2 | 2 | 1-Zr | 80 | 364.5 | 0.069 | 8519 | 115 | 71 | 1.63 | 21.1 | 53.3 |

TABLE 6-continued

Catalyst activity and polymer properties for E-ENB copolymerization with Activator-1.

| Entry | Run | Catalyst | Reaction Temp (° C.) | Reaction Time (s) | Yield (g) | Activity (g/mmol/hr) | Mw (kg/mol) | Mn (kg/mol) | Mw/Mn | wt % ENB | Tm (° C.) |
|---|---|---|---|---|---|---|---|---|---|---|---|
| 3 | 1 | 1-Zr | 100 | 453.6 | 0.070 | 6944 | 69 | 40 | 1.74 | 22.3 | — |
| 4 | 2 | 1-Zr | 100 | 265.8 | 0.070 | 11851 | 66 | 41 | 1.63 | 21.3 | 57.1 |
| 5 | 1 | 1-Hf | 80 | 899.7 | 0.059 | 2951 | 213 | 123 | 1.73 | 21.7 | 56.1 |
| 6 | 2 | 1-Hf | 80 | 714.7 | 0.057 | 3589 | 206 | 118 | 1.74 | 20.1 | 61.9 |
| 7 | 1 | 1-Hf | 100 | 801.0 | 0.070 | 3933 | 114 | 72 | 1.59 | 20.5 | 56.4 |
| 8 | 2 | 1-Hf | 100 | 327.4 | 0.055 | 7560 | 119 | 73 | 1.63 | 21.0 | 67.6 |
| 9 | 1 | 5-Zr | 80 | 43.0 | 0.141 | 147558 | 3239 | 1932 | 1.68 | 8.1 | 114.8 |
| 10 | 2 | 5-Zr | 80 | 39.2 | 0.128 | 146939 | 3215 | 2114 | 1.52 | 8.1 | 114.4 |
| 11 | 1 | 5-Zr | 100 | 15.3 | 0.104 | 305882 | 2380 | 1423 | 1.67 | 8.5 | 112.9 |
| 12 | 2 | 5-Zr | 100 | 30.5 | 0.104 | 153443 | 2474 | 1563 | 1.58 | 7.8 | 113.6 |
| 13 | 1 | 5-Hf | 80 | 127.7 | 0.121 | 42639 | 3607 | 2739 | 1.32 | 7.9 | 113.5 |
| 14 | 2 | 5-Hf | 80 | 97.0 | 0.104 | 48247 | 3371 | 2288 | 1.47 | 7.8 | 113.4 |
| 15 | 1 | 5-Hf | 100 | 53.3 | 0.087 | 73452 | 2474 | 1700 | 1.46 | 7.9 | 113.6 |
| 16 | 2 | 5-Hf | 100 | 38.6 | 0.087 | 101425 | 2458 | 1554 | 1.58 | 7.9 | 114.7 |
| 17 | 1 | 6-Zr | 80 | 126.5 | 0.127 | 45178 | 638 | 354 | 1.80 | 19.0 | 60.0 |
| 18 | 2 | 6-Zr | 80 | 89.4 | 0.118 | 59396 | 679 | 385 | 1.76 | 19.4 | 69.7 |
| 19 | 1 | 6-Zr | 100 | 72.0 | 0.102 | 63750 | 443 | 220 | 2.02 | 21.2 | 60.8 |
| 20 | 2 | 6-Zr | 100 | 61.9 | 0.100 | 72698 | 495 | 261 | 1.90 | 19.1 | 70.5 |
| 21 | 1 | 6-Hf | 80 | 322.2 | 0.069 | 9637 | 1859 | 1112 | 1.67 | 19.7 | — |
| 22 | 2 | 6-Hf | 80 | 500.4 | 0.085 | 7644 | 1816 | 1063 | 1.71 | 21.5 | — |
| 23 | 1 | 6-Hf | 100 | 316.3 | 0.086 | 12235 | 1324 | 670 | 1.98 | 19.8 | — |
| 24 | 2 | 6-Hf | 100 | 218.0 | 0.072 | 14862 | 1266 | 642 | 1.97 | 20.3 | — |
| 25 | 1 | 7-Zr | 80 | 1005.3 | 0.061 | 2730 | 1041 | 546 | 1.91 | 21.8 | — |
| 26 | 2 | 7-Zr | 80 | 1074.1 | 0.053 | 2220 | 850 | 456 | 1.86 | 21.0 | — |
| 27 | 1 | 7-Hf | 80 | 1801.2 | 0.015 | 375 | 321 | 206 | 1.56 | 21.6 | 116.7 |
| 28 | 2 | 7-Hf | 80 | 1800.8 | 0.014 | 350 | 267 | 182 | 1.46 | 21.6 | — |
| 29 | 1 | 8-Zr | 80 | 1800.7 | 0.042 | 1050 | 619 | 310 | 2.00 | 20.3 | — |
| 30 | 1 | 8-Zr | 100 | 1800.6 | 0.024 | 600 | 298 | 169 | 1.76 | 19.6 | — |
| 31 | 1 | 8-Hf | 80 | 1800.4 | 0.009 | 225 | — | — | — | — | — |
| 32 | 1 | 9-Zr | 80 | 1800.3 | 0.041 | 1025 | 102 | 67 | 1.52 | 21.9 | — |
| 33 | 2 | 9-Zr | 80 | 1800.5 | 0.047 | 1175 | 112 | 72 | 1.55 | 21.1 | — |
| 34 | 1 | 9-Zr | 100 | 1800.1 | 0.063 | 1575 | 128 | 75 | 1.70 | 22.6 | — |
| 35 | 2 | 9-Zr | 100 | 1710.0 | 0.061 | 1605 | 136 | 90 | 1.52 | 21.9 | — |
| 36 | 1 | 9-Hf | 80 | 1801.4 | 0.010 | 250 | — | — | — | — | — |
| 37 | 2 | 9-Hf | 80 | 1800.1 | 0.011 | 275 | 30 | 22 | 1.33 | 20.3 | — |
| 38 | 1 | 9-Hf | 100 | 1800.4 | 0.013 | 325 | 43 | 28 | 1.50 | 20.5 | — |
| 39 | 2 | 9-Hf | 100 | 1800.5 | 0.016 | 400 | 52 | 37 | 1.41 | 20.8 | — |

Entries 1 to 26 show that the inventive catalysts exhibited higher activities compared with the reference catalysts (entries 29 to 39). Entries 9 to 28 show that the inventive catalysts had higher polymer molecular weight capability compared with the reference catalysts at the same temperature (entries 29 to 39).

TABLE 7

Reaction conditions for ethylene-propylene (EP) copolymerization with Activator-1.

| | |
|---|---|
| Catalyst loading | 0.010-0.020 μmol |
| Activator-1 | 1.1 eq |
| Temperature | 80-110° C. |
| Ethylene Pressure | 25-160 psi |
| Propylene | 500 or 1000 μL |
| Total Volume | 5.1 mL |
| Solvent | Isohexane |
| Aluminum compound | 0.50 μmol TNOAL |
| Quench Value | 4-10 psi |
| Maximum Reaction Time | 30 min |

TABLE 8

Catalyst activity and polymer properties for EP copolymerization with Activator-1.

| Entry | Run | Catalyst Name | Catalyst umol | Reaction Temp (° C.) | Ethylene Pressure (psi) | Propylene (μL) | Quench Value (psi) | Reaction Time (s) | Yield (g) | Activity (g/mmol/hr) | Mw (kg/mol) | Mn (kg/mol) | Mw/Mn | Wt % Propylene | Tm (° C.) |
|---|---|---|---|---|---|---|---|---|---|---|---|---|---|---|---|
| 1 | 1 | 1-Zr | 0.015 | 80 | 125 | 500 | 4 | 6.8 | 0.132 | 4658824 | 191 | 99 | 1.94 | 29.2 | 46.5 |
| 2 | 2 | 1-Zr | 0.015 | 80 | 125 | 500 | 4 | 5.9 | 0.133 | 5410169 | 199 | 117 | 1.71 | — | 45.3 |
| 3 | 1 | 1-Hf | 0.015 | 80 | 125 | 500 | 4 | 20.8 | 0.112 | 1292308 | 417 | 247 | 1.69 | 29.1 | 46.1 |
| 4 | 2 | 1-Hf | 0.015 | 80 | 125 | 500 | 4 | 16.2 | 0.101 | 1496296 | 413 | 235 | 1.75 | — | 47.0 |
| 5 | 1 | 1-Hf | 0.015 | 80 | 85 | 500 | 4 | 15.8 | 0.058 | 881013 | 378 | 211 | 1.79 | — | 47.0 |
| 6 | 2 | 1-Hf | 0.015 | 80 | 85 | 500 | 4 | 18.2 | 0.079 | 1041758 | 397 | 243 | 1.63 | 30.0 | 38.4 |

TABLE 8-continued

Catalyst activity and polymer properties for EP copolymerization with Activator-1.

| Entry | Run | Catalyst Name | umol | Reaction Temp (° C.) | Ethylene Pressure (psi) | Propylene (μL) | Quench Value (psi) | Reaction Time (s) | Yield (g) | Activity (g/mmol/hr) | Mw (kg/mol) | Mn (kg/mol) | Mw/Mn | Wt % Propylene | Tm (° C.) |
|---|---|---|---|---|---|---|---|---|---|---|---|---|---|---|---|
| 7 | 1 | 1-Hf | 0.015 | 80 | 125 | 500 | 4 | 18.5 | 0.106 | 1375135 | 475 | 278 | 1.71 | 23.7 | 52.8 |
| 8 | 2 | 1-Hf | 0.015 | 80 | 125 | 500 | 4 | 28.1 | 0.119 | 1016370 | 480 | 283 | 1.69 | — | 50.4 |
| 9 | 1 | 1-Hf | 0.015 | 80 | 135 | 1000 | 4 | 20.7 | 0.108 | 1252174 | 504 | 304 | 1.66 | 27.9 | 41.1 |
| 10 | 2 | 1-Hf | 0.015 | 80 | 135 | 1000 | 4 | 22.3 | 0.122 | 1313004 | 544 | 334 | 1.63 | — | 38.4 |
| 11 | 1 | 1-Hf | 0.015 | 100 | 105 | 500 | 5 | 19.1 | 0.090 | 1130890 | 324 | 179 | 1.81 | 31.5 | 55.9 |
| 12 | 2 | 1-Hf | 0.015 | 100 | 105 | 500 | 5 | 25.2 | 0.060 | 571429 | 437 | 290 | 1.50 | — | 54.9 |
| 13 | 1 | 1-Hf | 0.015 | 100 | 155 | 500 | 5 | 15.7 | 0.075 | 1146497 | 465 | 276 | 1.68 | 17.3 | 80.0 |
| 14 | 2 | 1-Hf | 0.015 | 100 | 155 | 500 | 5 | 17.7 | 0.059 | 800000 | 461 | 280 | 1.65 | — | 79.7 |
| 15 | 1 | 1-Hf | 0.015 | 100 | 160 | 1000 | 5 | 17.7 | 0.088 | 1193220 | 398 | 259 | 1.54 | 23.1 | 54.6 |
| 16 | 2 | 1-Hf | 0.015 | 100 | 160 | 1000 | 5 | 38.3 | 0.057 | 357180 | 377 | 229 | 1.64 | — | 58.9 |
| 17 | 1 | 5-Zr | 0.01 | 80 | 125 | 500 | 4 | 13.3 | 0.124 | 3356391 | 3374 | 2175 | 1.55 | — | 125.9 |
| 18 | 2 | 5-Zr | 0.01 | 80 | 125 | 500 | 4 | 13.7 | 0.118 | 3100730 | 3424 | 1662 | 2.06 | — | 124.8 |
| 19 | 3 | 5-Zr | 0.01 | 80 | 125 | 500 | 4 | 9.7 | 0.124 | 4602062 | 3066 | 1180 | 2.60 | — | 125.0 |
| 20 | 1 | 5-Zr | 0.01 | 110 | 125 | 500 | 4 | 10.1 | 0.091 | 3243564 | 635 | 325 | 1.95 | 23.7 | 129.8 |
| 21 | 2 | 5-Zr | 0.01 | 110 | 125 | 500 | 4 | 10.2 | 0.082 | 2894118 | 1876 | 1015 | 1.85 | — | 127.7 |
| 22 | 1 | 5-Zr | 0.01 | 110 | 50 | 1000 | 4 | 12.7 | 0.041 | 1162205 | 584 | 304 | 1.92 | — | 119.8 |
| 23 | 2 | 5-Zr | 0.01 | 110 | 50 | 1000 | 4 | 12.5 | 0.004 | 115200 | — | — | — | — | — |
| 24 | 1 | 5-Zr | 0.01 | 110 | 25 | 1000 | 4 | 91.5 | 0.023 | 90492 | 765 | 410 | 1.87 | — | 107.0 |
| 25 | 2 | 5-Zr | 0.01 | 110 | 25 | 1000 | 4 | 100.4 | 0.028 | 100398 | 631 | 281 | 2.24 | — | 102.2 |
| 26 | 1 | 5-Hf | 0.02 | 80 | 125 | 500 | 4 | 22.8 | 0.102 | 805263 | 3737 | 1980 | 1.89 | — | 120.5 |
| 27 | 2 | 5-Hf | 0.02 | 80 | 125 | 500 | 4 | 17.1 | 0.109 | 1147368 | 3773 | 1989 | 1.90 | — | 119.9 |
| 28 | 3 | 5-Hf | 0.02 | 80 | 125 | 500 | 4 | 21.1 | 0.110 | 938389 | 3071 | 913 | 3.36 | — | 120.0 |
| 29 | 1 | 5-Hf | 0.02 | 110 | 125 | 500 | 4 | 18.06 | 0.079 | 787375 | 1172 | 672 | 1.74 | — | 124.1 |
| 30 | 2 | 5-Hf | 0.02 | 110 | 125 | 500 | 4 | 17.4 | 0.085 | 879310 | 2132 | 1183 | 1.80 | — | 121.9 |
| 31 | 1 | 5-Hf | 0.02 | 110 | 50 | 1000 | 4 | 15.88 | 0.043 | 487406 | 624 | 287 | 2.17 | 26.5 | 107.7 |
| 32 | 2 | 5-Hf | 0.02 | 110 | 50 | 1000 | 4 | 18.34 | 0.043 | 422028 | 1096 | 541 | 2.02 | — | 106.1 |
| 33 | 1 | 5-Hf | 0.02 | 110 | 25 | 1000 | 4 | 68.46 | 0.039 | 102542 | 178 | 97 | 1.83 | 34.9 | — |
| 34 | 2 | 5-Hf | 0.02 | 110 | 25 | 1000 | 4 | 66.59 | 0.038 | 102718 | 314 | 105 | 2.99 | — | 125.6 |
| 35 | 1 | 6-Zr | 0.01 | 80 | 125 | 500 | 4 | 14 | 0.052 | 1337143 | 994 | 603 | 1.65 | — | 103.2 |
| 36 | 2 | 6-Zr | 0.01 | 80 | 125 | 500 | 4 | 20.8 | 0.049 | 848077 | 964 | 544 | 1.77 | — | 102.6 |
| 37 | 3 | 6-Zr | 0.01 | 80 | 125 | 500 | 4 | 17 | 0.050 | 1058824 | 976 | 523 | 1.87 | — | 101.9 |
| 38 | 1 | 6-Zr | 0.01 | 110 | 125 | 500 | 6 | 66.6 | 0.037 | 200000 | 396 | 223 | 1.78 | 21.1 | 107.7 |
| 39 | 2 | 6-Zr | 0.01 | 110 | 125 | 500 | 6 | 34 | 0.043 | 455294 | 617 | 302 | 2.05 | — | 104.3 |
| 40 | 1 | 6-Zr | 0.01 | 110 | 50 | 1000 | 6 | 93.6 | 0.031 | 119231 | 230 | 123 | 1.88 | — | 48.7 |
| 41 | 2 | 6-Zr | 0.01 | 110 | 50 | 1000 | 6 | 84.5 | 0.034 | 144852 | 319 | 172 | 1.86 | — | — |
| 42 | 1 | 6-Zr | 0.01 | 110 | 25 | 1000 | 6 | 734 | 0.024 | 11771 | 114 | 63 | 1.80 | — | — |
| 43 | 2 | 6-Zr | 0.01 | 110 | 25 | 1000 | 6 | 311 | 0.028 | 32412 | 212 | 110 | 1.93 | — | — |
| 44 | 1 | 6-Hf | 0.02 | 80 | 125 | 500 | 4 | 91.7 | 0.029 | 56925 | 1625 | 926 | 1.75 | — | 81.0 |
| 45 | 2 | 6-Hf | 0.02 | 80 | 125 | 500 | 4 | 133 | 0.022 | 29774 | 1616 | 1014 | 1.60 | — | 81.7 |
| 46 | 3 | 6-Hf | 0.02 | 80 | 125 | 500 | 4 | 143.8 | 0.027 | 33797 | 1705 | 1076 | 1.58 | — | 79.5 |
| 47 | 1 | 6-Hf | 0.02 | 110 | 125 | 500 | 6 | 106.2 | 0.034 | 57627 | 706 | 448 | 1.58 | — | 80.2 |
| 48 | 2 | 6-Hf | 0.02 | 110 | 125 | 500 | 6 | 113.64 | 0.031 | 49102 | 810 | 482 | 1.68 | — | 79.5 |
| 49 | 1 | 6-Hf | 0.02 | 110 | 50 | 1000 | 6 | 240.16 | 0.028 | 20986 | 313 | 192 | 1.63 | 41.8 | — |
| 50 | 2 | 6-Hf | 0.02 | 110 | 50 | 1000 | 6 | 192.79 | 0.026 | 24275 | 365 | 225 | 1.62 | — | — |
| 51 | 1 | 6-Hf | 0.02 | 110 | 25 | 1000 | 6 | 793.73 | 0.027 | 6123 | 132 | 79 | 1.67 | 60.5 | — |
| 52 | 2 | 6-Hf | 0.02 | 110 | 25 | 1000 | 6 | 719.2 | 0.026 | 6507 | 199 | 128 | 1.56 | — | — |
| 53 | 1 | 7-Zr | 0.02 | 110 | 125 | 500 | 6 | 78.7 | 0.022 | 50318 | 493 | 249 | 1.98 | 15.0 | 98.3 |
| 54 | 1 | 7-Hf | 0.02 | 110 | 125 | 500 | 10 | 1800.6 | 0.009 | 900 | — | — | — | — | — |
| 55 | 2 | 7-Hf | 0.02 | 110 | 125 | 500 | 10 | 1800.9 | 0.004 | 400 | — | — | — | — | — |
| 56 | 1 | 8-Zr | 0.01 | 80 | 125 | 500 | 4 | 237.1 | 0.019 | 28849 | 151 | 95 | 1.60 | — | 50.2 |
| 57 | 2 | 8-Zr | 0.01 | 80 | 125 | 500 | 4 | 291.5 | 0.014 | 17290 | 142 | 87 | 1.62 | — | 48.5 |
| 58 | 3 | 8-Zr | 0.01 | 80 | 125 | 500 | 4 | 553.9 | 0.014 | 9099 | 145 | 83 | 1.75 | — | 52.9 |
| 59 | 1 | 8-Hf | 0.02 | 80 | 125 | 500 | 4 | 443.9 | 0.015 | 6082 | 54 | 33 | 1.64 | — | 41.2 |
| 60 | 2 | 8-Hf | 0.02 | 80 | 125 | 500 | 4 | 842 | 0.012 | 2565 | 52 | 30 | 1.75 | — | 42.8 |
| 61 | 3 | 8-Hf | 0.02 | 80 | 125 | 500 | 4 | 778.9 | 0.013 | 3004 | — | — | — | — | — |
| 62 | 1 | 9-Zr | 0.01 | 80 | 125 | 500 | 4 | 1800.5 | 0.010 | 1999 | 18 | 13 | 1.46 | — | 41.2 |
| 63 | 2 | 9-Zr | 0.01 | 80 | 125 | 500 | 4 | 1800.8 | 0.008 | 1599 | — | — | — | — | — |
| 64 | 3 | 9-Zr | 0.01 | 80 | 125 | 500 | 4 | 1800.8 | 0.008 | 1599 | — | — | — | — | — |
| 65 | 1 | 9-Hf | 0.02 | 80 | 125 | 500 | 4 | 1800.31 | 0.002 | 200 | — | — | — | — | — |
| 66 | 2 | 9-Hf | 0.02 | 80 | 125 | 500 | 4 | 1801 | 0.008 | 800 | — | — | — | — | — |
| 67 | 3 | 9-Hf | 0.02 | 80 | 125 | 500 | 4 | 1800.2 | 0.007 | 700 | — | — | — | — | — |

Entries 1 to 4, 7 to 10, 17 to 19, 26 to 28, 35 to 37 and 44 to 46 show that the inventive catalysts exhibited higher activities and higher polymer molecular weight capability compared with the reference catalysts (entries 56 to 67) under similar conditions.

TABLE 9

Reaction conditions for EO copolymerization using various chain transfer agents.

| Catalyst loading | 0.020 µmol |
|---|---|
| Activator-1 | 1.1 eq |

TABLE 9-continued

Reaction conditions for EO copolymerization using various chain transfer agents.

| Temperature | 100° C. |
|---|---|
| Ethylene Pressure | 135 psi |
| 1-Octene | 100 µL |
| Total Volume | 5 mL |
| Solvent | Isohexane |
| Chain Transfer Agent | variable |
| Quench Value | 20 psi |
| Maximum Reaction Time | 30 min |

TABLE 10

Catalyst activity and polymer properties for EO copolymerization using various CTAs.

| Entry | Run | Catalyst | CTA | nmol Al or | Reaction Time | Yield (g) | Activity (g/mmol/hr) | Mw (kg/mol) | Mn (kg/mol) | Mw/Mn | wt % octene | Tm (° C.) |
|---|---|---|---|---|---|---|---|---|---|---|---|---|
| 1 | 1 | 1-Zr | DIBALO | 400 | 67.3 | 0.110 | 294205 | 606 | 318 | 1.91 | 14.8 | 98.9 |
| 2 | 2 | 1-Zr | DIBALO | 400 | 36.8 | 0.100 | 489130 | 635 | 371 | 1.71 | 14.8 | 98.9 |
| 3 | 1 | 1-Zr | DIBALO | 1600 | 33.1 | 0.100 | 543807 | 566 | 308 | 1.84 | 14.1 | 102.2 |
| 4 | 2 | 1-Zr | DIBALO | 1600 | 30.4 | 0.099 | 586184 | 548 | 273 | 2.01 | 12.5 | 102.1 |
| 5 | 1 | 1-Zr | DIBALO | 2800 | 32.9 | 0.104 | 568997 | 497 | 258 | 1.93 | 12.5 | 103.7 |
| 6 | 2 | 1-Zr | DIBALO | 2800 | 27.4 | 0.096 | 630657 | 492 | 259 | 1.90 | 12.2 | 106.3 |
| 7 | 1 | 1-Zr | DIBALO | 4000 | 26.5 | 0.095 | 645283 | 450 | 212 | 2.12 | 9.0 | 109.7 |
| 8 | 2 | 1-Zr | DIBALO | 4000 | 24.1 | 0.095 | 709544 | 452 | 231 | 1.96 | 7.6 | 112.8 |
| 9 | 1 | 1-Hf | DIBALO | 400 | 155.1 | 0.119 | 138104 | 2097 | 775 | 2.70 | 19.1 | 94.2 |
| 10 | 2 | 1-Hf | DIBALO | 400 | 124.8 | 0.113 | 162981 | 2092 | 933 | 2.24 | 20.3 | 92.8 |
| 11 | 1 | 1-Hf | DIBALO | 1600 | 110.7 | 0.108 | 175610 | 1411 | 477 | 2.96 | 18.9 | 95.6 |
| 12 | 2 | 1-Hf | DIBALO | 1600 | 223.5 | 0.121 | 97450 | 1608 | 569 | 2.83 | 20.1 | 97.3 |
| 13 | 1 | 1-Hf | DIBALO | 2800 | 40.2 | 0.095 | 425373 | 1229 | 549 | 2.24 | 13.2 | 99.5 |
| 14 | 2 | 1-Hf | DIBALO | 2800 | 41.1 | 0.094 | 411679 | 1180 | 487 | 2.42 | 13.2 | 99.9 |
| 15 | 1 | 1-Hf | DIBALO | 4000 | 33.7 | 0.095 | 507418 | 1171 | 529 | 2.21 | 9.6 | 106.3 |
| 16 | 2 | 1-Hf | DIBALO | 4000 | 51.4 | 0.094 | 329183 | 1158 | 585 | 1.98 | 10.6 | 104.4 |
| 17 | 1 | 1-Zr | diethylzinc | 400 | 30.4 | 0.086 | 509211 | 309 | 169 | 1.83 | 13.0 | 105.1 |
| 18 | 2 | 1-Zr | diethylzinc | 400 | 28.8 | 0.092 | 575000 | 289 | 158 | 1.83 | 12.2 | 105.5 |
| 19 | 1 | 1-Zr | diethylzinc | 1600 | 21.8 | 0.086 | 710092 | 149 | 93 | 1.59 | 11.0 | 111.8 |
| 20 | 2 | 1-Zr | diethylzinc | 1600 | 20.7 | 0.085 | 739130 | 143 | 79 | 1.82 | 8.0 | 112.7 |
| 21 | 1 | 1-Zr | diethylzinc | 2800 | 17.9 | 0.087 | 874860 | 104 | 63 | 1.65 | 6.9 | 118.5 |
| 22 | 2 | 1-Zr | diethylzinc | 2800 | 17.9 | 0.084 | 844693 | 96 | 54 | 1.78 | 6.9 | 118.2 |
| 23 | 1 | 1-Zr | diethylzinc | 4000 | 14.3 | 0.086 | 1082517 | 75 | 48 | 1.58 | 3.1 | 125.7 |
| 24 | 2 | 1-Zr | diethylzinc | 4000 | 22.6 | 0.101 | 804425 | 81 | 50 | 1.62 | 6.1 | 120.5 |
| 25 | 1 | 1-Hf | diethylzinc | 400 | 57.2 | 0.071 | 223427 | 393 | 224 | 1.76 | 12.4 | 103.2 |
| 26 | 2 | 1-Hf | diethylzinc | 400 | 38.1 | 0.086 | 406299 | 351 | 215 | 1.64 | 15.0 | 100.2 |
| 27 | 1 | 1-Hf | diethylzinc | 1600 | 36.0 | 0.073 | 365000 | 154 | 98 | 1.58 | 9.8 | 110.6 |
| 28 | 2 | 1-Hf | diethylzinc | 1600 | 38.4 | 0.071 | 332813 | 143 | 84 | 1.70 | 7.8 | 112.2 |
| 29 | 1 | 1-Hf | diethylzinc | 2800 | 43.1 | 0.066 | 275638 | 96 | 57 | 1.68 | 6.3 | 116.7 |
| 30 | 2 | 1-Hf | diethylzinc | 2800 | 47.6 | 0.061 | 230672 | 94 | 49 | 1.92 | 6.5 | 117.3 |
| 31 | 1 | 1-Hf | diethylzinc | 4000 | 32.9 | 0.069 | 377508 | 74 | 42 | 1.75 | 3.2 | 124.2 |
| 32 | 2 | 1-Hf | diethylzinc | 4000 | 31.0 | 0.067 | 389032 | 70 | 38 | 1.84 | 2.4 | 127.6 |
| 33 | 1 | 5-Zr | diethylzinc | 400 | 96.5 | 0.113 | 210777 | 860 | 432 | 1.99 | 0.0 | 131.0 |
| 34 | 2 | 5-Zr | diethylzinc | 400 | 140.0 | 0.105 | 135000 | 1131 | 539 | 2.10 | 0.4 | 130.9 |
| 35 | 1 | 5-Zr | diethylzinc | 1600 | 18.2 | 0.093 | 919780 | 224 | 124 | 1.81 | 0.0 | 136.6 |
| 36 | 2 | 5-Zr | diethylzinc | 1600 | 19.5 | 0.105 | 969231 | 230 | 135 | 1.70 | 0.0 | 134.1 |
| 37 | 1 | 5-Zr | diethylzinc | 2800 | 15.3 | 0.108 | 1270588 | 141 | 81 | 1.74 | 0.0 | 134.6 |
| 38 | 2 | 5-Zr | diethylzinc | 2800 | 15.2 | 0.109 | 1290789 | 155 | 91 | 1.71 | 0.7 | 134.9 |
| 39 | 1 | 5-Zr | diethylzinc | 4000 | 13.2 | 0.120 | 1636364 | 102 | 58 | 1.76 | 0.0 | 134.0 |
| 40 | 1 | 5-Hf | diethylzinc | 400 | 63.4 | 0.101 | 286751 | 673 | 314 | 2.14 | 0.5 | 129.5 |
| 41 | 2 | 5-Hf | diethylzinc | 400 | 38.9 | 0.082 | 379434 | 650 | 352 | 1.85 | 0.2 | 130.5 |
| 42 | 1 | 5-Hf | diethylzinc | 1600 | 45.0 | 0.064 | 256000 | 260 | 155 | 1.69 | 0.0 | 135.4 |
| 43 | 2 | 5-Hf | diethylzinc | 1600 | 39.2 | 0.069 | 316837 | 255 | 143 | 1.79 | 0.0 | 134.9 |
| 44 | 1 | 5-Hf | diethylzinc | 2800 | 21.9 | 0.086 | 706849 | 145 | 90 | 1.61 | 0.0 | 135.2 |
| 45 | 2 | 5-Hf | diethylzinc | 2800 | 20.7 | 0.082 | 713043 | 141 | 82 | 1.71 | 0.0 | 134.8 |
| 46 | 1 | 5-Hf | diethylzinc | 4000 | 21.2 | 0.083 | 704717 | 103 | 58 | 1.78 | 0.0 | 135.1 |
| 47 | 2 | 5-Hf | diethylzinc | 4000 | 19.9 | 0.077 | 696482 | 102 | 63 | 1.62 | 0.0 | 135.5 |
| 48 | 1 | 1-Zr | TNOAL | 400 | 43.2 | 0.111 | 462500 | 435 | 223 | 1.95 | 13.8 | 100.7 |
| 49 | 2 | 1-Zr | TNOAL | 400 | 29.4 | 0.102 | 624490 | 389 | 200 | 1.95 | 14.2 | 101.1 |
| 50 | 1 | 1-Zr | TNOAL | 1600 | 21.4 | 0.095 | 799065 | 183 | 101 | 1.81 | 13.3 | 105.7 |
| 51 | 2 | 1-Zr | TNOAL | 1600 | 21.1 | 0.094 | 801896 | 173 | 98 | 1.77 | 11.5 | 107.4 |
| 52 | 1 | 1-Zr | TNOAL | 2800 | 19.5 | 0.087 | 803077 | 116 | 64 | 1.82 | 8.9 | 109.6 |
| 53 | 2 | 1-Zr | TNOAL | 2800 | 18.4 | 0.085 | 831522 | 112 | 63 | 1.77 | 9.1 | 110.4 |
| 54 | 1 | 1-Zr | TNOAL | 4000 | 22.0 | 0.083 | 679091 | 85 | 51 | 1.68 | 10.8 | 112.5 |
| 55 | 2 | 1-Zr | TNOAL | 4000 | 18.8 | 0.075 | 718085 | 70 | 41 | 1.73 | 7.8 | 116.4 |
| 56 | 1 | 1-Hf | TNOAL | 400 | 193.8 | 0.122 | 113313 | 667 | 362 | 1.84 | 19.3 | 95.1 |
| 57 | 2 | 1-Hf | TNOAL | 400 | 98.6 | 0.121 | 220892 | 603 | 323 | 1.87 | 20.2 | 95.6 |
| 58 | 1 | 1-Hf | TNOAL | 1600 | 26.0 | 0.091 | 630000 | 171 | 110 | 1.56 | 14.2 | 101.8 |

TABLE 10-continued

Catalyst activity and polymer properties for EO copolymerization using various CTAs.

| Entry | Run | Catalyst | CTA | nmol Al or | Reaction Time | Yield (g) | Activity (g/mmol/hr) | Mw (kg/mol) | Mn (kg/mol) | Mw/Mn | wt % octene | Tm (° C.) |
|---|---|---|---|---|---|---|---|---|---|---|---|---|
| 59 | 2 | 1-Hf | TNOAL | 1600 | 29.0 | 0.087 | 540000 | 147 | 92 | 1.59 | 15.1 | 104.3 |
| 60 | 1 | 1-Hf | TNOAL | 2800 | 22.3 | 0.078 | 629596 | 90 | 54 | 1.65 | 11.4 | 109.2 |
| 61 | 2 | 1-Hf | TNOAL | 2800 | 24.0 | 0.082 | 615000 | 88 | 53 | 1.68 | 8.4 | 108.7 |
| 62 | 1 | 1-Hf | TNOAL | 4000 | 23.0 | 0.074 | 579130 | 59 | 34 | 1.73 | 9.7 | 113.6 |
| 63 | 2 | 1-Hf | TNOAL | 4000 | 26.8 | 0.079 | 530597 | 58 | 32 | 1.77 | 8.8 | 113.3 |
| 64 | 1 | 5-Zr | TNOAL | 400 | 55.5 | 0.113 | 366486 | 2613 | 1596 | 1.64 | 5.0 | 129.0 |
| 65 | 2 | 5-Zr | TNOAL | 400 | 49.8 | 0.118 | 426506 | 3603 | 2388 | 1.51 | 1.1 | 128.4 |
| 66 | 2 | 5-Zr | TNOAL | 1600 | 34.4 | 0.118 | 617442 | 3344 | 2192 | 1.53 | 4.2 | 128.9 |
| 67 | 1 | 5-Zr | TNOAL | 2800 | 49.3 | 0.111 | 405274 | 3298 | 2141 | 1.54 | 2.1 | 128.3 |
| 68 | 2 | 5-Zr | TNOAL | 2800 | 48.7 | 0.115 | 425051 | 3431 | 2388 | 1.44 | 1.6 | 128.7 |
| 69 | 1 | 5-Zr | TNOAL | 4000 | 49.7 | 0.105 | 380282 | 2724 | 1619 | 1.68 | 1.6 | 128.4 |
| 70 | 2 | 5-Zr | TNOAL | 4000 | 69.9 | 0.102 | 262661 | 3197 | 2059 | 1.55 | 1.7 | 128.4 |
| 71 | 1 | 5-Hf | TNOAL | 400 | 140.7 | 0.102 | 130490 | 3481 | 1970 | 1.77 | 2.6 | 125.4 |
| 72 | 2 | 5-Hf | TNOAL | 400 | 180.8 | 0.109 | 108518 | 3551 | 1747 | 2.03 | 4.6 | 125.4 |
| 73 | 1 | 5-Hf | TNOAL | 1600 | 154.0 | 0.110 | 128571 | 3465 | 2140 | 1.62 | 4.2 | 126.4 |
| 74 | 2 | 5-Hf | TNOAL | 1600 | 129.5 | 0.114 | 158456 | 3374 | 1276 | 2.64 | 4.8 | 125.0 |
| 75 | 1 | 5-Hf | TNOAL | 2800 | 167.2 | 0.105 | 113038 | 3464 | 1991 | 1.74 | 3.3 | 125.4 |
| 76 | 2 | 5-Hf | TNOAL | 2800 | 114.0 | 0.109 | 172105 | 3636 | 2342 | 1.55 | 3.1 | 125.4 |
| 77 | 1 | 5-Hf | TNOAL | 4000 | 146.7 | 0.106 | 130061 | 3598 | 2183 | 1.65 | 3.8 | 125.4 |
| 78 | 2 | 5-Hf | TNOAL | 4000 | 79.6 | 0.091 | 205779 | 3068 | 1472 | 2.08 | 2.6 | 126.1 |

DIBALO is bis(diisobutylaluminum)oxide. Entries 17 to 47 had 300 nmol of TNOAL in addition to the diethylzinc reagent.

Figure 2:
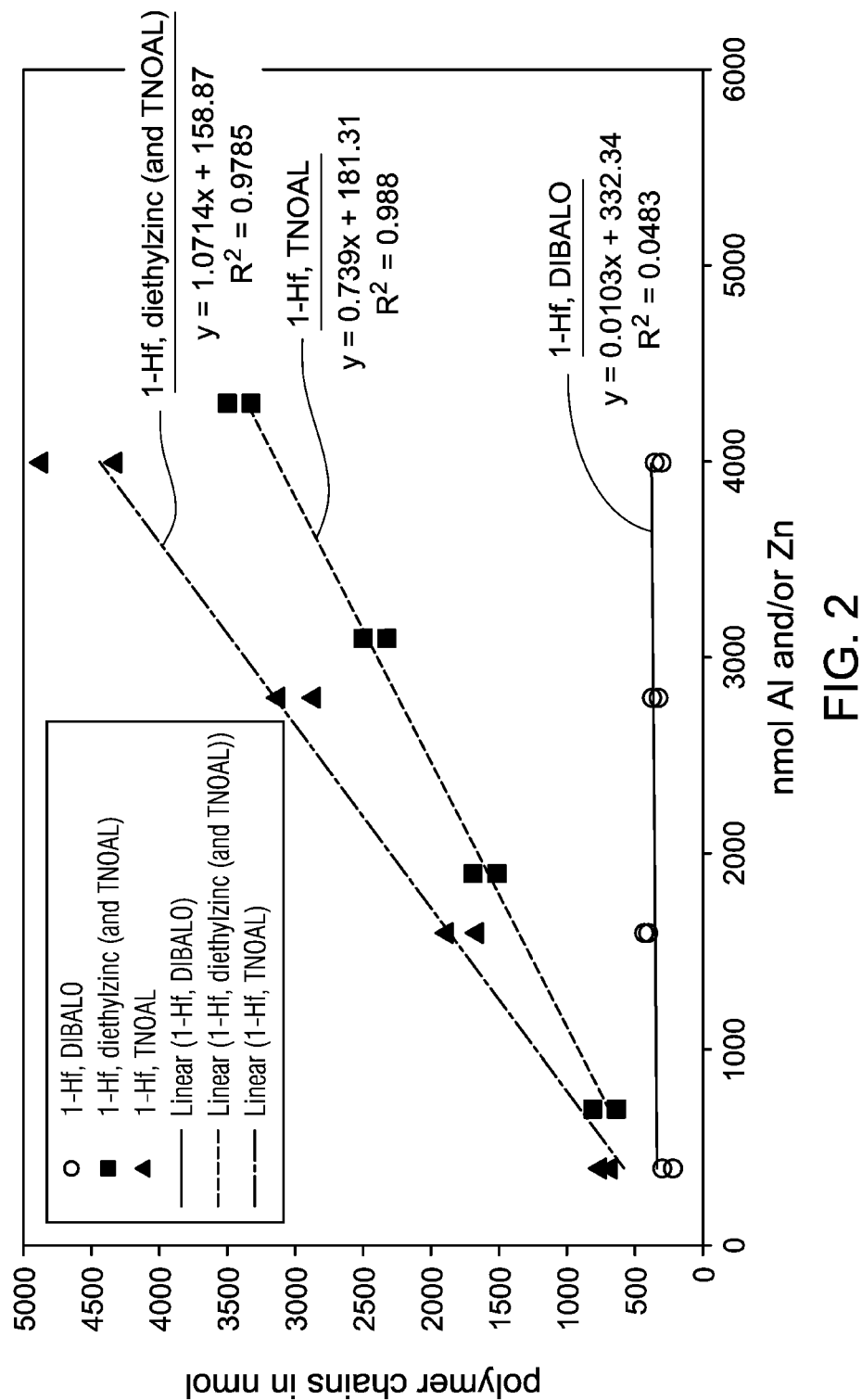
FIG. 2 presents a plot of polymer chains (nmol) versus nmol of metal (Al and/or Zn) from the chain transfer agent for entries 9 to 16, 25 to 32, and 56 to 63 in Table 10.
Figure 3:
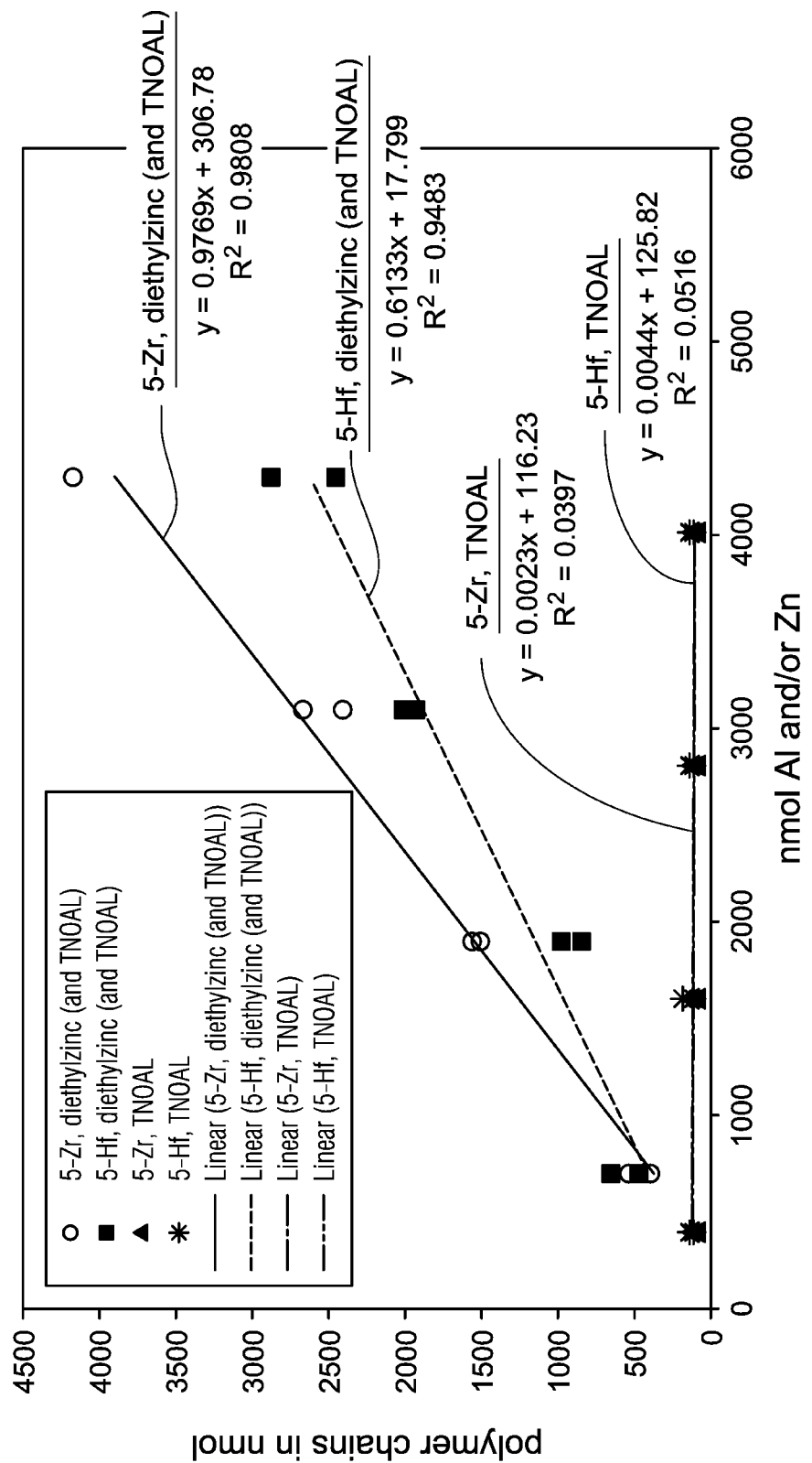
FIG. 3 presents a plot of polymer chains (nmol) versus nmol of metal (Al and/or Zn) from the chain transfer agent for entries 33 to 47 and 74 to 78 in Table 10.

The data from Table 10 are presented in FIGS. 1, 2 and 3. Mn numbers (based upon polystyrene standards) that were used to determine the nanomoles of polymer chains were corrected for EO by dividing the GPC values by 2.

FIG. 1 presents the chain transfer efficiency of 1-Zr from Table 10 Entries 1-8, 17-24 and 48-55. The equation and coefficient of determination of the linear fits (least squared fit, Microsoft™ Excel 2010) are included in the figure. The slope of the linear fit corresponds to the number of chains transferred to the CTA metal (per metal). This plot shows that both diethylzinc and TNOAL are effective CTAs with 1-Zr while no chain transfer occurs with DIBALO.

FIG. 2 presents the chain transfer efficiency of 1-Hf from Table 10 Entries 9-16, 25-32 and 56-63. The equation and coefficient of determination of the linear fits (least squared fit, Microsoft™ Excel 2010) are included in the figure. The slope of the linear fit corresponds to the number of chains transferred to the CTA metal (per metal). This plot shows that both diethylzinc and TNOAL are effective CTAs with 1-Hf while no chain transfer occurs with DIBALO.

FIG. 3 presents chain transfer efficiency of 5-Zr and 5-Hf from Table 10 Entries 33-47 and 74-78. The equation and coefficient of determination of the linear fits (least squared fit, Microsoft™ Excel 2010) are included in the figure. The slope of the linear fit corresponds to the number of chains transferred to the CTA metal (per metal). This plot shows that diethylzinc is an effective CTA with 5-Zr and 5-Hf while no chain transfer occurs with TNOAL.

Ethylene-Propylene Copolymerization in a Continuous Reactor.

The following examples were produced using a solution process in a 1.0-liter continuous stirred-tank reactor (autoclave reactor). The autoclave reactor was equipped with a stirrer, a water-cooling/steam-heating element with a temperature controller, and a pressure controller. Solvents and monomers were first purified by passing through a three-column purification system. Purification columns were regenerated periodically whenever there was evidence of low catalyst activity.

Isohexane was used as a solvent and was fed into the reactor using a Pulsa™ pump. Flow rate was controlled by adjusting the outflow at the pump. The compressed, liquefied propylene feed was controlled by a mass flow controller. Ethylene was mixed with propylene before the reactor and fed to the manifold. A mixture of isohexane and tri-n-octylaluminum (TNOAL) was also added to the manifold through a separate line and the combined mixture of monomers and solvent was fed into the reactor using a single tube. Reaction conditions are reported in the Table below.

The collected samples were first dried in a hood on a boiling-water steam bath to evaporate most of the solvent and unreacted monomers, and then dried in a vacuum oven at a temperature of about 90° C. for about 12 hours. The vacuum oven dried samples were weighed to obtain yields. Ethylene and propylene conversion was calculated based on the polymer yield, composition and the amount of monomers fed into the reactor. Catalyst efficiency was calculated based on the yield and the feed rate of catalyst (catalyst only). All the reactions were carried out at a gauge pressure of about 2.2 MPa.

Catalysts used in these examples were 1-Hf and 6-Hf. Activator used in both cases was N,N-dimethylanilinium tetrakis(pentafluorophenyl) borate. Both the catalyst and activator were first dissolved in toluene and the solutions were kept in an inert atmosphere. The solutions of catalyst and activator were premixed and fed into the reactor using an ISCO™ syringe pump. The catalyst to activator feed ratio (molar) was set at 0.98. Tri-n-octylaluminum (TNOAL) solution (available from Sigma Aldrich, Milwaukee, Wis.) was further diluted in isohexane and used as a scavenger.

Ethylene and propylene content is determined by FTIR, ASTM D3900.

GPC-SEC

Mw, Mn, and Mw/Mn are determined by using a High Temperature Size Exclusion Chromatograph (Polymer Laboratories), equipped with three in-line detectors, a differential refractive index detector (DRI), a light scattering (LS) detector, and a viscometer. Experimental details, including detector calibration, are described in: T. Sun, P. Brant, R. R. Chance, and W. W. Graessley, Macromolecules, Volume 34, Number 19, pp. 6812-6820, (2001), and references therein. Three Polymer Laboratories PLgel 10 μm Mixed-B LS columns are used. The nominal flow rate is 0.5 mL/min, and the nominal injection volume is 300 μL. The various transfer lines, columns, viscometer and differential refractometer (the DRI detector) are contained in an oven maintained at 145° C. Solvent for the experiment is prepared by dissolving 6 grams of butylated hydroxytoluene as an antioxidant in 4 liters of Aldrich reagent grade 1, 2, 4 trichlorobenzene (TCB). The TCB mixture is then filtered through a 0.1 μm Teflon filter. The TCB is then degassed with an online degasser before entering the Size Exclusion Chromatograph. Polymer solutions are prepared by placing dry polymer in a glass container, adding the desired amount of TCB, then heating the mixture at 160° C. with continuous shaking for about 2 hours. All quantities are measured gravimetrically. The TCB densities used to express the polymer concentration in mass/volume units are 1.463 g/ml at room temperature and 1.284 g/ml at 145° C. The injection concentration is from 0.5 to 2.0 mg/ml, with lower concentrations being used for higher molecular weight samples. Prior to running each sample the DRI detector and the injector are purged. Flow rate in the apparatus is then increased to 0.5 ml/minute, and the DRI is allowed to stabilize for 8 to 9 hours before injecting the first sample. The LS laser is turned on at least 1 to 1.5 hours before running the samples. The concentration, c, at each point in the chromatogram is calculated from the baseline-subtracted DRI signal, $I_{DRI}$, using the following equation: $c=K_{DRI}I_{DRI}/(dn/dc)$ where $K_{DRI}$ is a constant determined by calibrating the DRI, and (dn/dc) is the refractive index increment for the system. The refractive index, n=1.500 for TCB at 145° C. and λ=660 nm.

Units on parameters throughout this description of the GPC-SEC method are such that concentration is expressed in g/cm$^3$, molecular weight is expressed in g/mole, and intrinsic viscosity is expressed in dL/g.

The LS detector is a Wyatt Technology High Temperature DAWN HELEOS. The molecular weight, M, at each point in the chromatogram is determined by analyzing the LS output using the Zimm model for static light scattering (M. B. Huglin, Light Scattering From Polymer Solutions, Academic Press, 1971):

$$\frac{K_o c}{\Delta R(\theta)} = \frac{1}{MP(\theta)} + 2A_2 c$$

Here, $\Delta R(\theta)$ is the measured excess Rayleigh scattering intensity at scattering angle θ, c is the polymer concentration determined from the DRI analysis, $A_2$ is the second virial coefficient, for purposes of this invention $A_2$=0.0006, (dn/dc) is the refractive index increment for the system. P(θ) is the form factor for a monodisperse random coil, and $K_o$ is the optical constant for the system:

$$K_o = \frac{4\pi^2 n^2 (dn/dc)^2}{\lambda^4 N_A}$$

where $N_A$ is Avogadro's number, and (dn/dc) is the refractive index increment for the system. The refractive index, n=1.500 for TCB at 145° C. and λ=660 nm.

All molecular weights are weight average unless otherwise noted. All molecular weights are reported in g/mol unless otherwise noted.

TABLE 1

Catalyst efficiency and polymer properties for ethylene-propylene copolymerization in a continuous reactor.

| | Run | | | | | |
|---|---|---|---|---|---|---|
| | 1 | 2 | 3 | 1 | 2 | 3 |
| Catalyst | 1-Hf | 1-Hf | 1-Hf | 6-Hf | 6-Hf | 6-Hf |
| Activator | Activator-1 | Activator-1 | Activator-1 | Activator-1 | Activator-1 | Activator-1 |
| Temp (° C.) | 120 | 120 | 120 | 120 | 120 | 120 |
| C2 = Feed (g/min) | 2 | 2 | 2 | 2 | 2 | 2 |
| C3 = Feed (g/min) | 4.5 | 4.5 | 4.5 | 4.5 | 4.5 | 4.5 |
| Catalyst Feed (mol/min) | 8.85E−08 | 2.65E−07 | 1.77E−07 | 8.73E−08 | 1.75E−07 | 2.62E−07 |
| TNOAL (mol/min) | 7.74E−06 | 7.74E−06 | 7.74E−06 | 7.74E−06 | 7.74E−06 | 7.74E−06 |
| Cement Concn (wt %) | 2.6 | 4.4 | 4.2 | NO POLYMER PRODUCED | | |
| Ethylene (wt %) FT-IR* | 78.5 | 70.1 | 66.1 | | | |
| Propylene (wt %) FT-IR* | 21.5 | 29.9 | 33.9 | | | |
| Yield (g) | 35.2 | 61.4 | 69.3 | | | |
| Rxn Time (min) | 30 | 30 | 30 | | | |
| Polymer (g/min) | 1.17 | 2.05 | 2.31 | | | |
| Catalyst Efficiency | 13,037* | 11,370* | 8,556* | | | |
| Mw (kg/mol) GPC-SEC | 133 | 137 | 186 | | | |
| Mn (kg/mol) GPC-SEC | 76 | 80 | 71 | | | |
| Mw/Mn | 1.74 | 1.72 | 2.62 | | | |

*(g polymer/g catalyst)

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. The term "comprising" is considered synonymous with the term "including". Likewise, whenever a composition, an element, or a group of elements is preceded with the transitional phrase "comprising", it is understood that we also contemplate the same composition or group of elements with transitional phrases "consisting essentially of," "consisting of," "selected from the group of consisting of," or is preceding the recitation of the composition, element, or elements and vice versa.

What is claimed is:

1. A transition metal complex represented by the formula (I):

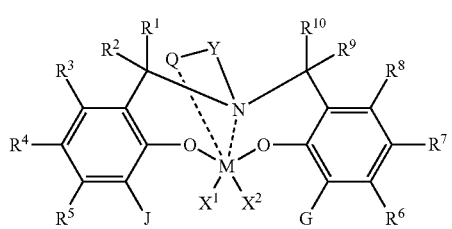

(I)

wherein M is a Group 4 transition metal;

$X^1$ and $X^2$ are, independently, a univalent $C_1$ to $C_{20}$ hydrocarbyl radical, a $C_1$ to $C_{20}$ substituted hydrocarbyl radical, a heteroatom or a heteroatom-containing group, or $X^1$ and $X^2$ join together to form a $C_4$ to $C_{62}$ cyclic or polycyclic ring structure;

each $R^1$, $R^2$, $R^3$, $R^4$, $R^5$, $R^6$, $R^7$, $R^8$, $R^9$ and $R^{10}$ is, independently, a hydrogen, a $C_1$-$C_{40}$ hydrocarbyl radical, a $C_1$-$C_{40}$ substituted hydrocarbyl radical, a heteroatom or a heteroatom-containing group, or two or more of $R^1$ to $R^{10}$ may independently join together to form a $C_4$ to $C_{62}$ cyclic or polycyclic ring structure, or a combination thereof; and Q is a neutral donor group;

J is a $C_7$ to $C_{60}$ fused polycyclic group, which optionally comprises up to 20 atoms from Groups 15 and 16, where at least one ring is aromatic and where at least one ring, which may or may not be aromatic, has at least five members;

G is as defined for J or may be hydrogen, a $C_1$-$C_{60}$ hydrocarbyl radical, a $C_1$-$C_{60}$ substituted hydrocarbyl radical, a heteroatom or a heteroatom-containing group, or may independently form a $C_4$ to $C_{60}$ cyclic or polycyclic ring structure with $R^6$, $R^7$, or $R^8$ or a combination thereof; and Y is a divalent $C_1$ to $C_{20}$ hydrocarbyl or divalent $C_1$ to $C_{20}$ substituted hydrocarbyl.

2. The transition metal complex of claim 1, wherein the complex is represented by the formula (II) or (III):

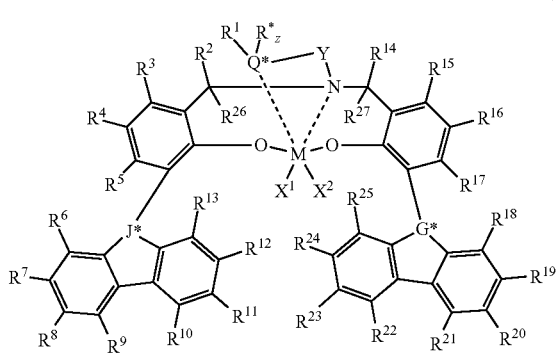

(II)

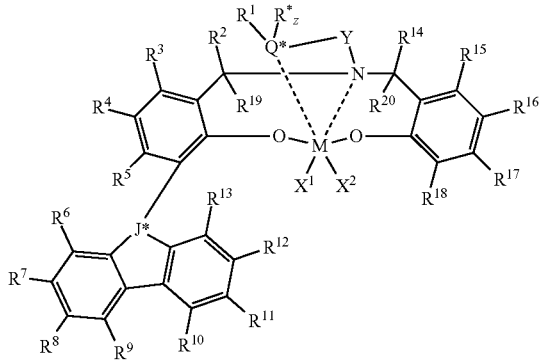

(III)

wherein M, $X^1$, $X^2$, $R^1$, $R^2$, $R^3$, $R^4$, $R^5$, $R^6$, $R^7$, $R^8$, $R^9$, $R^{10}$, and Y are as defined in claim 1;

each R*, R″, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, and $R^{27}$ is, independently, a hydrogen, a $C_1$-$C_{40}$ hydrocarbyl radical, a $C_1$-$C_{40}$ substituted hydrocarbyl radical a functional group comprising elements from Groups 13-17 of the periodic table of the elements, or two or more of $R^1$ to $R^{28}$ may independently join together to form a $C_4$ to $C_{62}$ cyclic or polycyclic ring structure, or a combination thereof, or $R^1$ and R* may independently join together to form a five- to eight-membered heterocycle; and Q* is a group 15 or 16 atom;

z is 0 or 1;

J* is CR″ or N; and

G* is CR″ or N.

3. The complex of claim 1, wherein M is Hf or Zr or Ti.

4. The complex of claim 1, wherein G and J are carbazolyl, substituted carbazolyl, indolyl, substituted indolyl, indolinyl, substituted indolinyl, imidazolyl, substituted imidazolyl, indenyl, substituted indenyl, indanyl, substituted indanyl, fluorenyl, or substituted fluorenyl.

5. The complex of claim 1, wherein Q is a neutral donor group comprising at least one atom from Group 15 or Group 16 and the -(-Q-Y—)— fragment optionally form a substituted or unsubstituted heterocycle which may or may not be aromatic and may have multiple fused rings.

6. The complex of claim 1, wherein Q is $NR'_2$, OR', SR', $PR'_2$, where R' is as defined for $R^1$.

7. The complex of claim 1, wherein G and J are the same.

8. The complex of claim 1, wherein G is a hydrogen, a $C_1$-$C_{60}$ hydrocarbyl radical, a substituted hydrocarbyl radical, a heteroatom, or a heteroatom-containing group, or may independently form a $C_4$ to $C_{60}$ cyclic or polycyclic ring structure with $R^6$, $R^7$, or $R^8$, or a combination thereof.

9. The complex of claim 1, wherein the complex is represented by formula (IV) or (V):

(IV)

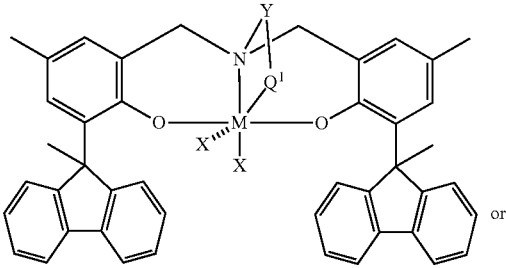

or

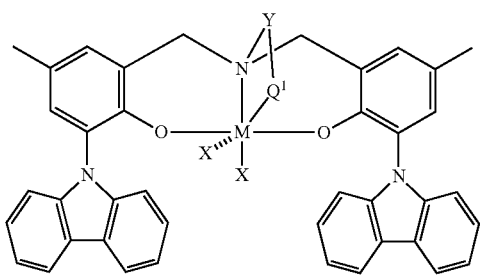

(V)

where Y is a divalent $C_1$ to $C_3$ hydrocarbyl, $Q^1$ is $NR'_2$, OR', SR', $PR'_2$, where R' is as defined for $R^1$ in claim 1, M is Zr, Hf or Ti and each X is, independently, as defined for $X^1$ in claim 1.

10. The complex of claim 2, wherein Q* is N, O, S or P, and when Q* is a N or P, z is 1 and when Q* is a S or O z is 0, and G* and J* are N or CR''', where each R''' is H or a $C_1$ to $C_{12}$ alkyl.

11. A catalyst system comprising an activator and the complex of claim 1.

12. The catalyst system of claim 11, wherein G and J are, independently, carbazolyl, substituted carbazolyl, indolyl, substituted indolyl, indolinyl, substituted indolinyl, imidazolyl, substituted imidazolyl, indenyl, substituted indenyl, indanyl, substituted indanyl, fluorenyl, or substituted fluorenyl.

13. The catalyst system of claim 11, wherein the catalyst complex is represented by formula (IV) or (V):

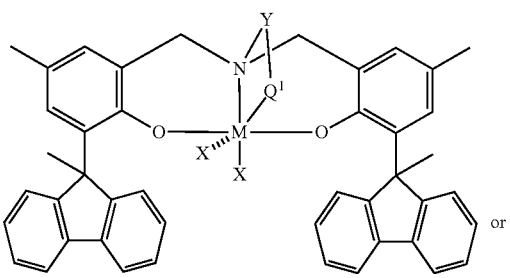

(IV)

or

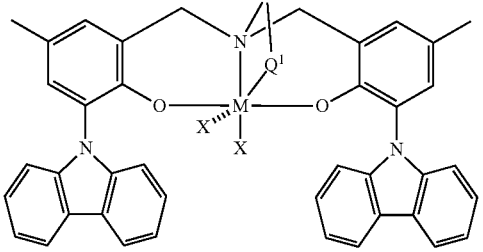

(V)

where Y is a divalent $C_1$ to $C_3$ hydrocarbyl, $Q^1$ is $NR'_2$, OR', SR', $PR'_2$, where R' is as defined for $R^1$ in claim 1, M is Zr, Hf or Ti and each X is, independently, as defined for $X^1$ in claim 1.

14. The catalyst system of claim 11, wherein G and J are the same.

15. The catalyst system of claim 11, wherein the catalyst system further comprises chain transfer agent.

16. The catalyst system of claim 11, wherein the catalyst system further comprises chain transfer agent represented by the formula $R^3Al$ or $R^2Zn$, where R is a $C_1$ to $C_{20}$ alkyl group.

17. The catalyst system of claim 11, wherein the activator is an alumoxane.

18. The catalyst system of claim 11, wherein the activator is a non-coordinating anion.

19. The catalyst system of claim 11, wherein the activator is selected from the group consisting of: methylalumoxane, ethylalumoxane, isobutyl alumoxane, N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetra(perfluorophenyl)borate, triphenylcarbenium tetrakis(perfluorophenyl)borate, 1-(4-(tris(pentafluorophenyl)borate)-2,3,5,6-tetrafluorophenyl)pyrrolidinium, tetrakis(pentafluorophenyl)borate, and 4-(tris(pentafluorophenyl)borate)-2,3,5,6-tetrafluoropyridine.

20. A polymerization process to produce polyolefin comprising:
  a) contacting one or more olefin monomers with the catalyst system of claim 11, and
  b) obtaining olefin polymer.

21. The process of claim 20, wherein the activator is an alumoxane or a non-coordinating anion.

22. The process of claim 20, wherein the activator is selected from the group consisting of: methylalumoxane, ethylalumoxane, isobutyl alumoxane, N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, triphenylcarbenium tetra(perfluorophenyl)borate, triphenylcarbenium tetrakis(perfluorophenyl)borate, 1-(4-(tris(pentafluorophenyl)borate)-2,3,5,6-tetrafluorophenyl)pyrrolidinium, tetrakis(pentafluorophenyl)borate, and 4-(tris(pentafluorophenyl)borate)-2,3,5,6-tetrafluoropyridine.

23. The process of claim 20, wherein the monomer comprises ethylene.

24. The process of claim 20, wherein the monomer comprises propylene.

25. The process of claim 20, wherein the transition metal complex is supported.

26. The process of claim 20, wherein a chain transfer agent is present.

27. The process of claim 20, wherein chain transfer agent represented by the formula $R^3Al$ or $R^2Zn$ is present at a molar ratio of transition metal to Al or Zn of at least 10:1, where R is a $C_1$ to $C_{40}$ alkyl group.

28. The process of claim 20, wherein a chain transfer agent represented by the formula $R^3Al$ and a chain transfer agent represented by the formula $R^2Zn$ are present at a molar ratio of transition metal to Al and Zn of at least 100:1, where R is a $C_1$ to $C_{20}$ alkyl group.

29. The process of claim 20, wherein the process is a continuous process.

30. The process of claim 20, wherein step a) occurs at a temperature of at least 120° C.

31. The process of claim 20, wherein step a) occurs at a temperature of at least 130° C.

32. The process of claim 20, wherein hydrogen is present in step a).

33. The process of claim 20, wherein hydrogen and a chain transfer agent are present in step a).

* * * * *